(12) United States Patent
Henley

(10) Patent No.: US 12,238,265 B2
(45) Date of Patent: Feb. 25, 2025

(54) OPTICAL FILTER FOR IMPROVED MULTISPECTRAL IMAGING PERFORMANCE IN STEREO CAMERA

(71) Applicant: Cilag GmbH International, Zug (CH)

(72) Inventor: Jeremiah D. Henley, Fair Oaks, CA (US)

(73) Assignee: Cilag GmbH International, Zug (CH)

( * ) Notice: Subject to any disclaimer, the term of this patent is extended or adjusted under 35 U.S.C. 154(b) by 136 days.

(21) Appl. No.: 18/064,846

(22) Filed: Dec. 12, 2022

(65) Prior Publication Data

US 2024/0195948 A1 Jun. 13, 2024

(51) Int. Cl.
| | |
|---|---|
| H04N 13/257 | (2018.01) |
| H04N 13/239 | (2018.01) |
| H04N 13/25 | (2018.01) |
| H04N 13/254 | (2018.01) |
| H04N 23/11 | (2023.01) |
| H04N 23/16 | (2023.01) |
| H04N 23/50 | (2023.01) |

(52) U.S. Cl.
CPC ......... *H04N 13/257* (2018.05); *H04N 13/239* (2018.05); *H04N 13/25* (2018.05); *H04N 13/254* (2018.05); *H04N 23/11* (2023.01); *H04N 23/16* (2023.01); *H04N 23/555* (2023.01)

(58) Field of Classification Search
CPC .... H04N 13/257; H04N 13/239; H04N 13/25; H04N 13/254; H04N 23/11; H04N 23/16; H04N 23/555; H04N 13/207; H04N 13/296; H04N 23/55; H04N 23/56; H04N 23/74; G01N 2021/6471; G01N 21/6456; A61B 1/046; A61B 1/00186; A61B 1/043; A61B 1/0638; A61B 1/0655; A61B 1/00193

USPC .......................................................... 348/45
See application file for complete search history.

(56) References Cited

U.S. PATENT DOCUMENTS

| | | | |
|---|---|---|---|
| 7,046,270 B2 | 5/2006 | Murata et al. | |
| 7,621,868 B2 | 11/2009 | Breidenthal et al. | |
| 8,045,850 B2 | 10/2011 | Tanoue | |
| 8,248,414 B2 | 8/2012 | Gattani et al. | |
| 8,443,279 B1 | 5/2013 | Hameed et al. | |
| 8,734,328 B2 | 5/2014 | McDowall | |
| 8,764,633 B2 | 7/2014 | McDowall | |

(Continued)

OTHER PUBLICATIONS

International Search Report for International Application No. PCT/IB2023/062472 dated Mar. 19, 2024.

*Primary Examiner* — Susan E. Torgerson
(74) *Attorney, Agent, or Firm* — TechLaw Ventures, PLLC; Terrence J. Edwards

(57) ABSTRACT

Stereo visualization systems with optical filters for selective detection of color, multispectral, fluorescence, and laser mapping image data. A system includes a stereo camera comprising a first image sensor and a second image sensor, with a first optical filter that prevents the first image sensor from accumulating near infrared electromagnetic radiation. The system includes an emitter comprising a plurality of sources of electromagnetic radiation. The first image sensor detects visible electromagnetic radiation and reads out a visible data frame in response to the emitter cycling on a visible source, and the second image sensor detects near infrared electromagnetic radiation and reads out a near infrared data frame in response to the emitter cycling on a near infrared source.

20 Claims, 24 Drawing Sheets

(56) References Cited

U.S. PATENT DOCUMENTS

| | | | |
|---|---|---|---|
| 8,784,301 B2 | 7/2014 | McDowall | |
| 8,803,955 B2 | 8/2014 | Scott et al. | |
| 8,814,779 B2 | 8/2014 | Shafer et al. | |
| 8,996,086 B2 * | 3/2015 | Chinnock | A61B 5/0075 600/310 |
| 9,092,556 B2 | 7/2015 | Amble et al. | |
| 9,153,284 B2 | 10/2015 | Shibata | |
| 9,254,076 B2 | 2/2016 | McDowall | |
| 9,420,220 B2 | 8/2016 | Nieten et al. | |
| 9,462,234 B2 | 10/2016 | Blanquart et al. | |
| 9,492,060 B2 | 11/2016 | Blanquart | |
| 9,509,917 B2 | 11/2016 | Blanquart et al. | |
| 9,516,239 B2 | 12/2016 | Blanquart et al. | |
| 9,621,817 B2 | 4/2017 | Blanquart et al. | |
| 9,635,343 B2 | 4/2017 | Kasumi et al. | |
| 9,641,799 B2 | 5/2017 | Smurro | |
| 9,641,815 B2 | 5/2017 | Richardson et al. | |
| 9,661,990 B2 | 5/2017 | Hofer | |
| 9,713,419 B2 | 7/2017 | Shahinian et al. | |
| 9,762,879 B2 | 9/2017 | Blanquart et al. | |
| 9,777,913 B2 | 10/2017 | Talbert et al. | |
| 9,782,056 B2 | 10/2017 | McDowall | |
| 9,793,308 B2 | 10/2017 | Gidon | |
| 9,980,629 B2 | 5/2018 | King | |
| 10,075,626 B2 | 9/2018 | Blanquart et al. | |
| 10,134,126 B2 | 11/2018 | Fram | |
| 10,165,195 B2 | 12/2018 | Blanquart et al. | |
| 10,175,469 B2 | 1/2019 | Haigis et al. | |
| 10,205,877 B2 | 2/2019 | Richardson et al. | |
| 10,206,561 B2 | 2/2019 | Wichern et al. | |
| 10,250,819 B2 | 4/2019 | Hosono et al. | |
| 10,251,530 B2 | 4/2019 | Henley et al. | |
| 10,254,533 B2 | 4/2019 | McDowall | |
| 10,277,875 B2 | 4/2019 | Blanquart et al. | |
| 10,299,732 B2 | 5/2019 | Henley et al. | |
| 10,330,914 B2 | 6/2019 | Togino | |
| 10,330,945 B2 | 6/2019 | Katsuki | |
| 10,341,588 B2 | 7/2019 | Richardson et al. | |
| 10,341,593 B2 | 7/2019 | Blanquart et al. | |
| 10,342,410 B2 | 7/2019 | Schwartz et al. | |
| 10,356,392 B2 | 7/2019 | Nabeel | |
| 10,362,240 B2 | 7/2019 | Richardson et al. | |
| 10,365,554 B1 | 7/2019 | McDowall et al. | |
| 10,389,926 B2 | 8/2019 | Shibata | |
| 10,426,322 B2 | 10/2019 | Tsuchiya et al. | |
| 10,477,127 B2 | 11/2019 | Blanquart | |
| 10,506,142 B2 | 12/2019 | Talbert et al. | |
| 10,506,914 B2 | 12/2019 | Dicarlo et al. | |
| 10,512,512 B2 | 12/2019 | Richmond et al. | |
| 10,517,469 B2 | 12/2019 | Blanquart et al. | |
| 10,524,644 B2 | 1/2020 | Scott et al. | |
| 10,561,302 B2 | 2/2020 | Henley et al. | |
| 10,568,496 B2 | 2/2020 | Blanquart et al. | |
| 10,573,015 B2 | 2/2020 | Fukunishi et al. | |
| 10,574,968 B2 | 2/2020 | Hayashi | |
| 10,607,653 B2 | 3/2020 | Hayashi et al. | |
| 10,663,715 B2 | 5/2020 | Ogasawara | |
| 10,666,927 B2 | 5/2020 | Bendall | |
| 10,670,248 B2 | 6/2020 | Talbert et al. | |
| 10,695,003 B2 | 6/2020 | Henley et al. | |
| 10,698,194 B2 | 6/2020 | Zhao | |
| 10,701,254 B2 | 6/2020 | Blanquart et al. | |
| 10,729,502 B1 | 8/2020 | Wolf et al. | |
| 10,733,717 B2 | 8/2020 | Takahashi | |
| 10,742,895 B2 | 8/2020 | Blanquart et al. | |
| 10,750,933 B2 | 8/2020 | Blanquart | |
| 10,754,241 B2 | 8/2020 | McDowall et al. | |
| 10,758,314 B2 | 9/2020 | Wade | |
| 10,785,410 B2 | 9/2020 | Toyoda et al. | |
| 10,785,428 B2 | 9/2020 | Wang et al. | |
| 10,785,461 B2 | 9/2020 | Blanquart et al. | |
| 10,809,519 B2 | 10/2020 | McDowall | |
| 10,839,955 B2 | 11/2020 | Accomazzi et al. | |
| 10,855,942 B2 | 12/2020 | Blanquart | |
| 10,881,272 B2 | 1/2021 | Blanquart | |
| 10,917,562 B2 | 2/2021 | Richardson et al. | |
| 10,924,724 B2 | 2/2021 | Shioda et al. | |
| 10,932,656 B2 | 3/2021 | Peleg | |
| 10,952,619 B2 | 3/2021 | Talbert et al. | |
| 10,956,492 B2 | 3/2021 | Barral et al. | |
| 10,958,852 B2 | 3/2021 | Fukumoto | |
| 10,972,690 B2 | 4/2021 | Blanquart et al. | |
| 10,980,406 B2 | 4/2021 | Blanquart et al. | |
| 10,984,550 B2 | 4/2021 | Matsunaga et al. | |
| 10,993,604 B2 | 5/2021 | Khettal et al. | |
| 11,006,113 B2 | 5/2021 | Fuchie et al. | |
| 11,056,226 B2 | 7/2021 | Shibata | |
| 11,062,419 B1 | 7/2021 | Fell | |
| 11,070,779 B2 | 7/2021 | Blanquart et al. | |
| 11,082,627 B2 | 8/2021 | Blanquart et al. | |
| 11,083,367 B2 | 8/2021 | Blanquart et al. | |
| 11,089,192 B2 | 8/2021 | Blanquart et al. | |
| 11,096,565 B2 | 8/2021 | Talbert et al. | |
| 11,109,744 B2 | 9/2021 | Uchimura et al. | |
| 11,115,610 B2 | 9/2021 | Richardson et al. | |
| 11,123,150 B2 | 9/2021 | Ichiki et al. | |
| 11,134,832 B2 | 10/2021 | Talbert et al. | |
| 11,156,809 B2 | 10/2021 | Uchida | |
| 11,185,213 B2 | 11/2021 | Henley et al. | |
| 11,187,886 B2 | 11/2021 | Uchida | |
| 11,196,904 B2 | 12/2021 | Talbert et al. | |
| 11,206,340 B2 | 12/2021 | Talbert et al. | |
| 11,213,194 B2 | 1/2022 | Talbert et al. | |
| 11,237,270 B2 | 2/2022 | Talbert et al. | |
| 11,238,592 B2 | 2/2022 | Maimon et al. | |
| 11,240,426 B2 | 2/2022 | Talbert et al. | |
| 11,253,139 B2 | 2/2022 | Blanquart | |
| 11,266,305 B2 | 3/2022 | Wichern et al. | |
| 11,281,940 B2 | 3/2022 | Toyoda et al. | |
| 11,284,785 B2 | 3/2022 | Talbert et al. | |
| 11,294,062 B2 | 4/2022 | Talbert et al. | |
| 11,317,014 B2 | 4/2022 | Sambongi et al. | |
| 11,317,788 B2 | 5/2022 | Schouwink et al. | |
| 11,344,189 B2 | 5/2022 | Blanquart et al. | |
| 11,361,406 B2 | 6/2022 | Kimura et al. | |
| 11,363,942 B2 | 6/2022 | Schouwink et al. | |
| 11,368,609 B2 | 6/2022 | Tokuse et al. | |
| 11,373,422 B2 | 6/2022 | Sakane | |
| 11,375,884 B2 | 7/2022 | Shahinian et al. | |
| 11,376,094 B2 | 7/2022 | Wade | |
| 11,380,431 B2 | 7/2022 | Wolf et al. | |
| 11,389,066 B2 | 7/2022 | Talbert et al. | |
| 11,382,496 B2 | 8/2022 | Kamikawa et al. | |
| 11,399,717 B2 | 8/2022 | Talbert et al. | |
| 11,405,560 B2 | 8/2022 | Kulcke et al. | |
| 11,419,696 B2 | 8/2022 | Kamikawa et al. | |
| 11,425,322 B2 | 8/2022 | Blanquart et al. | |
| 11,431,911 B2 | 8/2022 | Kita et al. | |
| 11,432,704 B2 | 9/2022 | Adachi | |
| 11,446,113 B2 | 9/2022 | Nakamura et al. | |
| 11,457,154 B2 | 9/2022 | Talbert et al. | |
| 11,470,227 B2 | 10/2022 | Talbert et al. | |
| 11,484,270 B2 | 11/2022 | Henley et al. | |
| 11,516,387 B2 | 11/2022 | Talbert et al. | |
| 11,531,112 B2 | 12/2022 | Talbert et al. | |
| 11,539,880 B2 | 12/2022 | Richardson et al. | |
| 11,574,412 B2 | 2/2023 | Talbert et al. | |
| 11,575,811 B2 | 2/2023 | Talbert et al. | |
| 11,622,677 B2 | 4/2023 | Talbert et al. | |
| 11,671,581 B2 | 6/2023 | Shafer et al. | |
| 2017/0020627 A1 | 1/2017 | Tesar et al. | |
| 2017/0209050 A1 * | 7/2017 | Fengler | H04N 23/74 |
| 2019/0125454 A1 | 5/2019 | Stokes et al. | |
| 2019/0191974 A1 | 6/2019 | Talbert et al. | |
| 2019/0191975 A1 | 6/2019 | Talbert et al. | |
| 2019/0191976 A1 | 6/2019 | Talbert et al. | |
| 2019/0191977 A1 | 6/2019 | Talbert et al. | |
| 2019/0191978 A1 | 6/2019 | Talbert et al. | |
| 2019/0356867 A1 | 11/2019 | Richardson et al. | |
| 2020/0008660 A1 | 1/2020 | Uchida et al. | |
| 2020/0126655 A1 | 4/2020 | Sasaki et al. | |
| 2020/0178769 A1 | 6/2020 | Henley et al. | |
| 2020/0184640 A1 | 6/2020 | Mahadik et al. | |
| 2020/0292160 A1 | 9/2020 | Talbert et al. | |

(56) References Cited

U.S. PATENT DOCUMENTS

| | | |
|---|---|---|
| 2020/0363624 A1 | 11/2020 | Zhao |
| 2020/0379334 A1 | 12/2020 | McDowall et al. |
| 2020/0397246 A1 | 12/2020 | Talbert et al. |
| 2020/0397277 A1* | 12/2020 | Talbert ............... A61B 1/00042 |
| 2020/0404131 A1 | 12/2020 | Talbert et al. |
| 2021/0103137 A1 | 4/2021 | McDowell |
| 2021/0120149 A1 | 4/2021 | Jauss |
| 2021/0160444 A1 | 5/2021 | Blanquart |
| 2021/0274998 A1 | 9/2021 | Thomas et al. |
| 2021/0295502 A1 | 9/2021 | Michihata et al. |
| 2021/0313044 A1 | 10/2021 | Shibata |
| 2021/0330177 A1 | 10/2021 | Kohno et al. |
| 2021/0344885 A1 | 11/2021 | Blanquart et al. |
| 2021/0360142 A1 | 11/2021 | Blanquart et al. |
| 2021/0361152 A1 | 11/2021 | Blanquart et al. |
| 2021/0368076 A1 | 11/2021 | Blanquart et al. |
| 2021/0378495 A1 | 12/2021 | Talbert et al. |
| 2021/0409627 A1 | 12/2021 | Richardson et al. |
| 2022/0047148 A1 | 2/2022 | Henley et al. |
| 2022/0107418 A1 | 4/2022 | Talbert et al. |
| 2022/0109790 A1 | 4/2022 | Talbert et al. |
| 2022/0125285 A1 | 4/2022 | Talbert et al. |
| 2022/0175234 A1 | 6/2022 | Wichern et al. |
| 2022/0182538 A1 | 6/2022 | Kubo et al. |
| 2022/0192474 A1 | 6/2022 | Talbert et al. |
| 2022/0236421 A1 | 7/2022 | Talbert et al. |
| 2022/0248941 A1 | 8/2022 | Blanquart |
| 2022/0287552 A1 | 9/2022 | Blanquart et al. |
| 2022/0296082 A1 | 9/2022 | Shiraki |
| 2022/0327707 A1 | 10/2022 | Nishide |
| 2022/0330799 A1* | 10/2022 | Kennedy ............... A61B 90/361 |
| 2022/0330826 A1 | 10/2022 | Talbert et al. |
| 2022/0334061 A1 | 10/2022 | Talbert et al. |
| 2022/0346650 A1 | 11/2022 | Novak et al. |
| 2022/0378294 A1 | 12/2022 | Talbert et al. |
| 2022/0383453 A1 | 12/2022 | Talbert et al. |
| 2022/0394199 A1 | 12/2022 | Blanquart et al. |
| 2023/0028618 A1 | 1/2023 | Talbert et al. |
| 2023/0080490 A1 | 3/2023 | Henley et al. |
| 2023/0111981 A1 | 4/2023 | Talbert et al. |
| 2023/0130164 A1 | 4/2023 | Talbert et al. |
| 2023/0137694 A1 | 5/2023 | Richardson et al. |

\* cited by examiner

Bayer Pattern Array
1402

| B1 | G1 | B2 | G2 | B5 | G5 | B6 | G6 |
|----|----|----|----|----|----|----|----|
| g1 | R1 | g2 | R2 | g5 | R5 | g6 | R6 |
| B3 | G3 | B4 | G4 | B7 | G7 | B8 | G8 |
| g3 | R3 | g4 | R4 | g7 | R7 | g8 | R7 |
| B9 | G9 | B10 | G10 | B13 | G13 | B14 | G14 |
| g9 | R9 | g10 | R10 | g13 | R13 | g14 | R14 |
| B11 | G11 | B12 | G12 | B15 | G15 | B16 | G16 |
| g11 | R11 | g12 | R12 | g15 | R15 | g16 | R16 |

Binned Readout
1404

| B1, B2, B3, B4 | G1, G2, G3, G4 | B5, B6, B7, B8 | G5, G6, G7, G8 |
|----------------|----------------|----------------|----------------|
| g1, g2, g3, g4 | R1, R2, R3, R4 | g5, g6, g7, g8 | R5, R6, R7, R8 |
| B9, B10, B11, B12 | G9, G10, G11, G12 | B13, B14, B15, B16 | G13, G14, G15, G13 |
| g9, g10, g11, g12 | R9, R10, R11, R12 | g13, g14, g15, g16 | R13, R14, R15, R16 |

FIG. 14A

Quad Bayer Pattern Array
1412

| B1 | B1 | G1 | G1 | B2 | B2 | G2 | G2 |
|----|----|----|----|----|----|----|----|
| B1 | B1 | G1 | G1 | B2 | B2 | G2 | G2 |
| g1 | g1 | R1 | R1 | g2 | g2 | R2 | R2 |
| g1 | g1 | R1 | R1 | g2 | g2 | R2 | R2 |
| B3 | B3 | G3 | G3 | B4 | B4 | G4 | G4 |
| B3 | B3 | G3 | G3 | B4 | B4 | G4 | G4 |
| g3 | g3 | R3 | R3 | g4 | g4 | R4 | R4 |
| g3 | g3 | R3 | R3 | g4 | g4 | R4 | R4 |

Binned Readout
1414

| B1 | G1 | B2 | G2 |
|----|----|----|----|
| g1 | R1 | g2 | R2 |
| B3 | G3 | B4 | G4 |
| g3 | R3 | g4 | R4 |

FIG. 14B

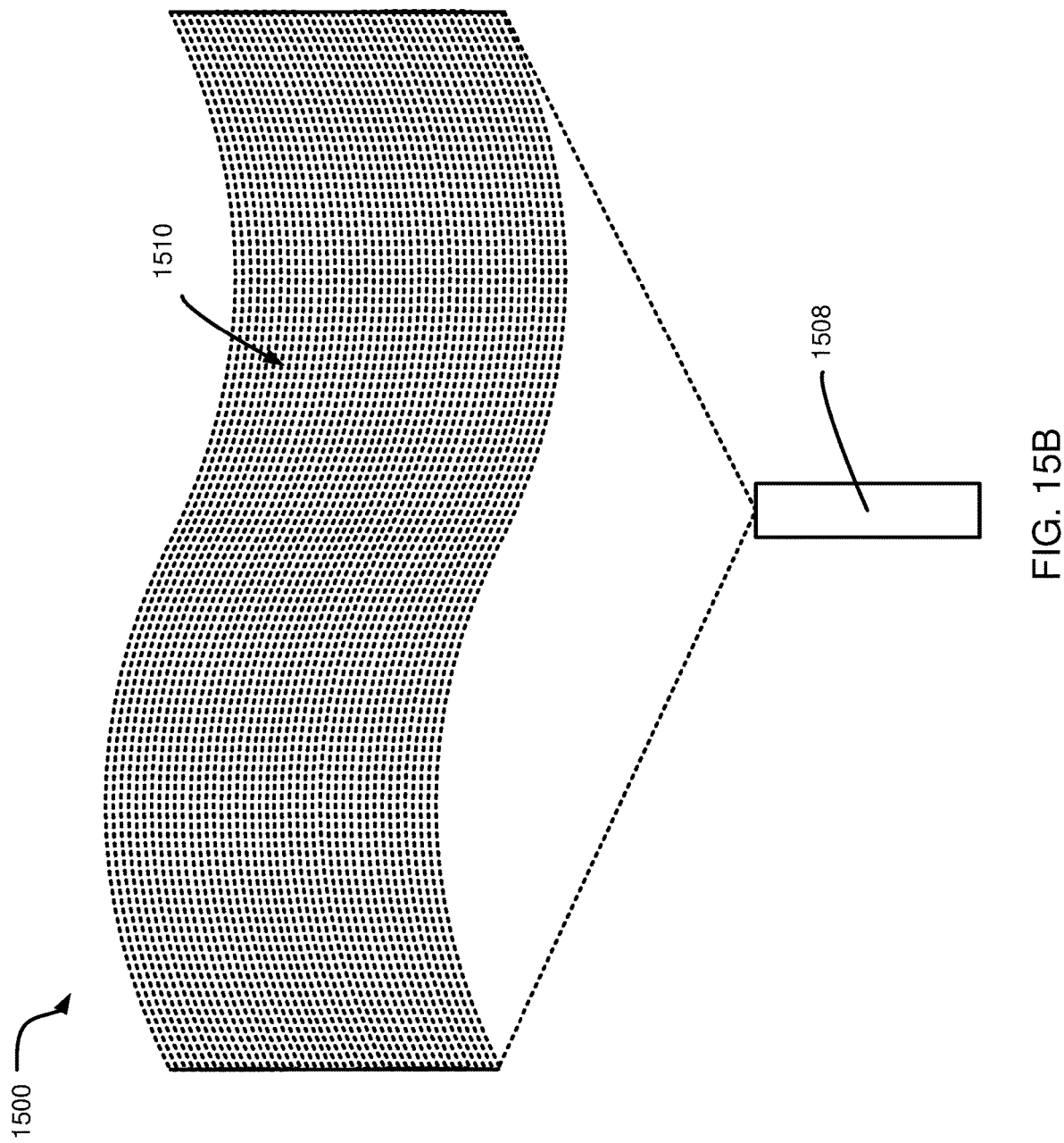

OPTICAL FILTER FOR IMPROVED MULTISPECTRAL IMAGING PERFORMANCE IN STEREO CAMERA

TECHNICAL FIELD

This disclosure is directed to advanced visualization and digital imaging systems and methods and, more particularly but not entirely, to efficient time multiplexing of different illumination sources.

BACKGROUND

Endoscopic surgical instruments are often preferred over traditional open surgical devices because the small incision tends to reduce post-operative recovery time and associated complications. In some instances of endoscopic visualization, it is desirable to view a space with high-definition color imaging and further with one or more advanced visualization techniques providing additional information that cannot be discerned with the human eye. However, the space constrained environment of an endoscope introduces numerous technical challenges when seeking to capture advanced visualization data in a light deficient environment.

There are numerous endoscopic visualization systems that seek to capture advanced visualization data, such as multispectral data, fluorescence data, and laser mapping data, while working within the space constrained environment of an endoscope. However, these endoscopic visualization systems do not implement two-sensor stereo visualization or fail to optimize the use of two sensors for capturing color imaging data and advanced imaging data.

Traditional stereo endoscopes require a tradeoff between image quality (resolution) and performance (speed, latency, and light collection). These traditional systems combine broadband white light for color visualization with narrowband light for advanced visualization, such as multispectral visualization or fluorescence visualization. The camera sensor speed is inversely related to the camera sensor resolution, such that high resolution is achieved with the use of a high pixel count, which generates a large amount of pixel data, but requires more time to transfer the data off the image sensor. The traditional stereo endoscopes can be operated in a full resolution mode or a binned lower-resolution mode. The full resolution mode is typically preferred for color visualization, while the binned lower-resolution mode is acceptable for advanced visualization. In the existing traditional stereo endoscopes, the system cannot simultaneously capture full resolution data and binned lower-resolution data because the design of the lens, optical filters, and image sensors and equivalent on both channels of the stereo camera.

For example, commonly owned U.S. Patent Application Publication No. 2020/0404131, entitled "HYPERSPECTRAL AND FLUORESCENCE IMAGING WITH TOPOLOGY LASER SCANNING IN A LIGHT DEFICIENT ENVIRONMENT," filed on Oct. 24, 2019, which is incorporated by reference in its entirety, describes an endoscopic visualization system for color and "specialty" imaging. In this disclosure, an emitter is configured to emit electromagnetic energy in wavelength bands within the visible spectrum, including red, green, and blue emissions, as well as specialty emissions, wherein the specialty emissions may include hyperspectral, fluorescence, or laser mapping emissions of electromagnetic energy. However, this disclosure does not indicate that the endoscope may be equipped with two or more image sensors for stereo visualization, wherein the two or more image sensors may be equipped with different lenses, optical filters, pixel filters, and so forth for optimizing different types of visualization.

Consequently, a significant need exists for a stereo endoscopic visualization system that can capture color, including high-definition color, multispectral, fluorescence, and laser mapping imaging data with sufficient resolution from frame-to-frame without sacrificing the image quality of an output color video stream.

In view of the foregoing, described herein are systems, methods, and devices for stereo visualization with optical filters for selective detection of color, multispectral, fluorescence, and laser mapping imaging data.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with regard to the following description and accompanying drawings where:

FIG. 14A is a schematic illustration of an example binning configuration for an image sensor comprising a color filter array;

FIG. 14B is a schematic illustration of an example binning configuration for an image sensor comprising a color filter array;

FIG. 15B is a schematic illustration of an example mapping pattern comprising a dot array;

DETAILED DESCRIPTION

Figure 1A:
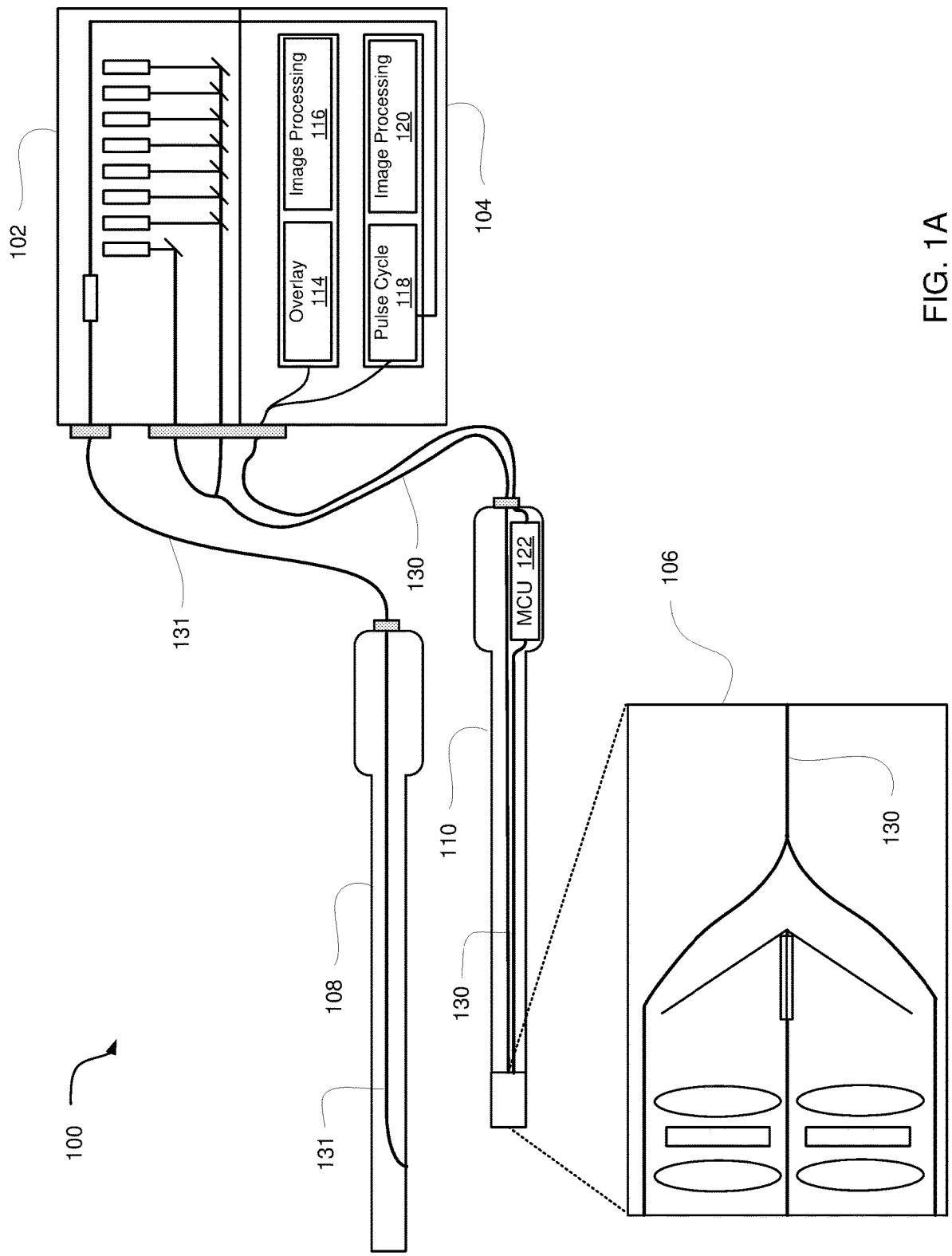
FIG. 1A is a schematic illustration of an example system for endoscopic visualization with color imaging and advanced imaging.

Disclosed herein are systems, methods, and devices for digital visualization that may be primarily suited to medical applications such as medical endoscopic imaging. An embodiment of the disclosure is an endoscopic system for color visualization and "advanced visualization" of a scene. The advanced visualization includes one or more of multispectral imaging, fluorescence imaging, or topographical mapping. Data retrieved from the advanced visualization may be processed by one or more algorithms configured to determine characteristics of the scene. The advanced visualization data may specifically be used to identify tissue structures within a scene, generate a three-dimensional topographical map of the scene, calculate dimensions of objects within the scene, identify margins and boundaries of different tissue types, and so forth.

The systems, methods, and devices described herein are specifically optimized for stereo endoscopic visualization of a scene. The systems described herein are capable of outputting a high-resolution color video stream and further outputting advanced visualization data with sufficient resolution for algorithmic processing. A stereo camera described herein may be fitted with different optical filters on the first channel (i.e., first image sensor) and the second channel (i.e., second image sensor). One channel may be optimized for color visualization and blocked from accumulating data outside the visible range of the electromagnetic spectrum. The other channel may be optimized for color visualization and further optimized for near infrared visualization that may be implemented for multispectral or fluorescence visualization. The sensor readout cycles for the first channel and the second channel may be optimized and adjusted on a frame-by-frame basis based on user input, frame resolution, proper exposure of the scene, and the type of visualization.

An embodiment of the disclosure is an endoscopic visualization system that includes an emitter, an image sensor, and a controller. The emitter includes a plurality of separate and independently actuatable sources of electromagnetic radiation ("EMR") that may be separately cycled on and off to illuminate a scene with pulses of EMR. The image sensor accumulates EMR and reads out data for generating a plurality of data frames. The controller synchronizes operations of the emitter and the image sensor to output a desired visualization scheme based on user input. The visualization scheme may include a selection of one or more of color imaging, multispectral imaging, fluorescence imaging, topographical mapping, or anatomical measurement.

The controller instructs the emitter and the image sensor to operate in a synchronized sequence to output a video stream that includes one or more types of visualization (i.e., color imaging, multispectral imaging, fluorescence imaging, topographical mapping, or anatomical measurement). The controller instructs the emitter to actuate one or more of the plurality of EMR sources to pulse according to a variable pulse cycle. The controller instructs the image sensor to accumulate EMR and read out data according to a variable sensor cycle that is synchronized in time with the variable pulse cycle. The synchronized sequence of the emitter and the image sensor enables the image sensor to read out data corresponding with a plurality of different visualization types. For example, the image sensor may read out a color frame in response to the emitter pulsing a white light or other visible EMR, the image sensor may readout a multispectral frame in response to the emitter pulsing a multispectral waveband of EMR, the image sensor may read out data for calculating a three-dimensional topographical map in response to the emitter pulsing EMR in a mapping pattern, and so forth.

The controller optimizes and adjusts a sensor cycle of an image sensor to output data frames for color imaging and/or advanced imaging at a sufficient rate, while ensuring the pixel array accumulates a sufficient amount of EMR for each data frame. The controller may instruct the image sensor to implement pixel binning on a per-frame basis, such that the image sensor implements pixel binning for some data frames and reads out all pixels for other data frames. In some cases, the controller instructs the image sensor to read out all pixels and thereby output a high-definition color data frame in response to the emitter pulsing white EMR. The controller may further instruct the image sensor to bin the pixel array and read out fewer pixels in response to the emitter pulsing EMR for advanced visualization, such as multispectral imaging, fluorescence imaging, or topographical mapping.

The controller may additionally optimize and adjust the variable pulse cycle in real-time based on user input, sufficient exposure of resultant data frames, and inherent properties of a corresponding pixel array. In some cases, a pixel array has varying sensitivities to different wavebands of EMR. In these cases, the pixel array is irradiated with EMR for shorter or longer durations of time depending on the type of illumination pulse to ensure the pixel array outputs data frames with consistent exposure levels. The controller adjusts the irradiation time of the pixel array and the pulsing duration of the emitter in real-time to compensate for the pixel array's varying efficiencies to different types of illumination.

The systems, methods, and devices described herein are implemented for color visualization and advanced visualization. The advanced visualization techniques described herein can be used to identify certain tissues, see through tissues in the foreground, calculate a three-dimensional topography of a scene, and calculate dimensions and distances for objects within the scene. The advanced visualization techniques described herein specifically include multispectral visualization, fluorescence visualization, and laser mapping visualization.

Multispectral Visualization

Spectral imaging uses multiple bands across the electromagnetic spectrum. This is different from conventional cameras that only capture light across the three wavelengths based in the visible spectrum that are discernable by the human eye, including the red, green, and blue wavelengths to generate an RGB image. Spectral imaging may use any wavelength bands in the electromagnetic spectrum, including infrared wavelengths, the visible spectrum, the ultraviolet spectrum, x-ray wavelengths, or any suitable combination of various wavelength bands. Spectral imaging may overlay imaging generated based on non-visible bands (e.g., infrared) on top of imaging based on visible bands (e.g., a standard RGB image) to provide additional information that is easily discernable by a person or computer algorithm.

The multispectral imaging techniques discussed herein can be used to "see through" layers of tissue in the foreground of a scene to identify specific types of tissue and/or specific biological or chemical processes. Multispectral imaging can be used in the medical context to quantitatively track the process of a disease and to determine tissue pathology. Additionally, multispectral imaging can be used to identify critical structures such as nerve tissue, muscle tissue, cancerous cells, blood vessels, and so forth. In an embodiment, multispectral partitions of EMR are pulsed and data is gathered regarding the spectral responses of different types of tissue in response to the partitions of EMR. A datastore of spectral responses can be generated and analyzed to assess a scene and predict which tissues are present within the scene based on the sensed spectral responses.

Multispectral imaging enables numerous advantages over conventional imaging. The information obtained by multispectral imaging enables medical practitioners and/or computer-implemented programs to precisely identify certain tissues or conditions that may not be possible to identify with RGB imaging. Additionally, multispectral imaging may be used during medical procedures to provide image-guided surgery that enables a medical practitioner to, for example, view tissues located behind certain tissues or fluids, identify atypical cancerous cells in contrast with typical healthy cells, identify certain tissues or conditions, identify critical structures, and so forth. Multispectral imaging provides specialized diagnostic information about tissue physiology, morphology, and composition that cannot be generated with conventional imaging.

Fluorescence Visualization

Fluorescence occurs when an orbital electron of a molecule, atom, or nanostructure is excited by light or other EMR, and then relaxes to its ground state by emitting a photon from the excited state. The specific frequencies of EMR that excite the orbital electron, or are emitted by the photon during relaxation, are dependent on the particular atom, molecule, or nanostructure. In most cases, the light emitted by the substance has a longer wavelength, and therefore lower energy, than the radiation that was absorbed by the substance.

Fluorescence imaging is particularly useful in biochemistry and medicine as a non-destructive means for tracking or analyzing biological molecules. The biological molecules, including certain tissues or structures, are tracked by analyzing the fluorescent emission of the biological molecules after being excited by a certain wavelength of EMR. However, relatively few cellular components are naturally fluorescent. In certain implementations, it may be desirable to visualize a certain tissue, structure, chemical process, or biological process that is not intrinsically fluorescent. In such an implementation, the body may be administered a dye or reagent that may include a molecule, protein, or quantum dot having fluorescent properties. The reagent or dye may then fluoresce after being excited by a certain wavelength of EMR. Different reagents or dyes may include different molecules, proteins, and/or quantum dots that will fluoresce at particular wavelengths of EMR. Thus, it may be necessary to excite the reagent or dye with a specialized band of EMR to achieve fluorescence and identify the desired tissue, structure, or process in the body.

The fluorescence imaging techniques described herein may be used to identify certain materials, tissues, components, or processes within a body cavity or other light deficient environment. Fluorescence imaging data may be provided to a medical practitioner or computer-implemented algorithm to enable the identification of certain structures or tissues within a body. Such fluorescence imaging data may be overlaid on black-and-white or RGB images to provide additional information and context.

The fluorescence imaging techniques described herein may be implemented in coordination with fluorescent reagents or dyes. Some reagents or dyes are known to attach to certain types of tissues and fluoresce at specific wavelengths of the electromagnetic spectrum. In an implementation, a reagent or dye is administered to a patient that is configured to fluoresce when activated by certain wavelengths of light. The visualization system disclosed herein is used to excite and fluoresce the reagent or dye. The fluorescence of the reagent or dye is detected by an image sensor to aid in the identification of tissues or structures in the body cavity. In an implementation, a patient is administered a plurality of reagents or dyes that are each configured to fluoresce at different wavelengths and/or provide an indication of different structures, tissues, chemical reactions, biological processes, and so forth. In such an implementation, the visualization system described herein emits each of the applicable wavelengths to fluoresce each of the applicable reagents or dyes. This may negate the need to perform individual imaging procedures for each of the plurality of reagents or dyes.

Laser Mapping Visualization

Laser mapping generally includes the controlled deflection of laser beams. Laser mapping can be implemented to generate one or more of a three-dimensional topographical map of a scene, calculate distances between objects within the scene, calculate dimensions of objects within the scene, track the relative locations of tools within the scene, and so forth.

Laser mapping combines controlled steering of laser beams with a laser rangefinder. By taking a distance measurement at every direction, the laser rangefinder can rapidly capture the surface shape of objects, tools, and landscapes. Construction of a full three-dimensional topography may include combining multiple surface models that are obtained from different viewing angles. Various measurement systems and methods exist in the art for applications in archaeology, geography, atmospheric physics, autonomous vehicles, and others. One such system includes light detection and ranging (LIDAR), which is a three-dimensional mapping system. LIDAR has been applied in navigation systems such as airplanes or satellites to determine position and orientation of a sensor in combination with other systems and sensors. LIDAR uses active sensors to illuminate an object and detect energy that is reflected off the object and back to a sensor.

As discussed herein, the term "laser mapping" includes laser tracking. Laser tracking, or the use of lasers for tool tracking, measures objects by determining the positions of optical targets held against those objects. Laser trackers can be accurate to the order of 0.025 mm over a distance of several meters. The visualization system described herein pulses EMR for use in conjunction with a laser tracking system such that the position of tools within a scene can be tracked and measured.

The endoscopic visualization system described herein implements laser mapping imaging to determine precise measurements and topographical outlines of a scene. In one implementation, mapping data is used to determine precise measurements between, for example, structures or organs in a body cavity, devices, or tools in the body cavity, and/or critical structures in the body cavity. As discussed herein, the term "mapping" encompasses technologies referred to as laser mapping, laser scanning, topographical scanning, three-dimensional scanning, laser tracking, tool tracking, and others. A mapping data frame as discussed herein includes data for calculating one or more of a topographical map of a scene, dimensions of objects or structures within a scene, distances between objects or structures within the scene, relative locations of tools or other objects within the scene, and so forth.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the structure, systems, and methods are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

As used herein, the term "proximal" shall refer broadly to the concept of a portion nearest an origin.

As used herein, the term "distal" shall generally refer to the opposite of proximal, and thus to the concept of a portion farther from an origin, or a farthest portion, depending upon the context.

As used herein, color sensors are sensors known to have a color filter array (CFA) thereon to filter the incoming EMR into its separate components. In the visual range of the electromagnetic spectrum, such a CFA may be built on a Bayer pattern or modification thereon to separate green, red, and blue spectrum components of visible EMR.

As used herein, a monochromatic sensor refers to an unfiltered imaging sensor comprising color-agnostic pixels.

The systems, methods, and devices described herein are specifically optimized to account for variations between "stronger" electromagnetic radiation (EMR) sources and "weaker" EMR sources. In some cases, the stronger EMR sources are considered "stronger" based on the inherent qualities of a pixel array, e.g., if a pixel array is inherently more sensitive to detecting EMR emitted by the stronger EMR source, then the stronger EMR source may be classified as "stronger" when compared with another EMR source. Conversely, if the pixel array is inherently less sensitive to detecting EMR emitted by the weaker EMR source, then the weaker EMR source may be classified as "weaker" when compared with another EMR source. Additionally, a "stronger" EMR source may have a higher amplitude, greater brightness, or higher energy output when compared with a "weaker" EMR source. The present disclosure addresses the disparity between stronger EMR sources and weaker EMR sources by adjusting a pulse cycle of an emitter to ensure a pixel array has sufficient time to accumulate a sufficient amount of EMR corresponding with each of a stronger EMR source and a weaker EMR source.

Figure 1B:
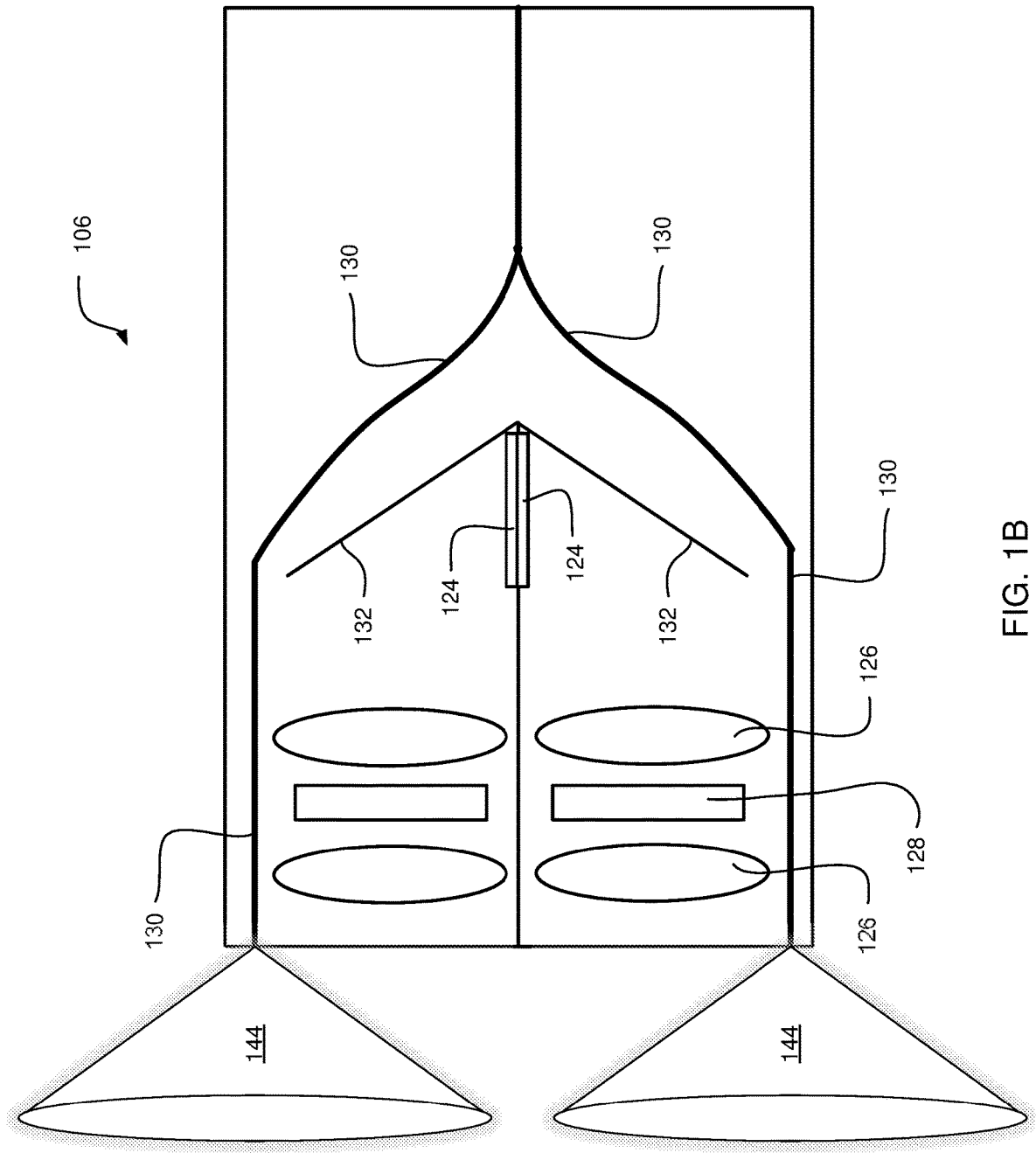
FIG. 1B is a schematic illustration of an example image pickup portion of a system for endoscopic visualization with color imaging and advanced imaging
Figure 1C:
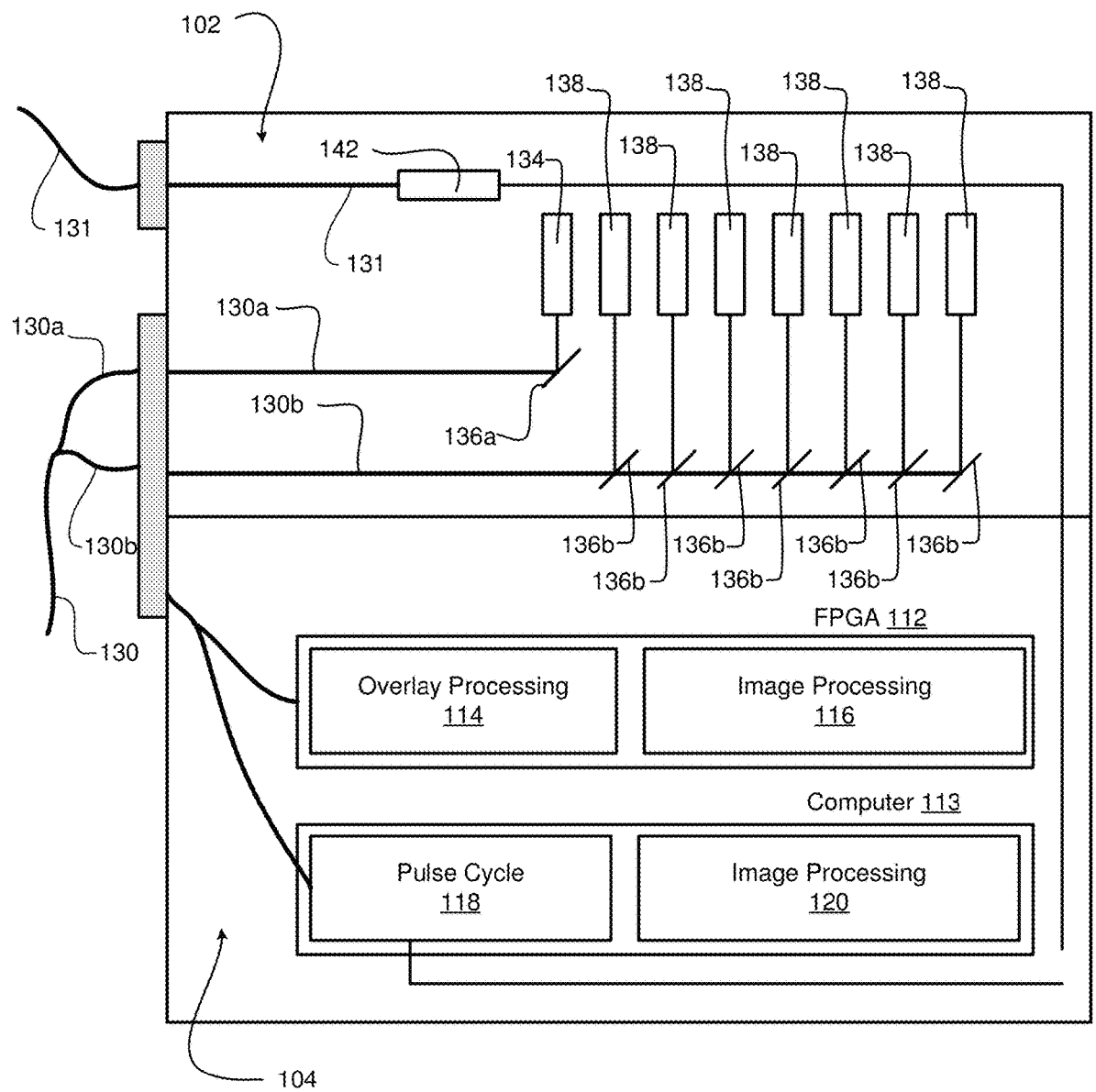
FIG. 1C is a schematic illustration of an example emitter and controller of a system for endoscopic visualization with color imaging and advanced imaging.

Referring now to the figures, FIGS. 1A-1C illustrate schematic diagrams of a system 100 for endoscopic visualization. The system 100 includes an emitter 102, a controller 104, and an optical visualization system 106. The system 100 includes one or more tools 108, which may include endoscopic tools such as forceps, brushes, scissors, cutters, burs, staplers, ligation devices, tissue staplers, suturing systems, and so forth. The system 100 includes one or more endoscopes 110 such as arthroscopes, bronchoscopes, colonoscopes, colposcopes, cystoscopes, esophagoscope, gastroscopes, laparoscopes, laryngoscopes, neuroendoscopes, proctoscopes, sigmoidoscopes, thoracoscopes, and so forth.

The optical visualization system 106 may be disposed at a distal end of a lumen of an endoscope 110. Alternatively, one or more components of the optical visualization system 106 may be disposed at a proximal end of the lumen of the endoscope 110 or in another region of the endoscope 110. The optical visualization system 106 may include one or more image sensors 124 that each include a pixel array (see pixel array 125 first illustrated in FIG. 2A). The optical visualization system 106 may include one or more lenses 126 and filters 128 and may further include one or more prisms 132 for reflecting EMR on to the pixel array 125 of the one or more image sensors 124. The system 100 may include a waveguide 130 configured to transmit EMR from the emitter 102 to a distal end of the endoscope 110 to illuminate a light deficient environment for visualization. The system 100 may further include a waveguide 131 configured to transmit EMR from the emitter 102 to a termination point on the tool 108, which may specifically be actuated for laser mapping imaging and tool tracking as described herein.

The optical visualization system 106 may specifically include two lenses 126 dedicated to each image sensor 124 to focus EMR on to a rotated image sensor 124 and enable a depth view. The filter 128 may include a notch filter configured to block unwanted reflected EMR. In a particular use-case, the unwanted reflected EMR may include a fluorescence excitation wavelength that was pulsed by the emitter 102, wherein the system 100 wishes to only detect a fluorescence relaxation wavelength emitted by a fluorescent reagent or tissue.

The image sensor 124 includes one or more image sensors, and the example implementation illustrated in FIGS. 1A-1B illustrates an optical visualization system 106 comprising two image sensors 124. The image sensor 124 may include a CMOS image sensor and may specifically include a high-resolution image sensor configured to read out data according to a rolling readout scheme. The image sensors 124 may include a plurality of different image sensors that are tuned to collect different wavebands of EMR with varying efficiencies. In an implementations, the image sensors 124 include separate image sensors that are optimized for color imaging, fluorescence imaging, multispectral imaging, and/or topographical mapping.

The emitter 102 includes one or more EMR sources, which may include, for example, lasers, laser bundles, light emitting diodes (LEDs), electric discharge sources, incandescence sources, electroluminescence sources, and so forth. In some implementations, the emitter 102 includes at least one white EMR source 134 (may be referred to herein as a white light source). The emitter 102 may additionally include one or more EMR sources 138 that are tuned to emit a certain waveband of EMR. The EMR sources 138 may specifically be tuned to emit a waveband of EMR that is selected for multispectral or fluorescence visualization. The emitter 102 may additionally include one or more mapping sources 142 that are configured to emit EMR in a mapping pattern such as a grid array or dot array selected for capturing data for topographical mapping or anatomical measurement.

The one or more white EMR sources 134 emit EMR into a dichroic mirror 136a that feeds the white EMR into a waveguide 130. The white EMR source 134 may specifically feed into a first waveguide 130a dedicated to white EMR. The EMR sources 138 emit EMR into independent dichroic mirrors 136b that each feed EMR into the waveguide 130 and may specifically feed into a second waveguide 130b. The first waveguide 130a and the second waveguide 130b later merge into a waveguide 130 that transmits EMR to a distal end of the endoscope 110 to illuminate a scene with an emission of EMR 144.

The one or more EMR sources 138 that are tuned to emit a waveband of EMR may specifically be tuned to emit EMR that is selected for multispectral or fluorescence visualization. In some cases, the EMR sources 138 are finely tuned to emit a central wavelength of EMR with a tolerance threshold not exceeding±5 nm, ±4 nm, ±3 nm, ±2 nm, or ±1 nm. The EMR sources 138 may include lasers or laser bundles that are separately cycled on and off by the emitter 102 to pulse the emission of EMR 144 and illuminate a scene with a finely tuned waveband of EMR.

The one or more mapping sources 142 are configured to pulse EMR in a mapping pattern, which may include a dot array, grid array, vertical hashing, horizontal hashing, pin grid array, and so forth. The mapping pattern is selected for laser mapping imaging to determine one or more of a three-dimensional topographical map of a scene, a distance between two or more objects within a scene, a dimension of an object within a scene, a location of a tool 108 within the scene, and so forth. The EMR pulsed by the mapping source 142 is diffracted to spread the energy waves according to the desired mapping pattern. The mapping source 142 may specifically include a device that splits the EMR beam with quantum-dot-array diffraction grafting. The mapping source 142 may be configured to emit low mode laser light.

The controller 104 (may be referred to herein as a camera control unit or CCU) may include a field programmable gate array (FGPA) 112 and a computer 113. The FGPA 112 may be configured to perform overlay processing 114 and image processing 116. The computer 113 may be configured to generate a pulse cycle 118 for the emitter 102 and to perform further image processing 120. The FGPA 112 receives data from the image sensor 124 and may combine data from two or more data frames by way of overlay processing 114 to output an overlay image frame. The computer 113 may provide data to the emitter 102 and the image sensor 124. Specifically, the computer 113 may calculate and adjust a variable pulse cycle to be emitted by the emitter 102 in real-time based on user input. Additionally, the computer 113 may receive data frames from the image sensor 124 and perform further image processing 120 on those data frames.

The controller 104 may be in communication with a network, such as the Internet, and automatically upload data to the network for remote storage. The MCU 122 and image sensors 124 maybe exchanged and updated and continue to communicate with an established controller 104. In some cases, the controller 104 is "out of date" with respect to the MCU 122 but will still successfully communicate with the MCU 122. This may increase the data security for a hospital or other healthcare facility because the existing controller 104 may be configured to undergo extensive security protocols to protect patient data.

The controller 104 may reprogram the image sensor 124 for each data frame to set a required blanking period duration and/or readout period duration for a subsequent frame period. One frame period includes a blanking period and a readout period. Generally speaking, the pixel array 125 accumulates EMR during the blanking period and reads out pixel data during the readout period. It will be understood that a blanking period corresponds to a time between a readout of a last row of active pixels in the pixel array of the image sensor and a beginning of a next subsequent readout of active pixels in the pixel array. Additionally, the readout period corresponds to a duration of time when active pixels in the pixel array are being read. Further, the controller 104 may write correct registers to the image sensor 124 to adjust the duration of one or more of the blanking period or the readout period for each frame period on a frame-by-frame basis within the sensor cycle as needed.

The endoscope 110 includes a microcontroller unit (MCU) 122 disposed therein. The MCU 122 may specifically be disposed within a handpiece portion of the endoscope 110 and communicate with electronic circuitry (such as the image sensor 124) disposed within a distal end of a lumen of the endoscope 110. The MCU 122 receives instructions from the controller 104, including an indication of the pulse cycle 118 provided to the emitter 102 and the corresponding sensor cycle timing for the image sensor 124. The MCU 122 executes a common Application Program Interface (API). The controller 104 communicates with the MCU 122, and the MCU 122 executes a translation function that translates instructions received from the controller 104 into the correct format for each type of image sensor 124. In some cases, the system 100 may include multiple different image sensors that each operate according to a different "language" or formatting, and the MCU 122 is configured to translate instructions from the controller 104 into each of the appropriate data formatting languages. The common API on the MCU 122 passes information by the scene, including, for example parameters pertaining to gain, exposure, white balance, setpoint, and so forth. The MCU 122 runs a feedback algorithm to the controller 104 for any number of parameters depending on the type of visualization.

The MCU 122 stores operational data and images captured by the image sensors 124. In some cases, the MCU 122 does not need to continuously push data up the data chain to the controller 104. The data may be set once on the microcontroller 122, and then only critical information may be pushed through a feedback loop to the controller 104. The MCU 122 may be set up in multiple modes, including a primary mode (may be referred to as a "master" mode when referring to a master/slave communication protocol). The MCU 122 ensures that all downstream components (i.e., distal components including the image sensors 124, which may be referred to as "slaves" in the master/slave communication protocol) are apprised of the configurations for upcoming data frames. The upcoming configurations may include, for example, gain, exposure duration, readout duration, pixel binning configuration, and so forth.

The MCU 122 includes internal logic for executing triggers to coordinate different devices, including, for example multiple image sensors 124. The MCU 122 provides instructions for upcoming frames and executes triggers to ensure that each image sensor 124 begins to capture data the same time. In some cases, the image sensors 124 may automatically advance to a subsequent data frame without receiving a unique trigger from the MCU 122.

In some cases, the endoscope 110 includes two or more image sensors 124 that detect EMR and output data frames simultaneously. The simultaneous data frames may be used to output a three-dimensional image and/or output imagery with increased definition and dynamic range. The pixel array of the image sensor 124 may include active pixels and optical black ("OB") or optically blind pixels. The optical black pixels may be read during a blanking period of the pixel array when the pixel array is "reset" or calibrated. After the optical black pixels have been read, the active pixels are read during a readout period of the pixel array. The active pixels accumulate EMR that is pulsed by the emitter 102 during the blanking period of the image sensor 124. The pixel array 125 may include monochromatic or "color agnostic" pixels that do not comprise any filter for selectively receiving certain wavebands of EMR. The pixel array may include a color filter array (CFA), such as a Bayer pattern CFA, that selectively allows certain wavebands of EMR to pass through the filters and be accumulated by the pixel array.

The image sensor 124 is instructed by a combination of the MCU 122 and the controller 104 working in a coordinated effort. Ultimately, the MCU 122 provides the image sensor 124 with instructions on how to capture the upcoming data frame. These instructions include, for example, an indication of the gain, exposure, white balance, exposure duration, readout duration, pixel binning configuration, and so forth for the upcoming data frame. When the image sensor 124 is reading out data for a current data frame, the MCU 122 is rewriting the correct registers for the next data frame. The MCU 122 and the image sensor 124 operate in a back-and-forth data flow, wherein the image sensor 124 provides data to the MCU 122 and the MCU 122 rewrites correct registers to the image sensor 124 for each upcoming data frame. The MCU 122 and the image sensor 124 may operate according to a "ping pong buffer" in some configurations.

The image sensor 124, MCU 122, and controller 104 engage in a feedback loop to continuously adjust and optimize configurations for upcoming data frames based on output data. The MCU 122 continually rewrites correct registers to the image sensor 124 depending on the type of upcoming data frame (i.e., color data frame, multispectral data frame, fluorescence data frame, topographical mapping data frame, and so forth), configurations for previously output data frames, and user input. In an example implementation, the image sensor 124 outputs a multispectral data frame in response to the emitter 102 pulsing a multispectral waveband of EMR. The MCU 122 and/or controller 104 determines that the multispectral data frame is underexposed and cannot successfully be analyzed by a corresponding machine learning algorithm. The MCU 122 and/or controller 104 than adjusts configurations for upcoming multispectral data frames to ensure that future multispectral data frames are properly exposed. The MCU 122 and/or controller 104 may indicate that the gain, exposure duration, pixel binning configuration, etc. must be adjusted for future multispectral data frames to ensure proper exposure. All image sensor 124 configurations may be adjusted in real-time based on previously output data processed through the feedback loop, and further based on user input.

The waveguides 130, 131 include one or more optical fibers. The optical fibers may be made of a low-cost material, such as plastic to allow for disposal of one or more of the waveguides 130, 131. In some implementations, one or more of the waveguides 130, 131 include a single glass fiber having a diameter of 500 microns. In some implementations, one or more of the waveguides 130, 131 include a plurality of glass fibers.

Figure 2A:
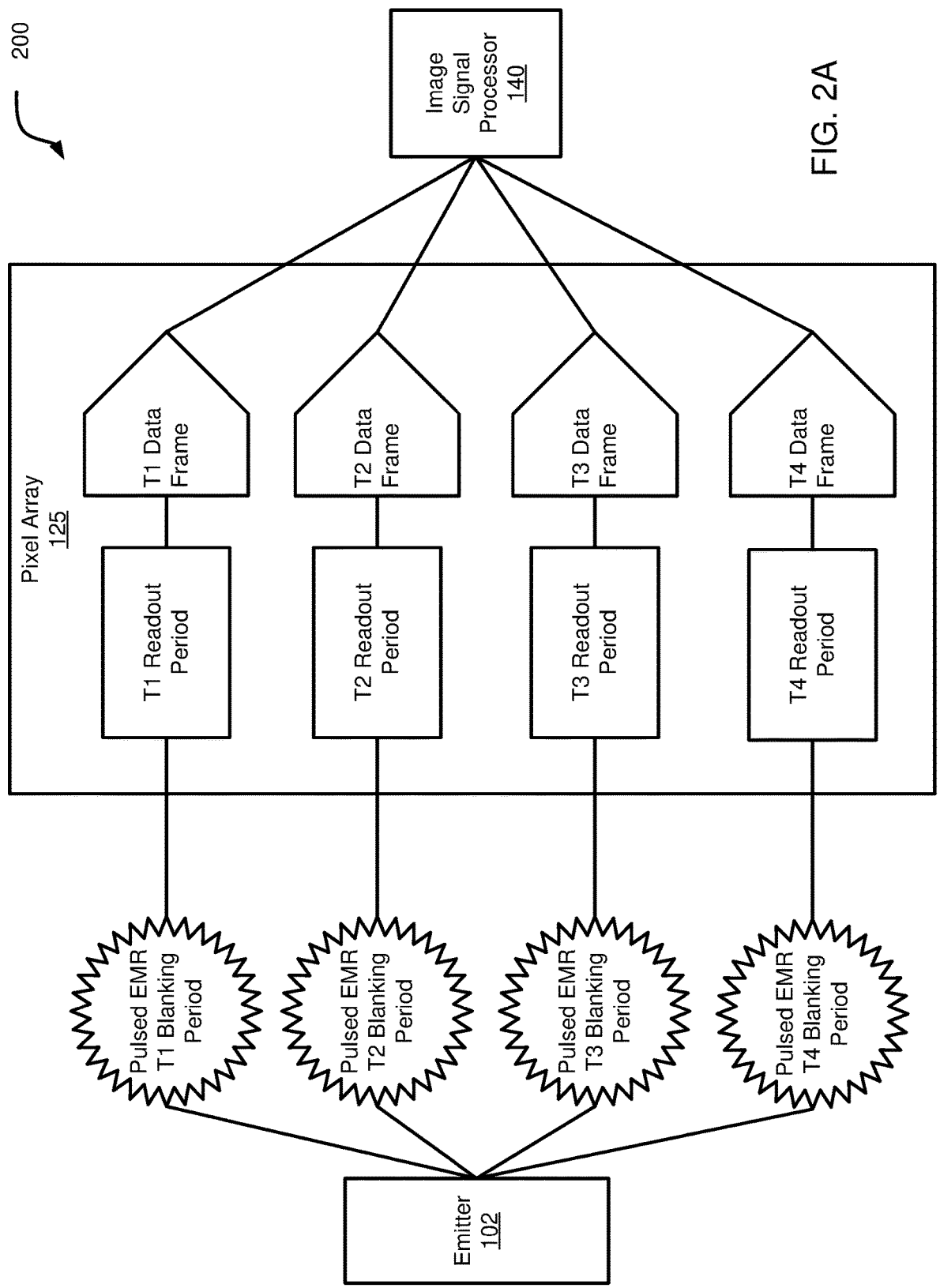
FIG. 2A is a schematic block diagram of an example data flow for a time-sequenced visualization system.
Figure 2B:
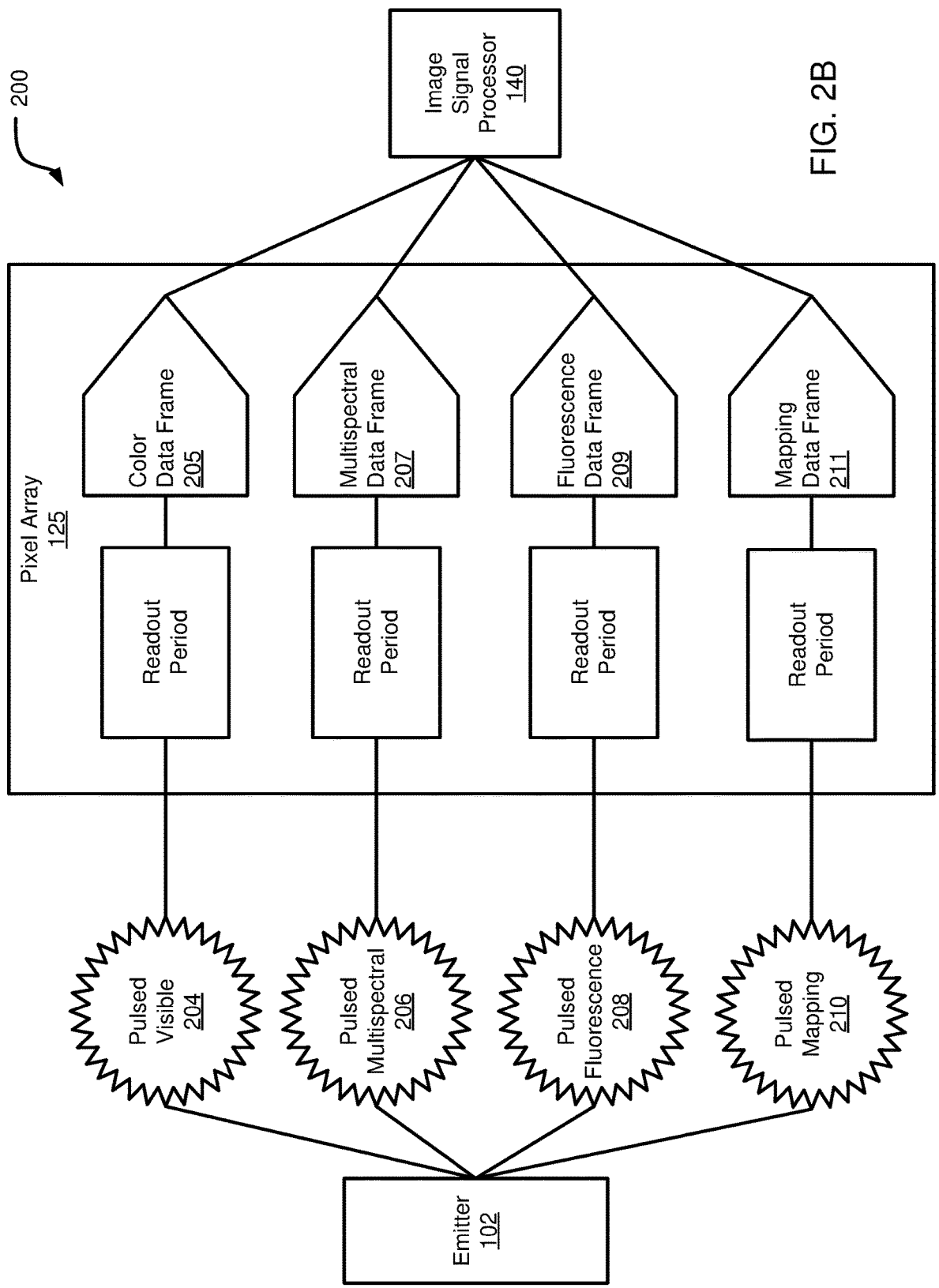
FIG. 2B is a schematic block diagram of an example data flow for a time-sequenced visualization system.

FIGS. 2A and 2B each illustrate a schematic diagram of a data flow 200 for time-sequenced visualization of a light deficient environment. The data flow 200 illustrated in FIGS. 2A-2B may be implemented by the system 100 for endoscopic visualization illustrated in FIGS. 1A-1C. FIG. 2A illustrates a generic implementation that may be applied to any type of illumination or wavelengths of EMR. FIG. 2B illustrates an example implementation wherein the emitter 102 actuates visible, multispectral, fluorescence, and mapping EMR sources.

The data flow 200 includes an emitter 102, a pixel array 125 of an image sensor 124 (not shown), and an image signal processor 140. The image signal processor 140 may include one or more of the image processing 116, 120 modules illustrated in FIGS. 1A and 1C. The emitter 102 includes a plurality of separate and independently actuatable EMR sources (see, e.g., 134, 138 illustrated in FIGS. 1A and 1C). Each of the EMR sources can be cycled on and off to emit a pulse of EMR with a defined duration and magnitude. The pixel array 125 of the image sensor 124 may include a color filter array (CFA) or an unfiltered array comprising color-agnostic pixels. The emitter 102 and the pixel array 125 are each in communication with a controller 104 (not shown in FIGS. 2A-2B) that instructs the emitter 102 and the pixel array 125 to synchronize operations to generate a plurality of data frames according to a desired visualization scheme.

The controller 104 instructs the emitter 102 to cycle the plurality of EMR sources according to a variable pulse cycle. The controller 104 calculates the variable pulse cycle based at least in part upon a user input indicating the desired visualization scheme. For example, the desired visualization scheme may indicate the user wishes to view a scene with only color imaging. In this case, the variable pulse cycle may include only pulses of white EMR. In an alternative example, the desired visualization scheme may indicate the user wishes to be notified when nerve tissue can be identified in the scene and/or when a tool within the scene is within a threshold distance from the nerve tissue. In this example, the variable pulse cycle may include pulses of white EMR and may further include pulses of one or more multispectral wavebands of EMR that elicit a spectral response from the nerve tissue and/or "see through" non-nerve tissues by penetrating those non-nerve tissues. Additionally, the variable pulse cycle may include pulses of EMR in a mapping pattern configured for laser mapping imaging to determine when the tool is within the threshold distance from the nerve tissue. The controller 104 may reconfigure the variable pulse cycle in real-time in response to receiving a revised desired visualization scheme from the user.

FIGS. 2A and 2B each illustrate a schematic diagram of a data flow 200 for time-sequenced visualization of a light deficient environment. The data flow 200 illustrated in FIGS. 2A-2B may be implemented by the system 100 for endoscopic visualization illustrated in FIGS. 1A-1C. FIG. 2A illustrates a generic implementation that may be applied to any type of illumination or wavelengths of EMR. FIG. 2B illustrates an example implementation wherein the emitter 102 actuates visible, multispectral, fluorescence, and mapping EMR sources.

The data flow 200 includes an emitter 102, a pixel array 125 of an image sensor 124 (not shown), and an image signal processor 140. The image signal processor 140 may include one or more of the image processing 116, 120 modules illustrated in FIGS. 1A and 1C. The emitter 102 includes a plurality of separate and independently actuatable EMR sources (see, e.g., 134, 138 illustrated in FIGS. 1A and 1C). Each of the EMR sources can be cycled on and off to emit a pulse of EMR with a defined duration and magnitude. The pixel array 125 of the image sensor 124 may include a color filter array (CFA) or an unfiltered array comprising color-agnostic pixels. The emitter 102 and the pixel array 125 are each in communication with a controller 104 (not shown in FIGS. 2A-2B) that instructs the emitter 102 and the pixel array 125 to synchronize operations to generate a plurality of data frames according to a desired visualization scheme.

The controller 104 instructs the emitter 102 to cycle the plurality of EMR sources according to a variable pulse cycle. The controller 104 calculates the variable pulse cycle based at least in part upon a user input indicating the desired visualization scheme. For example, the desired visualization scheme may indicate the user wishes to view a scene with only color imaging. In this case, the variable pulse cycle may include only pulses of broad spectrum visible EMR. In an alternative example, the desired visualization scheme may indicate the user wishes to be notified when nerve tissue can be identified in the scene and/or when a tool within the scene is within a threshold distance from the nerve tissue. In this example, the variable pulse cycle may include pulses of white EMR and may further include pulses of one or more multispectral wavebands of EMR that elicit a spectral response from the nerve tissue and/or "see through" non-nerve tissues by penetrating those non-nerve tissues. Additionally, the variable pulse cycle may include pulses of EMR in a mapping pattern configured for laser mapping imaging to determine when the tool is within the threshold distance from the nerve tissue. The controller 104 may reconfigure the variable pulse cycle in real-time in response to receiving a revised desired visualization scheme from the user.

FIG. 2A illustrates wherein the emitter cycles one or more EMR sources on and off to emit a pulse of EMR during each of a plurality of separate blanking periods of the pixel array 125. Specifically, the emitter 102 emits pulsed EMR during each of a T1 blanking period, T2 blanking period, T3 blanking period, and T4 blanking period of the pixel array 125. The pixel array 125 accumulates EMR during its blanking periods and reads out data during its readout periods.

Specifically, the pixel array 125 accumulates EMR during the T1 blanking period and reads out the T1 data frame during the T1 readout period, which follows the T1 blanking period. Similarly, the pixel array 125 accumulates EMR during the T2 blanking period and reads out the T2 data frame during the T2 readout period, which follows the T2 blanking period. The pixel array 125 accumulates EMR during the T3 blanking period and reads out the T3 data frame during the T3 readout period, which follows the T3 blanking period. The pixel array 125 accumulates EMR during the T4 blanking period and reads out the T4 data frame during the T4 readout period, which follows the T4 blanking period. Each of the T1 data frame, the T2 data frame, the T3 data frame, and the T4 data frame is provided to the image signal processor 140.

The contents of each of the T1-T4 data frames is dependent on the type of EMR that was pulsed by the emitter 102 during the preceding blanking period. For example, if the emitter 102 pulses white light during the preceding blanking period, then the resultant data frame may include a color data frame (if the pixel array 125 includes a color filter array for outputting red, green, and blue image data). Further for example, if the emitter 102 pulses a multispectral waveband of EMR during the preceding blanking period, then the resultant data frame is a multispectral data frame comprising information for identifying a spectral response by one or more objects within the scene and/or information for "seeing through" one or more structures within the scene. Further for example, if the emitter 102 pulses a fluorescence excitation waveband of EMR during the preceding blanking period, then the resultant data frame is a fluorescence data frame comprising information for identifying a fluorescent reagent or autofluorescence response by a tissue within the scene. Further for example, if the emitter 102 pulses EMR in a mapping pattern during the preceding blanking period, then the resultant data frame is a mapping data frame comprising information for calculating one or more of a three-dimensional topographical map of the scene, a dimension of one or more objects within the scene, a distance between two or more objects within the scene, and so forth.

Some "machine vision" or "computer vision" data frames, including multispectral data frames, fluorescence data frames, and mapping data frames may be provided to a corresponding algorithm or neural network configured to evaluate the information therein. A multispectral algorithm may be configured to identify one or more tissue structures within a scene based on how those tissue structures respond to one or more different wavebands of EMR selected for multispectral imaging. A fluorescence algorithm may be configured to identify a location of a fluorescent reagent or auto-fluorescing tissue structure within a scene. A mapping algorithm may be configured to calculate one or more of a three-dimensional topographical map of a scene, a depth map, a dimension of one or more objects within the scene, and/or a distance between two or more objects within the scene based on the mapping data frame.

FIG. 2B illustrates an example wherein the emitter 102 cycles separate visible, multispectral, fluorescence, and mapping EMR sources to emit pulsed visible 204, pulsed multispectral 206, pulsed fluorescence 208, and pulsed EMR in a mapping pattern 210. It should be appreciated that FIG. 2B is illustrative only, and that the emissions 204, 206, 208, 210 may be emitted in any order, may be emitted during a single visualization session as shown in FIG. 2B, and may be emitted during separate visualization sessions.

The pixel array 125 reads out a color data frame 205 in response to the emitter 102 pulsing the pulsed visible 204 EMR. The pulsed visible 204 EMR may specifically include a pulse of white light. The pixel array 125 reads out a multispectral data frame 207 in response to the emitter 102 pulsing the multispectral 206 waveband of EMR. The pulsed multispectral 206 waveband of EMR may specifically include one or more of EMR within a waveband from about 513-545 nanometers (nm), 565-585 nm, 770-790 nm, and/or 900-1000 nm. It will be appreciated that the pulsed multispectral 206 waveband of EMR may include various other wavebands used to elicit a spectral response. The pixel array 125 reads out a fluorescence data frame 209 in response to the emitter 102 pulsing the fluorescence 208 waveband of EMR. The pulsed fluorescence 208 waveband of EMR may specifically include one or more of EMR within a waveband from about 770-795 nm and/or 790-815 nm. The pixel array 125 reads out a mapping data frame 211 in response to the emitter 102 pulsing EMR in a mapping pattern 210. The pulsed mapping pattern 210 may include one or more of vertical hashing, horizontal hashing, a pin grid array, a dot array, a raster grid of discrete points, and so forth. Each of the color data frame 205, the multispectral data frame 207, the fluorescence data frame 209, and the mapping data frame 211 is provided to the image signal processor 140.

In an implementation, the emitter 102 separately pulses red, green, and blue visible EMR. In this implementation, the pixel array 125 may include a monochromatic (color agnostic) array of pixels. The pixel array 125 may separately read out a red data frame, a green data frame, and a blue data frame in response to the separate pulses of red, green, and blue visible EMR.

In an implementation, the emitter 102 separately pulses wavebands of visible EMR that are selected for capturing luminance ("Y") imaging data, red chrominance ("Cr") imaging data, and blue chrominance ("Cb") imaging data. In this implementation, the pixel array 125 may separately read out a luminance data frame (comprising only luminance imaging information), a red chrominance data frame, and a blue chrominance data frame.

Figure 2C:
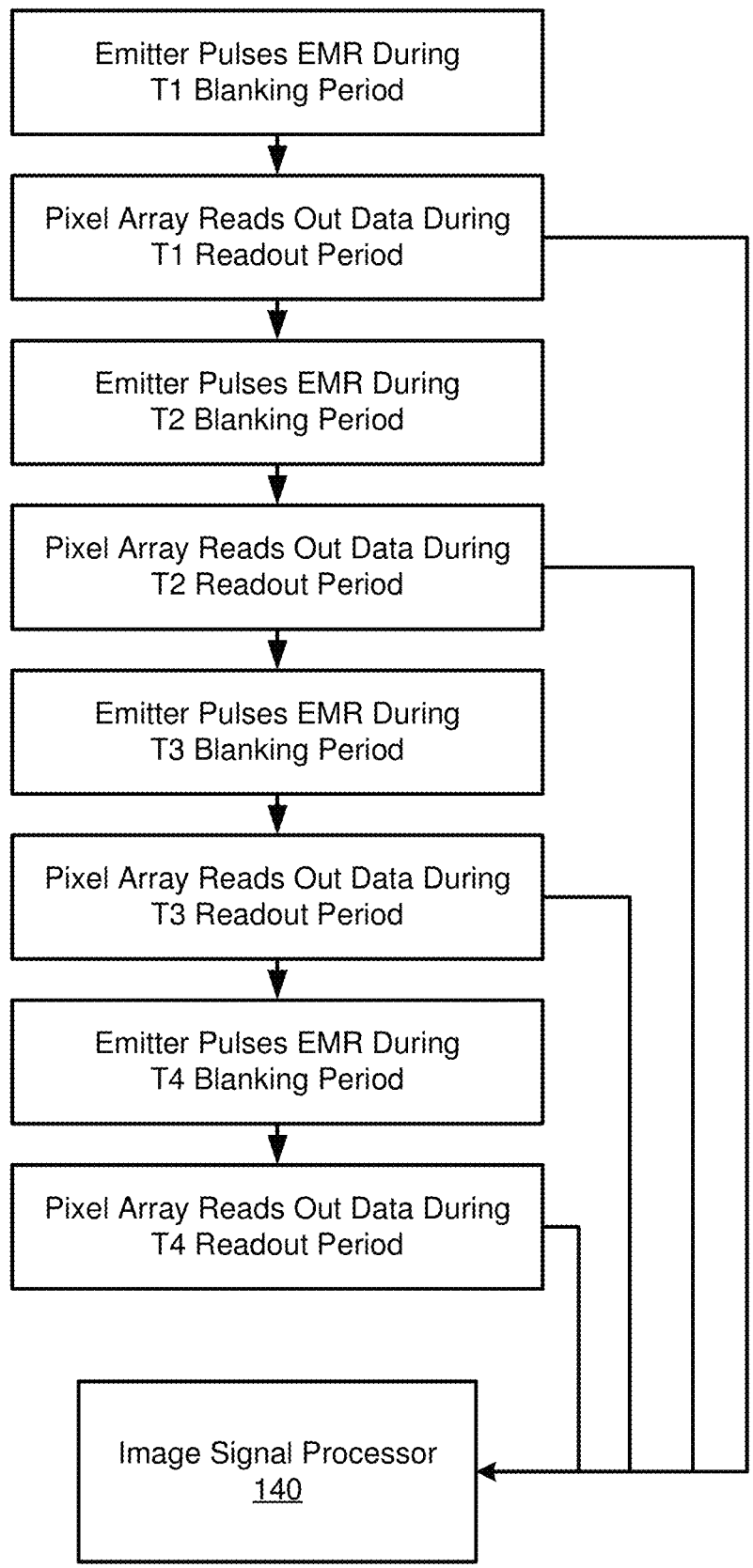
FIG. 2C is a schematic flow chart diagram of a data flow for capturing and reading out data for a time-sequenced visualization system.

FIG. 2C illustrates a schematic flow chart diagram of a process flow for synchronizing operations of the emitter 102 and the pixel array 125. The process flow corresponds with the schematic diagram illustrated in FIG. 2A. The process flow includes the controller 104 instructing the emitter 102 to pulse EMR during a T1 blanking period of the pixel array 125 and then instructing the pixel array 125 to read out data during a T1 readout period following the T1 blanking period. Similarly, the controller 104 instructs the emitter to pulse EMR during each of the T2 blanking period, the T3 blanking period, and the T4 blanking period. The controller 104 instructs the emitter to read out data during each of the T2 readout period, the T3 readout period, and the T4 readout period that follow the corresponding blanking periods. Each of the output data frames are provided to the image signal processor 140.

The emitter 102 pulses according to a variable pulse cycle that includes one or more types of EMR. The variable pulse cycle may include visible EMR, which may include a white light emission, red light emission, green light emission, blue light emission, or some other waveband of visible EMR. The white light emission may be pulsed with a white light emitting diode (LED) or other light source and may alternatively be pulsed with a combination of red, green, and blue light sources pulsing in concert. The variable pulse cycle may include one or more wavebands of EMR that are selected for multispectral imaging or fluorescence imaging. The variable pulse cycle may include one or more emissions of EMR in a mapping pattern selected for three-dimensional topographical mapping or calculating dimensions within a scene. In some cases, several types of EMR are represented in the variable pulse cycle with different regularity than other types of EMR. This may be implemented to emphasize and de-emphasize aspects of the recorded scene as desired by the user.

The controller 104 adjusts the variable pulse cycle in real-time based on the visualization objectives. The system enables a user to input one or more visualization objectives and to change those objectives while using the system. For example, the visualization objective may indicate the user wishes to view only color imaging data, and in this case, the variable pulse cycle may include pulsed or constant emissions of white light (or other visible EMR). The visualization objective may indicate the user wishes to be notified when a scene includes one or more types of tissue or conditions that may be identified using one or more of color imaging, multispectral imaging, or fluorescence imaging. The visualization objective may indicate that a patient has been administered a certain fluorescent reagent or dye, and that fluorescence imaging should continue while the reagent or dye remains active. The visualization objective may indicate the user wishes to view a three-dimensional topographical map of a scene, receive information regarding distances or dimensions within the scene, receive an alert when a tool comes within critical distance from a certain tissue structure, and so forth.

The variable pulse cycle may include one or more finely tuned partitions of the electromagnetic spectrum that are selected to elicit a fluorescence response from a reagent, dye, or auto-fluorescing tissue. The fluorescence excitation wavebands of EMR include one or more of the following: 400±50 nm, 450±50 nm, 500±50 nm, 550±50 nm, 600±50 nm, 650±50 nm, 700±50 nm, 710±50 nm, 720±50 nm, 730±50 nm, 740±50 nm, 750±50 nm, 760±50 nm, 770±50 nm, 780±50 nm, 790±50 nm, 800±50 nm, 810±50 nm, 820±50 nm, 830±50 nm, 840±50 nm, 850±50 nm, 860±50 nm, 870±50 nm, 880±50 nm, 890±50 nm, or 900±50 nm. The aforementioned wavebands may be finely tuned such that the emitter pulses the central wavelength with a tolerance threshold of ±100 nm, ±90 nm, ±80 nm, ±70 nm, ±60 nm, ±50 nm, ±40 nm, ±30 nm, ±20 nm, ±10 nm, ±8 nm, ±6 nm, ±5 nm, ±4 nm, ±3 nm, ±2 nm, ±1 nm, and so forth. In some cases, the emitter includes a plurality of laser bundles that are each configured to pulse a particular wavelength of EMR with a tolerance threshold not greater than +5 nm, ±4 nm, ±3 nm, or ±2 nm.

The variable pulse cycle may include one or more wavebands of EMR that are tuned for multispectral imaging. These wavebands of EMR are selected to elicit a spectral response from a certain tissue or penetrate through a certain tissue (such that substances disposed behind that tissue may be visualized). The multispectral wavebands of EMR include one or more of the following: 400±50 nm, 410±50 nm, 420±50 nm, 430±50 nm, 440±50 nm, 450±50 nm, 460±50 nm, 470±50 nm, 480±50 nm, 490±50 nm, 500±50 nm, 510±50 nm, 520±50 nm, 530±50 nm, 540±50 nm, 550±50 nm, 560±50 nm, 570±50 nm, 580±50 nm, 590±50 nm, 600±50 nm, 610±50 nm, 620±50 nm, 630±50 nm, 640±50 nm, 650±50 nm, 660±50 nm, 670±50 nm, 680±50 nm, 690±50 nm, 700±50 nm, 710±50 nm, 720±50 nm, 730±50 nm, 740±50 nm, 750±50 nm, 760±50 nm, 770±50 nm, 780±50 nm, 790±50 nm, 800±50 nm, 810±50 nm, 820±50 nm, 830±50 nm, 840±50 nm, 850±50 nm, 860±50 nm, 870±50 nm, 880±50 nm, 890±50 nm, 900±50 nm, 910±50 nm, 920±50 nm, 930±50 nm, 940±50 nm, 950±50 nm, 960±50 nm, 970±50 nm, 980±50 nm, 990±50 nm, 1000±50 nm, 900±100 nm, 950±100 nm, or 1000±100 nm. The aforementioned wavebands may be finely tuned such that the emitter pulses the central wavelength with a tolerance threshold of ±100 nm, ±90 nm, ±80 nm, ±70 nm, ±60 nm, ±50 nm, ±40 nm, ±30 nm, ±20 nm, ±10 nm, ±8 nm, ±6 nm, ±5 nm, +4 nm, ±3 nm, ±2 nm, ±1 nm, and so forth. In some cases, the emitter includes a plurality of laser bundles that are each configured to pulse a particular wavelength of EMR with a tolerance threshold not greater than ±5 nm, ±4 nm, ±3 nm, or ±2 nm.

Certain multispectral wavelengths pierce through tissue and enable a medical practitioner to "see through" tissues in the foreground to identify chemical processes, structures, compounds, biological processes, and so forth that are located behind the foreground tissues. The multispectral wavelengths may be specifically selected to identify a specific disease, tissue condition, biological process, chemical process, type of tissue, and so forth that is known to have a certain spectral response.

The variable pulse cycle may include one or more emissions of EMR that are optimized for mapping imaging, which includes, for example, three-dimensional topographical mapping, depth map generation, calculating distances between objects within a scene, calculating dimensions of objects within a scene, determining whether a tool or other object approaches a threshold distance from another object, and so forth. The pulses for laser mapping imaging include EMR formed in a mapping pattern, which may include one or more of vertical hashing, horizontal hashing, a dot array, and so forth.

The controller 104 optimizes the variable pulse cycle to accommodate various imaging and video standards. In most use-cases, the system outputs a video stream comprising at least 30 frames per second (fps). The controller 104 synchronizes operations of the emitter and the image sensor to output data at a sufficient frame rate for visualizing the scene and further for processing the scene with one or more advanced visualization techniques. A user may request a real-time color video stream of the scene and may further request information based on one or more of multispectral imaging, fluorescence imaging, or laser mapping imaging (which may include topographical mapping, calculating dimensions and distances, and so forth). The controller 104 causes the image sensor to separately sense color data frames, multispectral data frames, fluorescence data frames, and mapping data frames based on the variable pulse cycle of the emitter.

In some cases, a user requests more data types than the system can accommodate while maintaining a smooth video frame rate. The system is constrained by the image sensor's ability to accumulate a sufficient amount of electromagnetic energy during each blanking period to output a data frame with sufficient exposure. In some cases, the image sensor outputs data at a rate of 60-120 fps and may specifically output data at a rate of 60 fps. In these cases, for example, the controller 104 may devote 24-30 fps to color visualization and may devote the other frames per second to one or more advanced visualization techniques.

The controller 104 calculates and adjusts the variable pulse cycle of the emitter 102 in real-time based at least in part on the known capabilities of the pixel array 125. The controller 104 may access data stored in memory indicating how long the pixel array 125 must be exposed to a certain waveband of EMR for the pixel array 125 to accumulate a sufficient amount of EMR to output a data frame with sufficient exposure. In most cases, the pixel array 125 is inherently more or less sensitive to different wavebands of EMR. Thus, the pixel array 125 may require a longer or shorter blanking period duration for some wavebands of EMR to ensure that all data frames output by the image sensor 124 comprise sufficient exposure levels.

Figure 3A:
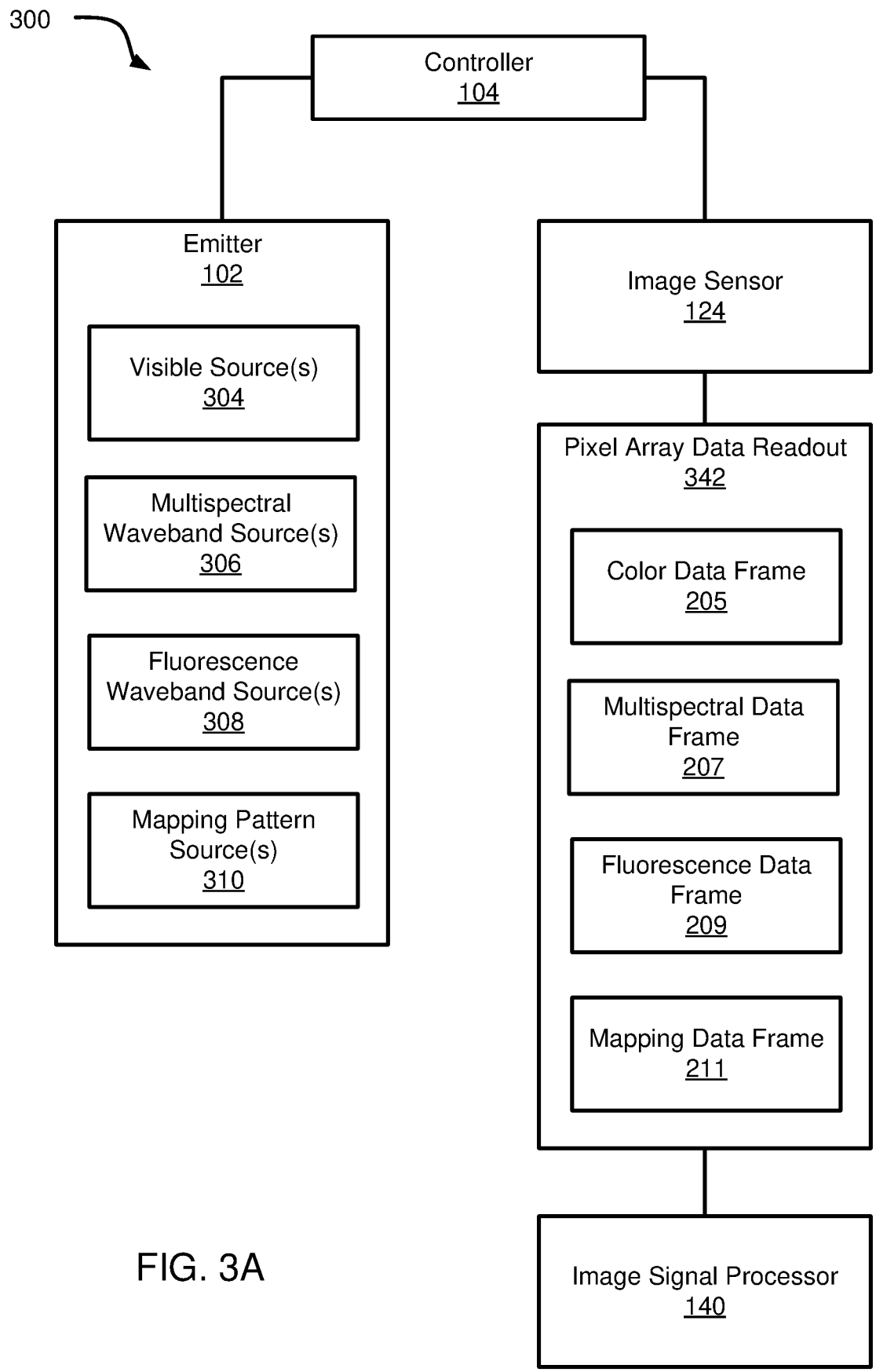
FIG. 3A is a schematic block diagram of an example system for processing data output by an image sensor with a controller in communication with an emitter and the image sensor.
Figure 3B:
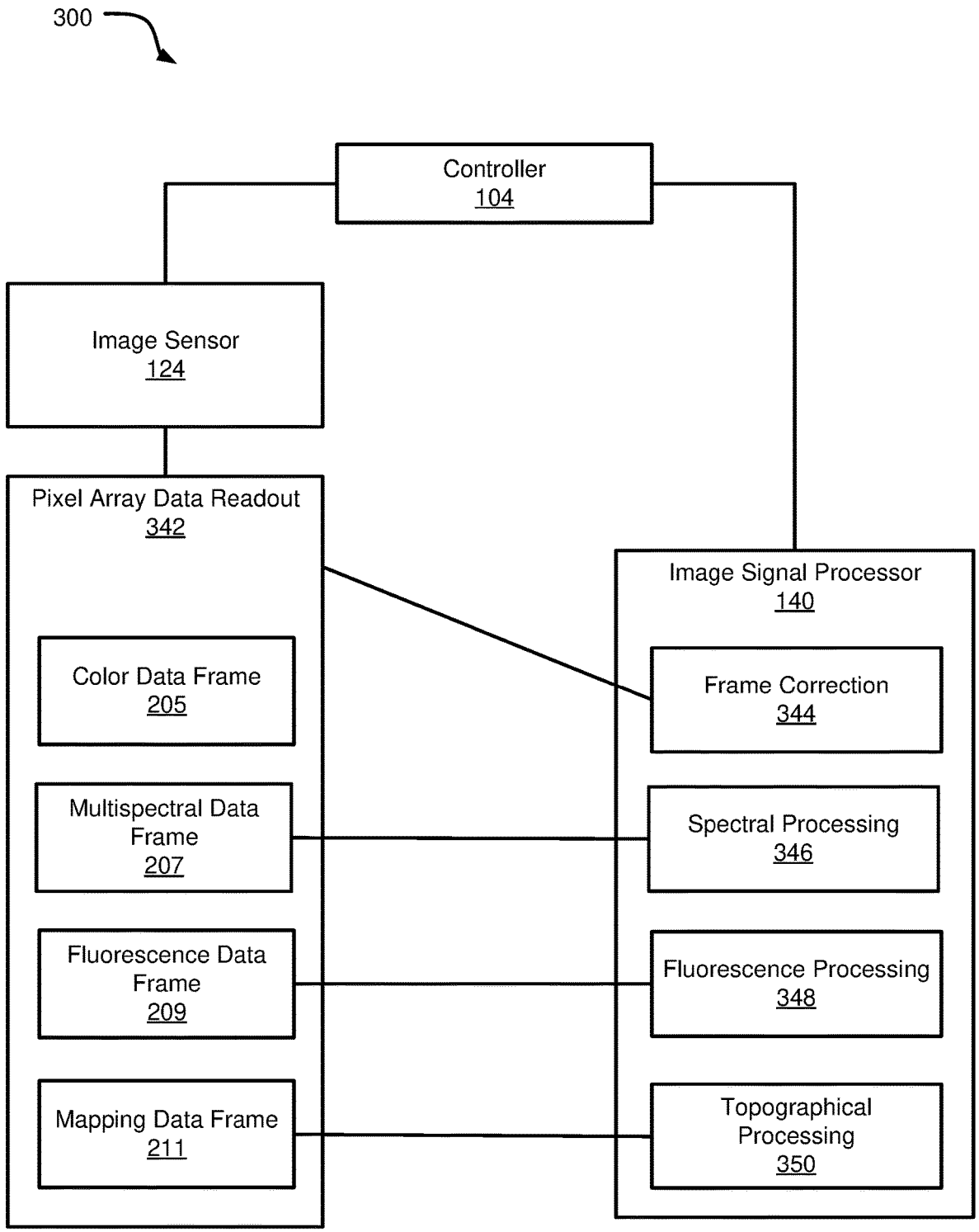
FIG. 3B is a schematic block diagram of an example system for processing data output by an image sensor to generate color imaging data and advanced imaging data.

The controller 104 determines the data input requirements for various advanced visualization algorithms (see, e.g., the algorithms 346, 348, 350 first described in FIG. 3B). For example, the controller 104 may determine that certain advanced visualization algorithms do not require a data input at the same regularity as a color video stream output of 30 fps. In these cases, the controller 104 may optimize the variable pulse cycle to include white light pulses at a more frequent rate than pulses for advanced visualization such as multispectral, fluorescence, or laser mapping imaging. Additionally, the controller 104 determines whether certain algorithms may operate with lower resolution data frames that are read out by the image sensor using a pixel binning configuration. In some cases, the controller 104 ensures that all color frames provided to a user are read out in high-resolution (without pixel binning). However, some advanced visualization algorithms (see e.g., 346, 348, 350) may execute with lower resolution data frames.

The system 100 may include a plurality of image sensors 124 that may have different or identical pixel array configurations. For example, one image sensor 124 may include a monochromatic or "color agnostic" pixel array with no filters, another image sensor 124 may include a pixel array with a Bayer pattern CFA, and another image sensor 124 may include a pixel array with a different CFA. The multiple image sensors 124 may be assigned to detect EMR for a certain imaging modality, such as color imaging, multispectral imaging, fluorescence imaging, or laser mapping imaging. Further, each of the image sensors 124 may be configured to simultaneously accumulate EMR and output a data frame, such that all image sensors are capable of sensing data for all imaging modalities.

The controller 104 prioritizes certain advanced visualization techniques based on the user's ultimate goals. In some cases, the controller 104 prioritizes outputting a smooth and high-definition color video stream to the user above other advanced visualization techniques. In other cases, the controller 104 prioritizes one or more advanced visualization techniques over color visualization, and in these cases, the output color video stream may appear choppy to a human eye because the system outputs fewer than 30 fps of color imaging data.

For example, a user may indicate that a fluorescent reagent has been administered to a patient. If the fluorescent reagent is time sensitive, then the controller 104 may ensure that a sufficient ratio of frames is devoted to fluorescence imaging to ensure the user receives adequate fluorescence imaging data while the reagent remains active. In another example, a user requests a notification whenever the user's tool comes within a threshold distance of a certain tissue, such as a blood vessel, nerve fiber, cancer tissue, and so forth. In this example, the controller 104 may prioritize laser mapping visualization to constantly determine the distance between the user's tool and the surrounding structures and may further prioritize multispectral or fluorescence imaging that enables the system to identify the certain tissue. The controller 104 may further prioritize color visualization to ensure the user continues to view a color video stream of the scene.

Figure 3C:
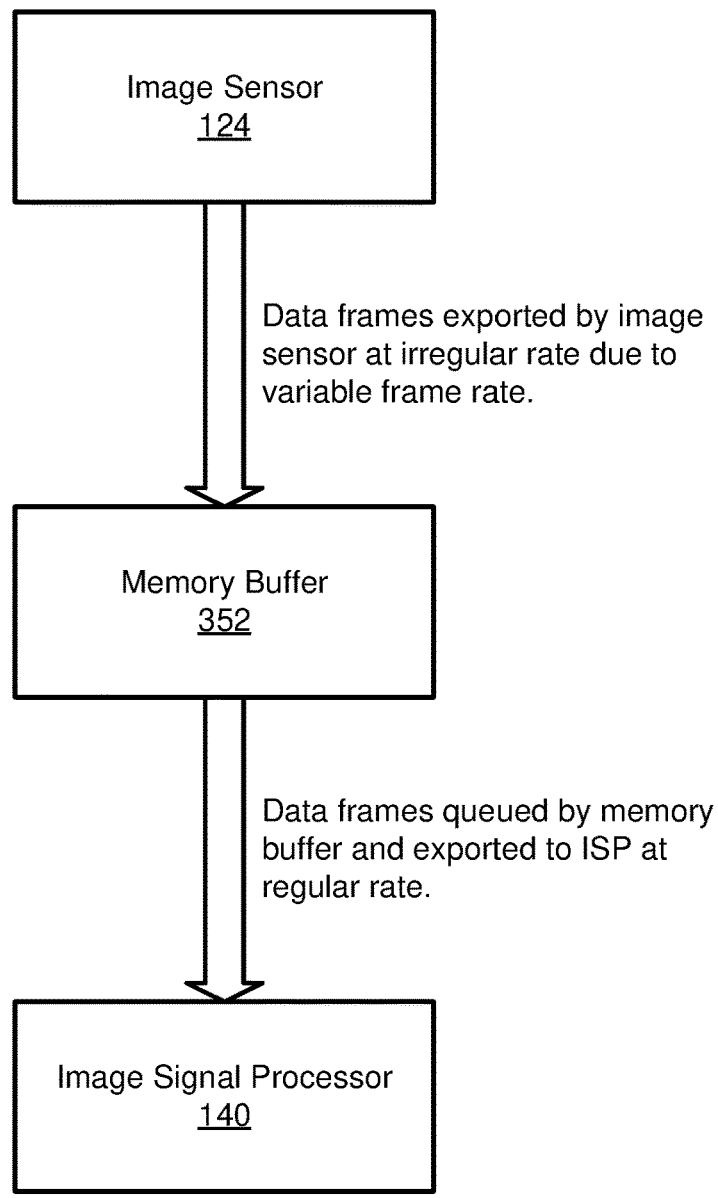
FIG. 3C is a schematic block diagram of an example system for processing data through a memory buffer to provide data frames to an image signal processor at regular intervals.

FIGS. 3A-3C illustrate schematic diagrams of a system 300 for processing data output by an image sensor 124 comprising the pixel array 125. The system 300 includes a controller 104 in communication with each of the emitter 102 and the image sensor 124 comprising the pixel array 125. The emitter 102 includes one or more visible sources 304, multispectral waveband sources 306, fluorescence waveband sources 308, and mapping pattern sources 310 of EMR. The pixel array data readout 342 of the image sensor 124 includes one or more of the color data frames 205, multispectral data frames 207, fluorescence data frames 209, and mapping data frames 211 as discussed in connection with FIG. 2B.

As illustrated in FIG. 3B, all data read out by the pixel array may undergo frame correction 344 processing by the image signal processor 140. In various implementations, one or more of the color data frame 205, the multispectral data frame 207, the fluorescence data frame 209, and the mapping data frame 211 undergoes frame correction 344 processes. The frame correction 344 includes one or more of sensor correction, white balance, color correction, or edge enhancement.

The multispectral data frame 207 may undergo spectral processing 346 that is executed by the image signal processor 140 and/or another processor that is external to the system 300. The spectral processing 346 may include a machine learning algorithm and may be executed by a neural network configured to process the multispectral data frame 207 to identify one or more tissue structures within a scene based on whether those tissue structures emitted a spectral response.

The fluorescence data frame 209 may undergo fluorescence processing 348 that is executed by the image signal processor 140 and/or another processor that is external to the system 300. The fluorescence processing 348 may include a machine learning algorithm and may be executed by a neural network configured to process to fluorescence data frame 209 and identify an intensity map wherein a fluorescence relaxation wavelength is detected by the pixel array.

The mapping data frame 211 may undergo topographical processing 350 that is executed by the image signal processor 140 and/or another processor that is external to the system 300. The topographical processing 350 may include a machine learning algorithm and may be executed by a neural network configured to assess time-of-flight information to calculate a depth map representative of the scene. The topographical processing 350 includes calculating one or more of a three-dimensional topographical map of the scene, a dimension of one or more objects within the scene, a distance between two or more objects within the scene, a distance between a tool and a certain tissue structure within the scene, and so forth.

FIG. 3C illustrates a schematic diagram of a system 300 and process flow for managing data output at an irregular rate. The image sensor 124 operates according to a sensor cycle that includes blanking periods and readout periods. The image sensor 124 outputs a data frame at the conclusion of each readout period that includes an indication of the amount of EMR the pixel array accumulated during the preceding accumulation period or blanking period.

Each frame period in the sensor cycle is adjustable on a frame-by-frame basis to optimize the output of the image sensor and compensate for the pixel array 125 having varying degrees of sensitivity to different wavebands of EMR. The duration of each blanking period may be shortened or lengthened to customize the amount of EMR the pixel array 125 can accumulate. Additionally, the duration of each readout period may be shortened or lengthened by implementing a pixel binning configuration or causing the image sensor to read out each pixel within the pixel array 125. Thus, the image sensor 124 may output data frames at an irregular rate due to the sensor cycle comprising a variable frame rate. The system 300 includes a memory buffer 352 that receives data frames from the image sensor 124. The memory buffer 352 stores the data frames and then outputs each data frame to the image signal processor 140 at a regular rate. This enables the image signal processor 140 to process each data frame in sequence at a regular rate.

Figure 4:
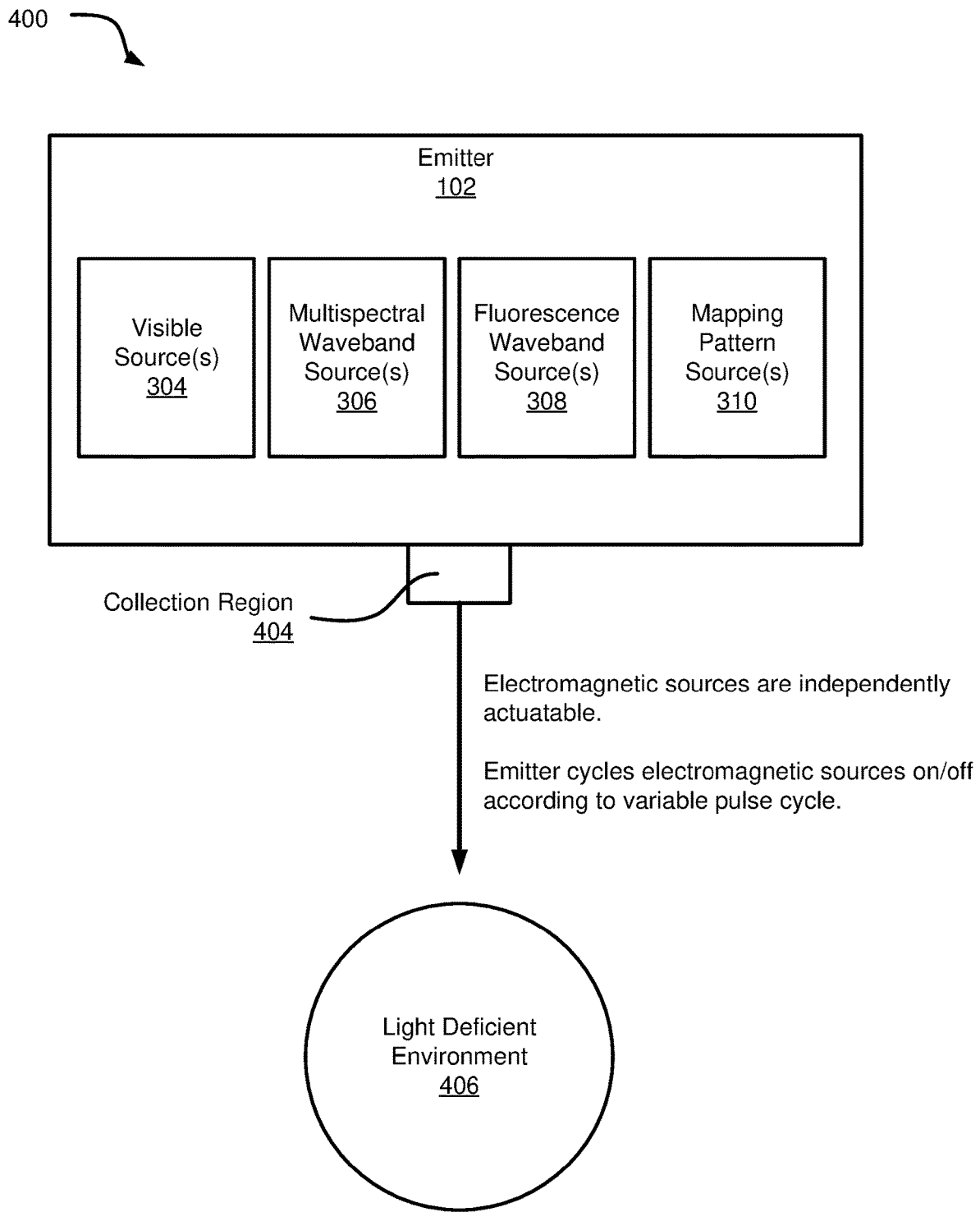
FIG. 4 is a schematic diagram of an illumination system for illuminating a light deficient environment according to a variable pulse cycle.

FIG. 4 is a schematic diagram of an illumination system 400 for illuminating a light deficient environment 406 such as an interior of a body cavity. In most cases, the emitter 102 is the only source of illumination within the light deficient environment 406 such that the pixel array of the image sensor does not detect any ambient light sources. The emitter 102 includes a plurality of separate and independently actuatable sources of EMR, which may include visible source(s) 304, multispectral waveband source(s) 306, fluorescence waveband source(s) 308, and mapping pattern source(s) 310. The emitter may cycle a selection of the sources on and off to pulse according to the variable pulse cycle received from the controller 104. Each of the EMR sources feeds into a collection region 404 of the emitter 102. The collection region 404 may then feed into a waveguide (see e.g., 130 in FIG. 1A) that transmits the pulsed EMR to a distal end of an endoscope within the light deficient environment 406.

The variable pulsing cycle is customizable and adjustable in real-time based on user input. The emitter 102 may instruct the individual EMR sources to pulse in any order. Additionally, the emitter 102 may adjust one or more of a duration or an intensity of each pulse of EMR. The variable pulse cycle may be optimized to sufficiently illuminate the light deficient environment 406 such that the resultant data frames read out by the pixel array 125 are within a desired exposure range (i.e., the frames are neither underexposed nor overexposed). The desired exposure range may be determined based on user input, requirements of the image signal processor 140, and/or requirements of a certain image processing algorithm (see 344, 346, 348, and 350 in FIG. 3B). The sufficient illumination of the light deficient environment 406 is dependent on the energy output of the individual EMR sources and is further dependent on the efficiency of the pixel array 125 for sensing different wavebands of EMR.

Figure 5A:
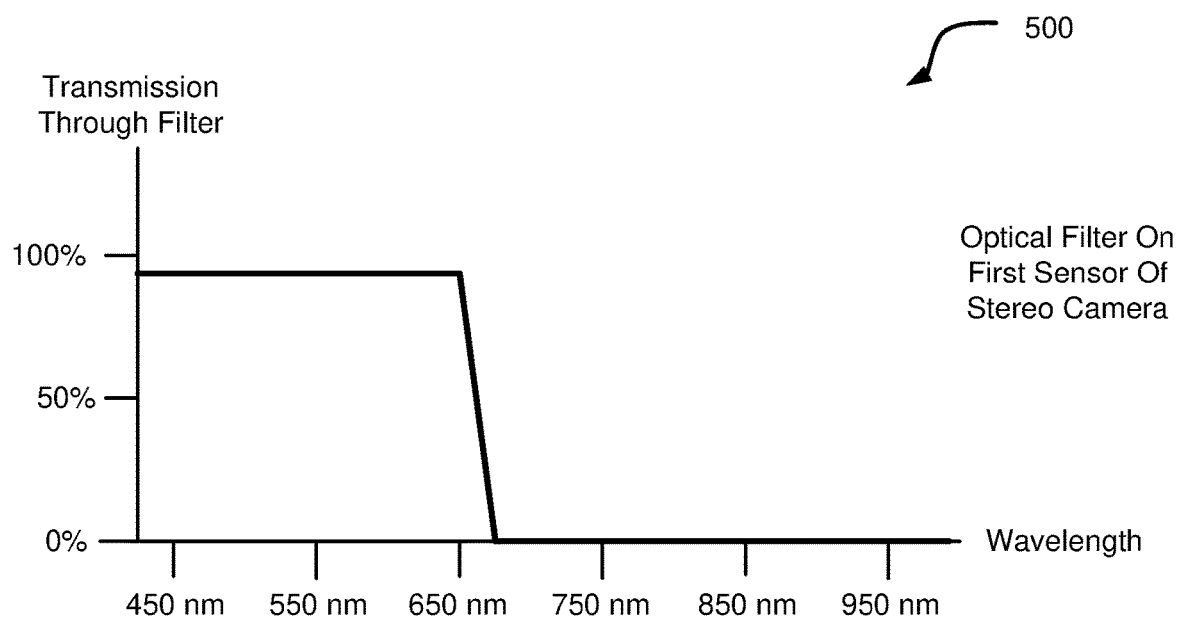
FIG. 5A is a graphical representation of the transmission of electromagnetic radiation through an optical filter on a first image sensor of a stereo camera.
Figure 5B:
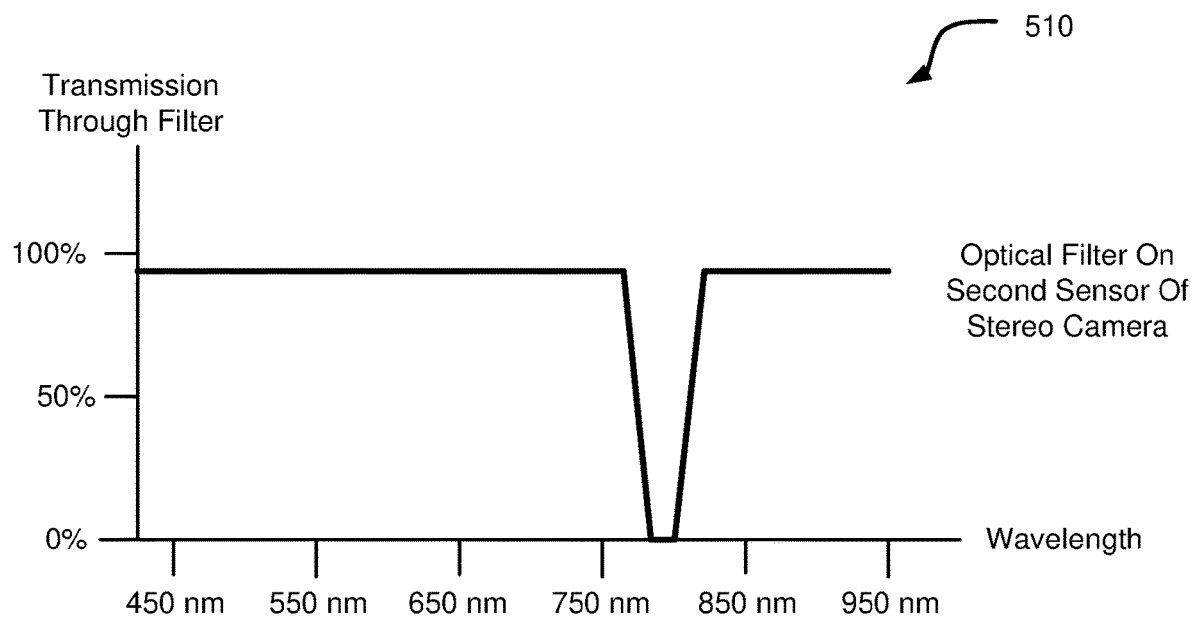
FIG. 5B is a graphical representation of the transmission of electromagnetic radiation through an optical filter on a second image sensor of a stereo camera.

FIGS. 5A and 5B are graphical representations of the transmission of EMR through optical filters. The system 100 may include two or more image sensors that may be used for stereo visualization. The two or more image sensors may be fitted with different optical filters to enable the two or more image sensors to capture different visualization data simultaneously.

The system 100 may be equipped with multiple different optical filter designs on each of the two channels (i.e., the two image sensors 124) of a stereo camera to enable and optimize a "dual mode." The dual mode includes a first image sensor configured to output high-resolution white light video (i.e., color video) for use on a display or otherwise provided to a user. In the dual mode, a second image sensor is configured to collect lower resolution video for advanced visualization, wherein the lower resolution data frames comprise sufficient resolution for algorithmic processing. The second image sensor may operate at a faster speed than the first image sensor, and in some cases, may output two times as many data frames as the first image sensor. In this implementation, some wavelengths of EMR are blocked from reaching the first image sensor and are instead exclusively detected by the second image sensor.

FIG. 5A is a graphical representation of the transmission of EMR through a first optical filter 500 that may be fitted to a first image sensor of a stereo camera. FIG. 5B is a graphical representation of the transmission of EMR through a second optical filter 510 that may be fitted to a second image sensor of a stereo camera within the same system as FIG. 5A. As shown, the first optical filter 500 permits nearly all EMR to pass through the filter up to about 650 nm, and then the transmission of EMR through the first optical filter 500 declines until virtually no EMR can pass through the filter within the near infrared waveband of the electromagnetic spectrum. The second optical filter 510 permits nearly all EMR to pass through the filter at wavelengths outside of a waveband from about 760 nm to about 800 nm.

The first optical filter 500 may include a short pass filter that blocks near infrared (NIR) EMR from reaching the first image sensor. The first optical filter 500 permits EMR within the visible waveband of the electromagnetic spectrum (i.e., from about 450 nm to about 650 nm) to pass through the filter and be detected by the first image sensor. The second optical filter 510 permits all EMR from about 440 nm to about 1000 nm to pass through the filter and be detected by the second image sensor, except for a narrow notch that blocks near infrared EMR used for fluorescence excitation. The second optical filter 510 may be implemented as a narrow notch filter. Other embodiments with different or more complex filters may offer performance advantages and may also be used.

Figure 6A:
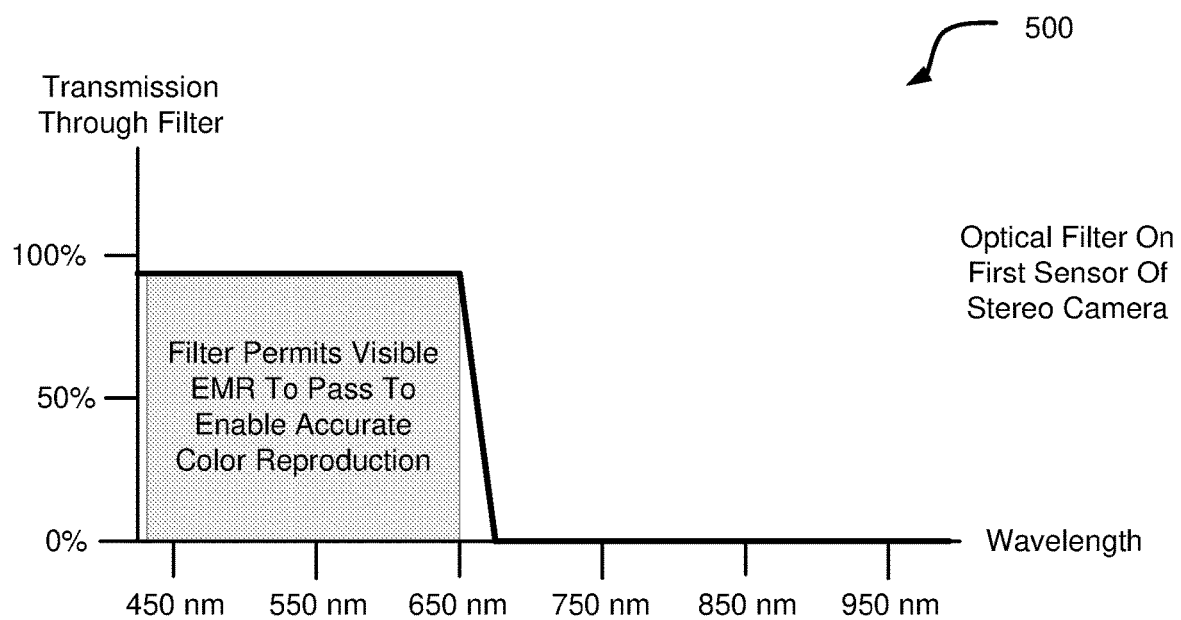
FIG. 6A is a graphical representation of the transmission of electromagnetic radiation through an optical filter on a first image sensor of a stereo camera.
Figure 6B:
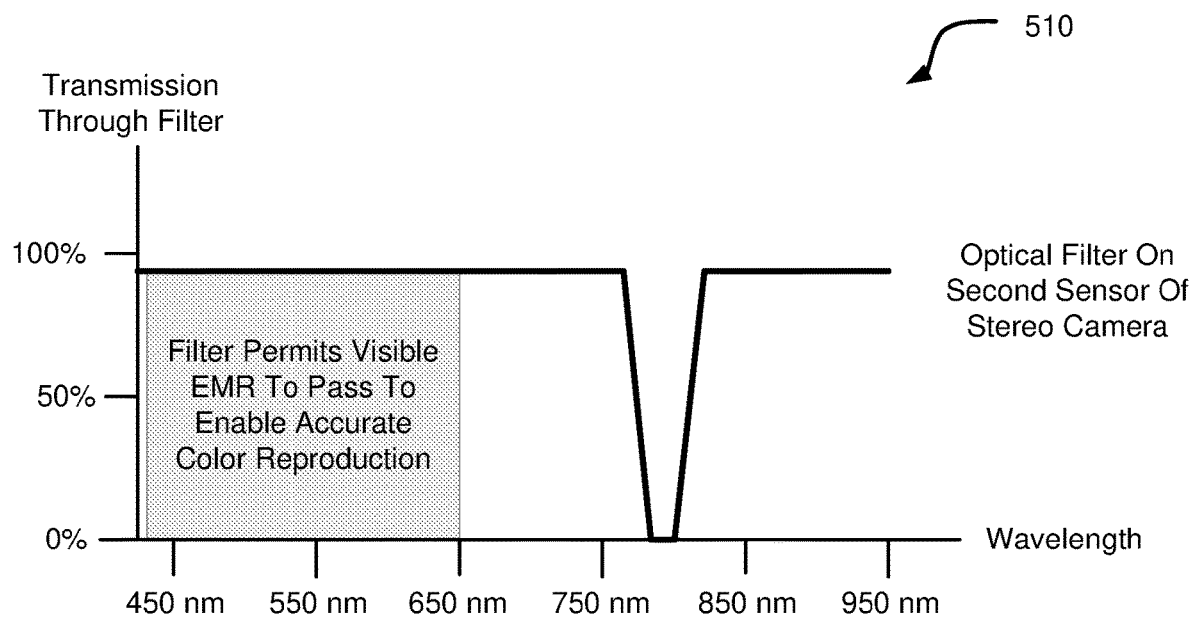
FIG. 6B is a graphical representation of the transmission of electromagnetic radiation through an optical filter on a second image sensor of a stereo camera.

FIGS. 6A-6B are graphical representations of the transmission of EMR through the same optical filters 500, 510 first described in connection with FIGS. 5A-5B. As shown, the first optical filter 500 and the second optical filter 510 permit EMR within the visible range (from about 450 nm to about 650 nm) to pass through and accumulate on the pixel array of the first image sensor and the second image sensor. Thus, the first image sensor and the second image sensor of the stereo camera may accumulate reflected white light and output color data frames comprising an accurate color reproduction of the scene being visualized.

Figure 7A:
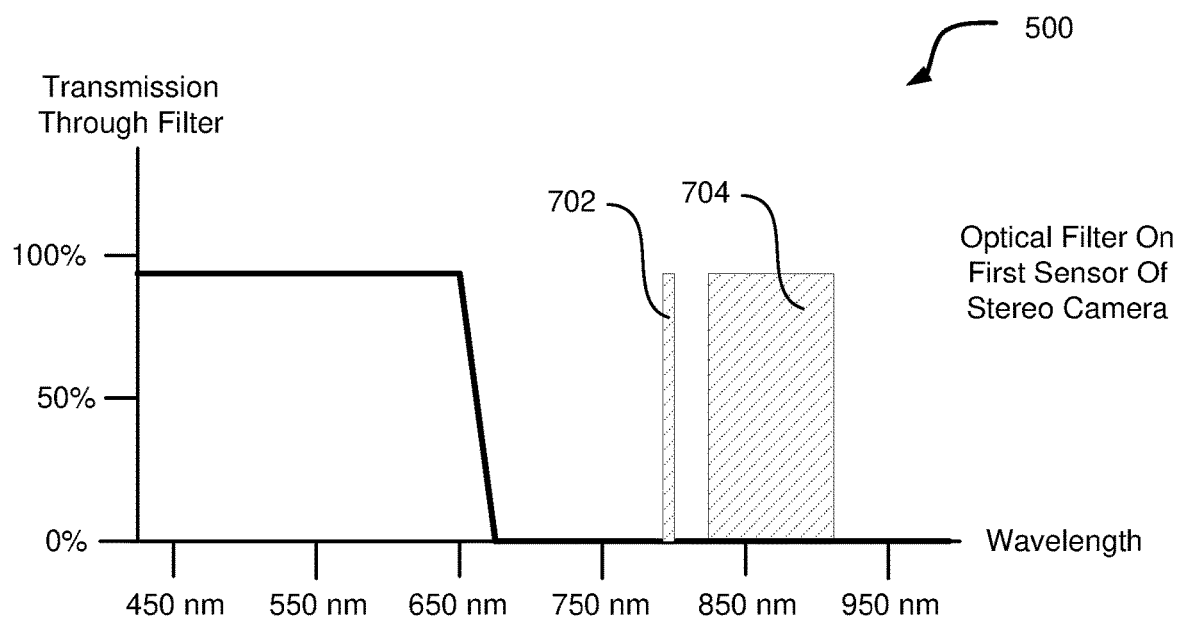
FIG. 7A is a graphical representation of the transmission of electromagnetic radiation through an optical filter on a first image sensor of a stereo camera.
Figure 7B:
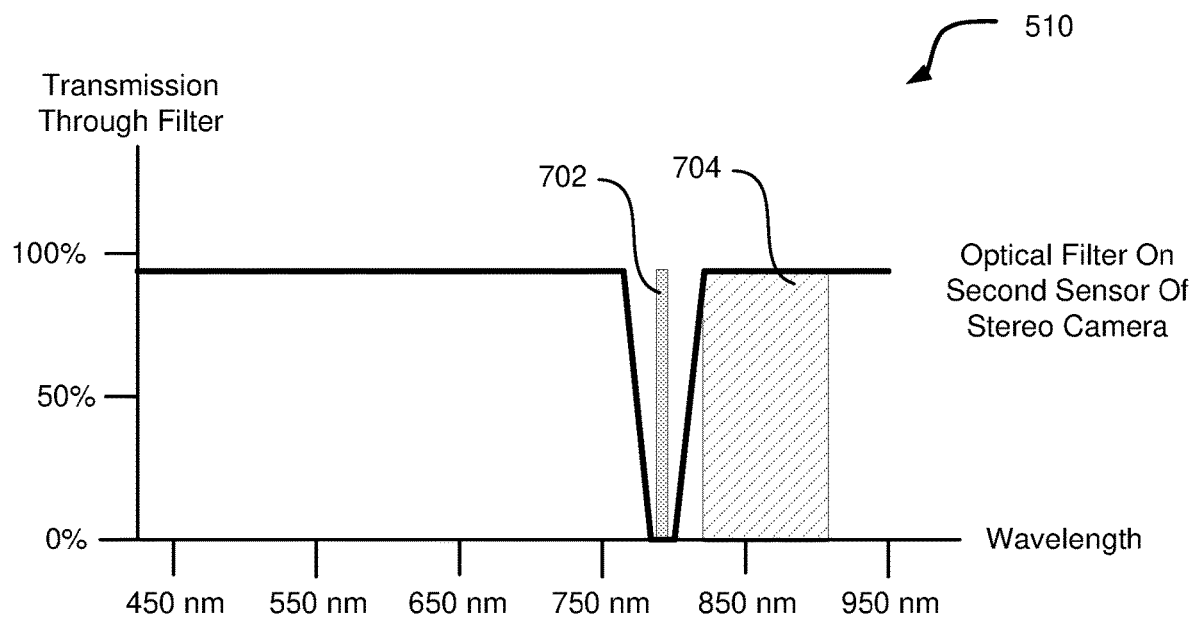
FIG. 7B is a graphical representation of the transmission of electromagnetic radiation through an optical filter on a second image sensor of a stereo camera.

FIGS. 7A-7B are graphical representations of the transmission of EMR through the same optical filters 500, 510 first described in connection with FIGS. 5A-5B. As shown, the first optical filter 500 blocks fluorescence excitation EMR 702 and fluorescence relaxation EMR 704 from reaching the first image sensor of the stereo camera. Thus, the first image sensor does not detect near infrared fluorescence excitation EMR 702 or near infrared fluorescence relaxation EMR 704 that may be emitted by a reagent or tissue. The second optical filter 510 is tuned to block the fluorescence excitation EMR 702 from reaching the second image sensor of the stereo camera. However, the second optical filter 510 permits the fluorescence relaxation EMR 704 (i.e., the fluorescence light emitted by a fluorescing reagent or tissue) to pass through the filter and accumulate on the second image sensor.

Thus, in the implementation illustrated in FIGS. 7A-7B, near infrared fluorescence relaxation EMR 704 is detected only with the second image sensor of the stereo camera. The controller 104 or other processor may compensate by mapping data output by the second image sensor to the first image sensor using disparity map offsets. This enables stereo visualization of near infrared fluorescence relaxation information.

Figure 8A:
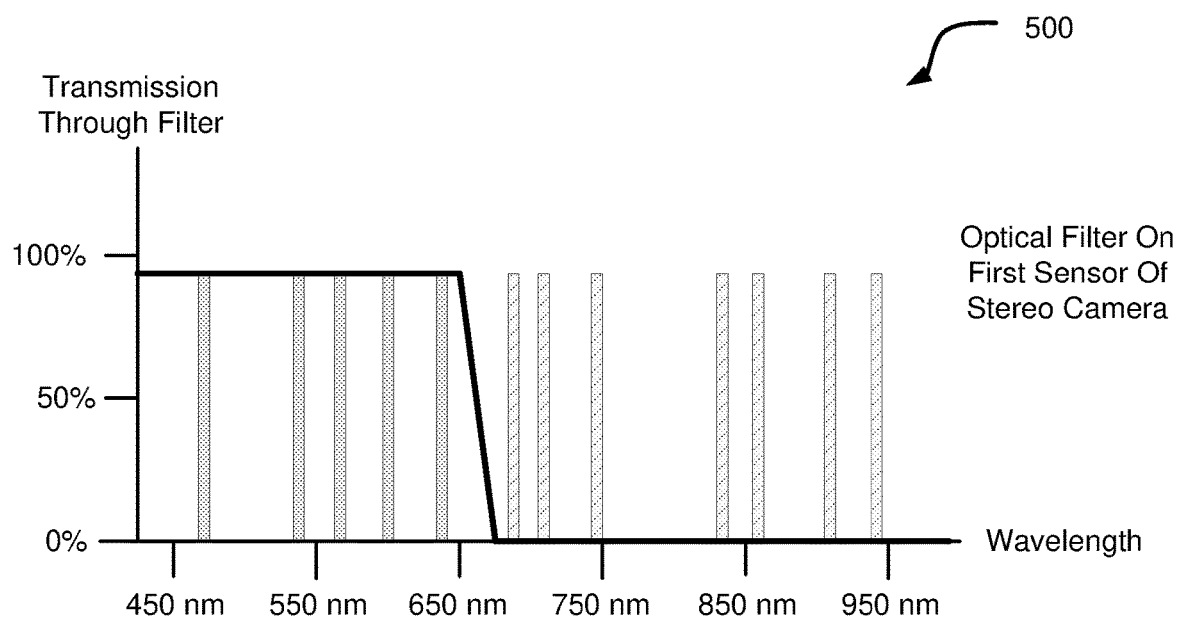
FIG. 8A is a graphical representation of the transmission of electromagnetic radiation through an optical filter on a first image sensor of a stereo camera.
Figure 8B:
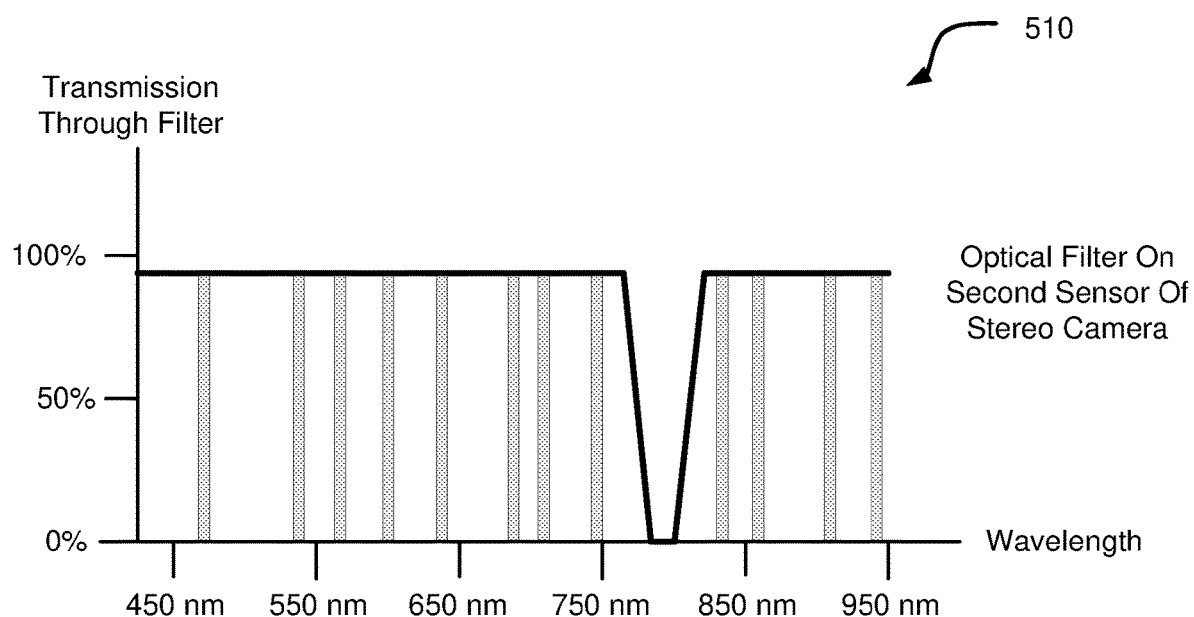
FIG. 8B is a graphical representation of the transmission of electromagnetic radiation through an optical filter on a second image sensor of a stereo camera.

FIGS. 8A-8B are graphical representations of the transmission of EMR through the same optical filters first described in connection with FIGS. 5A-5B. The first optical filter 500 enables narrowband EMR in the visible range to pass through the filter and accumulate on the second image sensor of the stereo camera. The first optical filter 500 blocks narrowband EMR in the near infrared range from passing through the filter and accumulating on the second image sensor of the stereo camera.

The second optical filter 510 permits narrowband EMR in the visible and near infrared ranges to pass through the filter and accumulate on the second image sensor of the stereo camera. The second optical filter 510 may be tuned to specifically block the fluorescence excitation waveband of EMR 702 discussed in connection with FIGS. 7A-7B. Thus, in the implementation illustrated in FIGS. 8A-8B, narrowband near infrared EMR is detected only with the second image sensor of the stereo camera. The controller 104 or other processor may compensate by mapping data output by the second image sensor to the first image sensor using disparity map offsets. This enables stereo visualization of the near infrared information.

The optical filter design described in FIGS. 5A-8B enables numerous advantages. One advantage is the first image sensor may be run exclusively in a full resolution mode, wherein the first image sensor is not instructed to bin its pixel array to reduce the time required to execute a rolling readout sequence. Thus, the data retrieved from the first image sensor may be applied to a full-resolution color video stream rendered on a display or otherwise provided to a user. The second image sensor may concurrently be run in a full resolution mode or a binned lower resolution mode when capturing advanced visualization data. Thus, the stereo camera is optimized for both high-resolution color video, and further for capturing advanced visualization data that may be interpreted by an algorithm (see, e.g., algorithms 346, 348, 350 discussed in connection with FIG. 3B). The tradeoff associated with this "dual mode" is an expected loss of stereo image quality, or possible the loss of stereo view entirely. The dual mode is optional and may be activated or deactivated by the user or controller in real-time.

FIGS. 9-13 are schematic diagrams illustrating example synchronized operational cycles 900, 1000, 1100, 1200, 1300 of the emitter 102 and a stereo camera comprising at least two image sensors 124. The stereo camera includes a first image sensor 910 and a second image sensor 920. The first image sensor 910 may be fitted with the first optical filter 500 described in connection with FIGS. 5A, 6A, 7A, and 8A. The second image sensor 920 may be fitted with the second optical filter 510 described in connection with FIGS. 5B, 6B, 7B, and 8B. The operational cycles 900, 1000, 1100, 1200, 1300 may be optimized and adjusted by the controller in real-time based on user input, resolution of resultant data frames, exposure of resultant data frames, requirements for algorithmic processing, and so forth. The system 100 is implemented such that the "dual mode" visualization illustrated in FIGS. 12 and 13 may be activated or deactivated in real-time.

FIGS. 9-13 are illustrated such that the blanking periods of the image sensors 910, 920 are illustrated with shaded or patterned boxes. The pixel arrays 125 of the image sensors 910, 920 accumulate EMR during the blanking periods and then readout the accumulated EMR during the next subsequent readout period. The readout periods of the image sensors 910, 920 are illustrated with the diagonal lines indicating a rolling readout scheme. It should be appreciated that the duration of time required to complete a rolling readout scheme may be dependent on whether the image sensor is instructed to bin the pixel array. In FIGS. 9-13, full resolution pixel readouts are represented by longer diagonal lines with a smaller slope, and binned pixel readouts are represented by shorter diagonal lines with a steeper slope. The active pulsing periods of the emitter 102 (i.e., when at least one of the EMR sources is cycled on) are also illustrated with shaded or patterned boxes.

Figure 9:
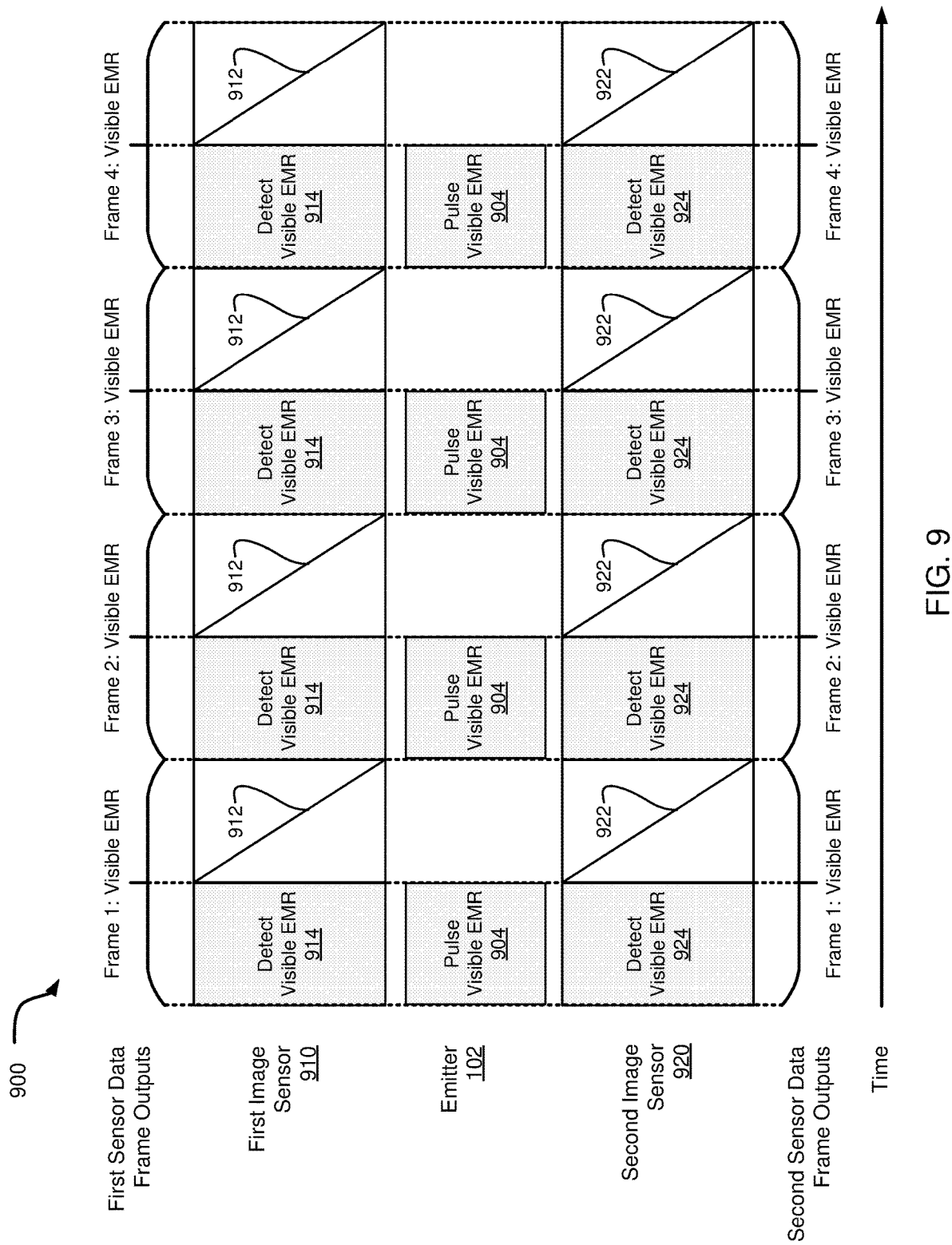
FIG. 9 is a schematic illustration of an example synchronized operational cycle of a stereo camera and an emitter.

FIG. 9 is a schematic illustration of an example synchronized operational cycle 900 including a pulse cycle of the emitter 102 synchronized with sensor cycles of the first image sensor 910 and the second image sensor 920 to output stereo visualization of a scene. The operational cycle 900 is a potential timing diagram enabling high-resolution stereo visualization for rendering on a display or otherwise providing to a user. In this operational cycle 900, both image sensors 910, 920 are operated in full resolution mode (without binning).

The operational cycle 900 includes a first frame period wherein the first image sensor 910 and the second image sensor 920 each output a data frame based on visible EMR, which may specifically include a color data frame 205. The first image sensor 910 detects visible EMR 914 and the second image sensor 920 detects visible EMR 924 during a synchronized blanking period wherein the emitter 102 pulses the visible EMR 904. The visible EMR 904 may specifically include white light pulsed by a single source, such as a white LED light, or by multiple sources acting in concert, such as separate red, green, and blue light sources pulsing simultaneously. The first image sensor 910 reads out the pixel array according to a rolling readout 912 after detecting the visible EMR 914 during the preceding blanking period. Similarly, the second image sensor 920 reads out the pixel array according to a rolling readout 922 after detecting the visible EMR 924 during the preceding blanking period.

The operational cycle 900 further includes a second, third, and fourth frame period in the example illustrated in FIG. 9. Each of these subsequent frame periods is similar to the first frame period, wherein the emitter 102 pulses visible EMR 904 and the image sensors 910, 920 output data for a color data frame.

Figure 10:
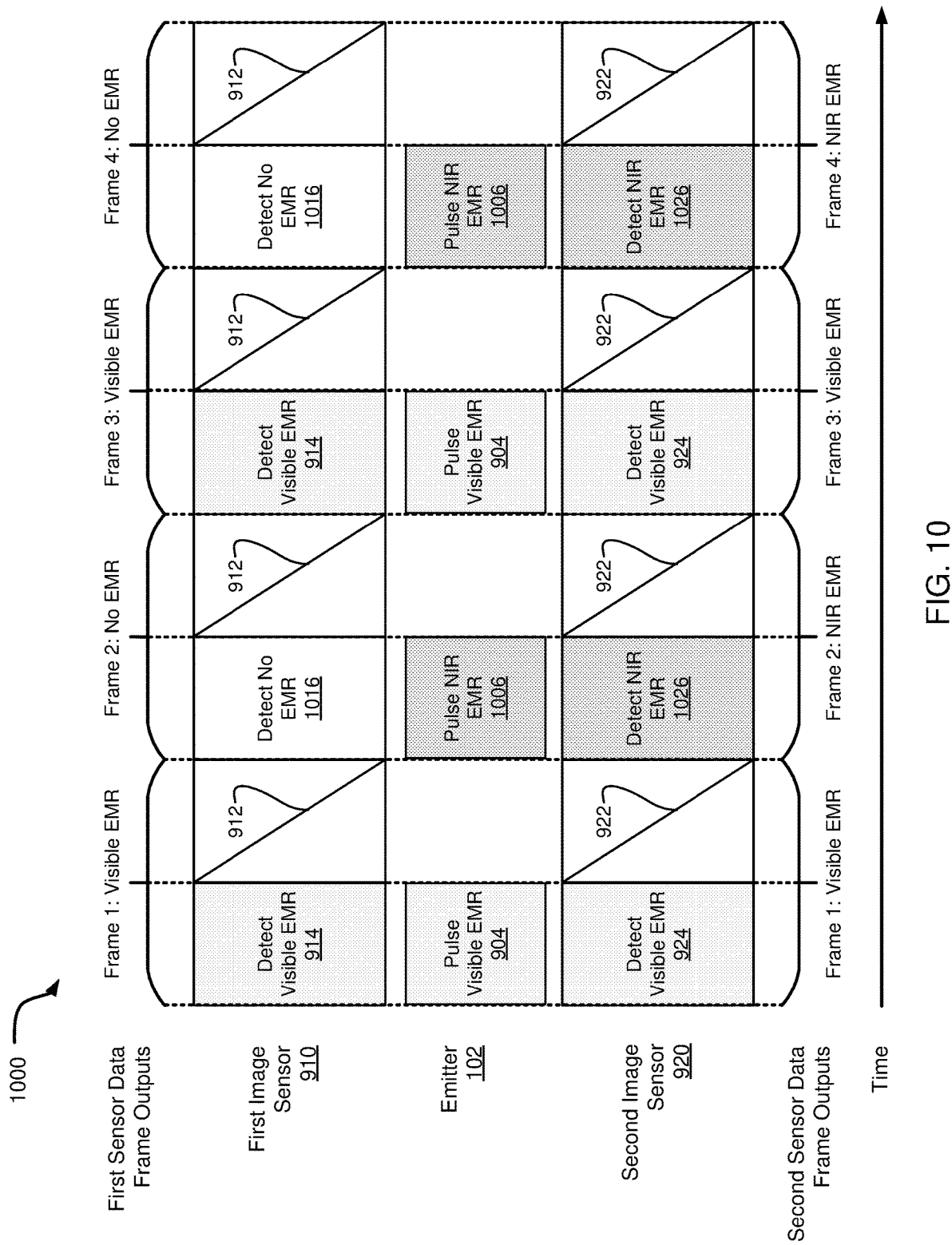
FIG. 10 is a schematic illustration of an example synchronized operational cycle of a stereo camera and an emitter.

FIG. 10 is a schematic illustration of an example synchronized operational cycle 1000 including a pulse cycle of the emitter 102 synchronized with sensor cycles of the first image sensor 910 and the second image sensor 920 to output stereo visualization of a scene. The operational cycle 1000 illustrates a potential timing diagram enabling fluorescence visualization. Both image sensors 910, 920 are run in the full resolution mode (without binning).

Similar to the operational cycle 900 illustrated in FIG. 9, the operational cycle 1000 includes a first frame period and a third frame period wherein the emitter 102 pulses visible EMR 904 and each of the image sensors 910, 920 accumulates the visible EMR and outputs data for a color data frame. The operational cycle 1000 differs from the example illustrated in FIG. 9 during the second frame period and the fourth frame period, wherein the emitter 102 pulses near infrared EMR 1006. During the second and fourth frame periods, the first image sensor 910 does not detect any EMR 1016 because the first image sensor 910 is fitted with an optical filter that blocks the pulsed near infrared EMR 1006 and/or a fluorescence relaxation wavelength that is emitted in response to the emitter 102 pulsing the near infrared EMR. Further, during the second and fourth frame periods, the second image sensor 920 detects near infrared EMR 1026 and outputs a data frame based on the near infrared EMR. The output data frame may include a multispectral data frame 207 and/or a fluorescence data frame 209.

Figure 11:
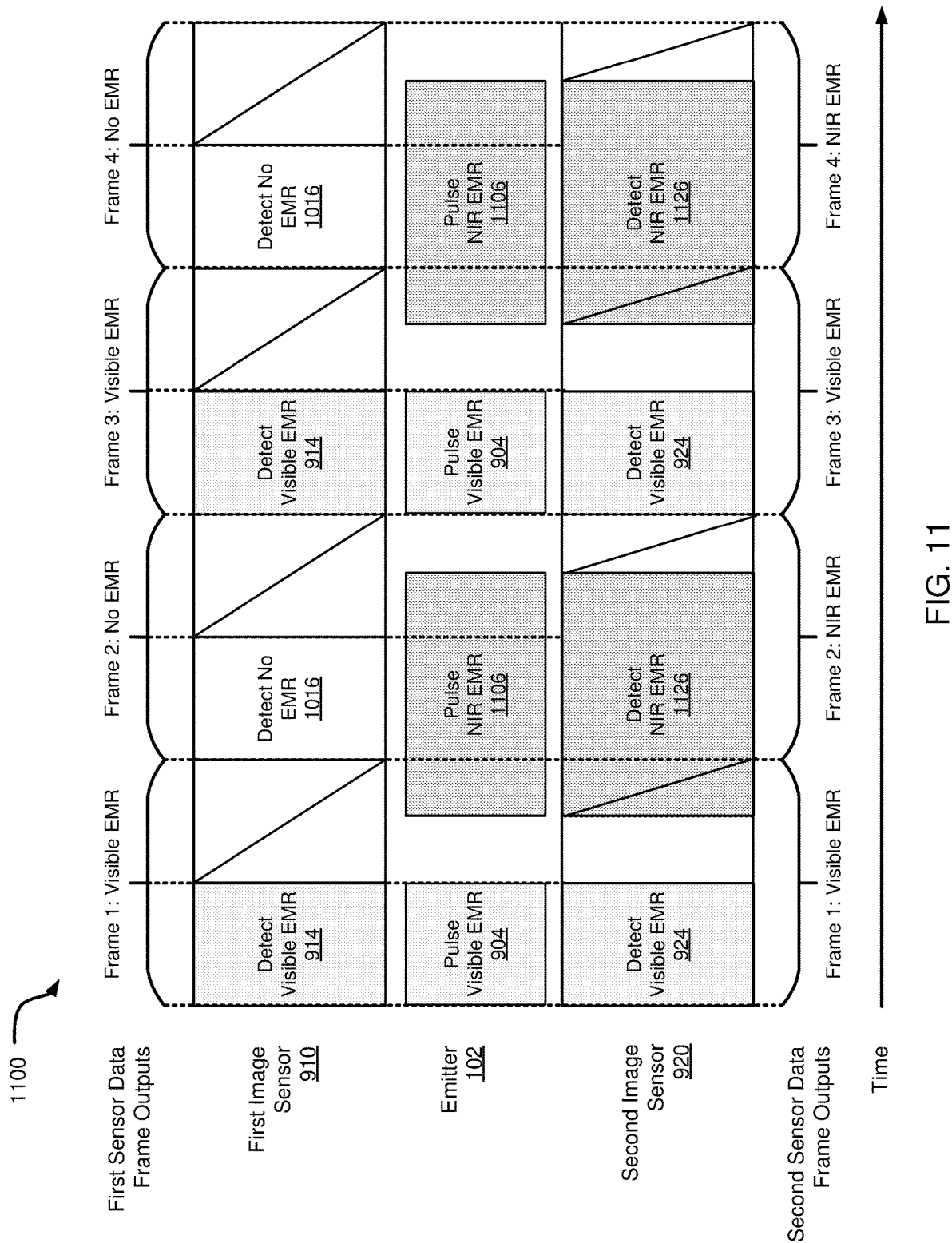
FIG. 11 is a schematic illustration of an example synchronized operational cycle of a stereo camera and an emitter.

FIG. 11 is a schematic illustration of an example synchronized operational cycle 1100 including a pulse cycle of the emitter 102 and sensor cycles of the first image sensor 910 and the second image sensor 920. The operational cycle 1100 is a potential timing diagram enabling fluorescence imaging using the "dual mode" stereo visualization. The first image sensor 910 is run in full resolution mode and outputs a high-resolution color video stream. The second image sensor 920 is run in a binned mode for optimized fluorescence detection. Due to the reduced resolution in the binned mode, the second image sensor 920 has a faster readout of the pixel data, which results in a longer time during which the pixel array may accumulate the fluorescence near infrared EMR. The fluorescence data is mapped to the data output by the first image sensor 910 using a stereo disparity map. Performance of mono visualization is greater when compared with the operational cycle 1000 illustrated in FIG. 10. Stereo visualization is possible, but the quality is expected to degrade due to the lower resolution color video data output by the second image sensor 920.

The operational cycle 1100 illustrated in FIG. 11 is similar to the example illustrated in FIG. 10, wherein the first and third frame periods include an emission of visible EMR, and the second and fourth frame periods include an emission of near infrared EMR. However, the operational cycle 1100 differs from the example illustrated in FIG. 10 because the pulse duration for the pulse of near infrared EMR 1106 is extended to enable the second image sensor 920 to accumulate the near infrared EMR 1126 for a longer duration of time.

The second image sensor 920 bins the pixel array to reduce the time required to read out the data frames. As shown in FIG. 11, the frame period for the second image sensor 920 is adjusted such that a majority of the frame period (roughly 75% in the example shown in FIG. 11) is devoted to accumulating EMR, and the remainder of the frame period is devoted to reading out the pixel array according to a binning configuration. The diagonal lines in FIG. 11 depict the rolling readout schemes for the first image sensor 910 and the second image sensor 920. As shown in FIG. 11, the duration of time required for the second image sensor 920 to read out the pixel array according to a binning configuration is roughly one-half the time required for the first image sensor 910 to read out a full resolution data frame.

The emitter 102 pulses the near infrared EMR 1106 while the second image sensor 920 is reading out the pixel array for a color data frame (in response to detecting the visible EMR 924). Thus, the second image sensor 920 reads out data for the first and third frames while the pixel array is actively accumulating the near infrared EMR being emitted by the emitter 102. The second image sensor 920 reads out the pixel array to generate a near infrared frame after detecting the near infrared EMR 1126.

The image sensors 910, 920 commonly employ a rolling shutter, in which different lines on the pixel arrays 125 are exposed in a sequential manner, as opposed to being exposed simultaneously. In this case, when the image sensors 910, 920 read out the final pixels for a first data frame, some pixels of the pixel array 125 have already begun accumulating EMR for a second data frame. In some implementations, the emitter 102 refrains from illuminating a scene during a readout period of the pixel array, and only illuminates the scene during a blanking period of the image sensor, which may be referred to as a "common exposure" period in some cases. The blanking periods of the image sensors 910, 920 (during which the pixel arrays 125 accumulate EMR) may have a short duration. In some cases, the pixel arrays 125 cannot accumulate sufficient EMR for advanced visualization during a standard blanking period.

The operational cycle 1100 enables the pixel array 125 to accumulate the pulsed near infrared EMR 1106 for a longer duration of time. This may be important if the pixel array 125 is inherently inefficient at detecting the near infrared EMR 1125 and/or if the pulsed near infrared EMR 1106 is relatively dim when compared with the pulsed visible EMR 904.

In the operational cycle 1100, some of the color data frames (see the first and third frame periods of the second image sensor 920) are partially exposed to the pulsed near infrared EMR 1106 where the data frames overlap. Thus, the resulting color data frames include the sum of the accumulated energy from the pulsed visible EMR 904 and some of the pulsed near infrared EMR 1106. However, this "overflow" of the pulsed near infrared EMR 1106 into the color data frame does not impact integrity of the final overlay for several reasons. Namely, the pulsed near infrared EMR 1106 signal is typically very weak when compared with the pulsed visible EMR 904, and thus its contribution in the color data frame is negligible in most cases. Additionally, where the pulsed near infrared EMR 1106 signal is high or comparable to the pulsed visible EMR 904 signal, the effect is masked by an overlay display when the color data frame and the near infrared data frame are combined. Additionally, the two components (i.e., the reflectance signal from the visible EMR 904 and the signal resulting from the pulsed near infrared EMR 1106) may be separated with additional image processing.

The operational cycle 1100 may be implemented to compensate for the relative "weakness" of the near infrared EMR relative to the visible EMR. The near infrared EMR may be "weaker" than the visible EMR based on a variety of factors. One or more of the image sensors 910, 920 may be inherently insensitive to the near infrared EMR or inefficient at detecting the near infrared EMR when compared with the visible EMR. The EMR source configured to pulse the near infrared EMR may be dimmer than the light source configured to pulse the visible EMR. The near infrared EMR emission may be inherently dimmer or lower energy than the visible EMR emission. Thus, the pulse duration for the pulse of near infrared EMR 1106 may be extended to compensate for the relative "weakness" of the near infrared EMR and ensure the image sensor 920 can accumulate a sufficient amount of energy to output a properly exposed data frame.

The controller may select and adjust the operational cycles 900, 1000, 1100, 1200, 1300 in real-time based on user input, the relative strengths of different EMR sources, and the exposure levels of resultant data frames. In an example implementation, a user requests color imaging and fluorescence imaging. The controller determines the near infrared fluorescence source is relatively weak when compared with the white light source. The fluorescence source may be relatively weak based on inherent characteristics of the pixel array. For example, the pixel array may be less sensitive to detecting the fluorescence excitation wavelength emitted by the emitter or the fluorescence relaxation wavelength emitted by a fluorescing tissue or reagent within a scene. Additionally, the fluorescence source may be relatively weak because the fluorescence emission comprises a lower amplitude, lower brightness, and/or lower energy output when compared with the white light source. In response to determining the fluorescence source is "weak" compared with the white light source, the controller may select one of the operational cycles 600, 700 that extends the illumination time for the fluorescence source. The controller may adjust and optimize the operational cycle in real-time to ensure that all resultant data frames are sufficiently exposed.

Figure 12:
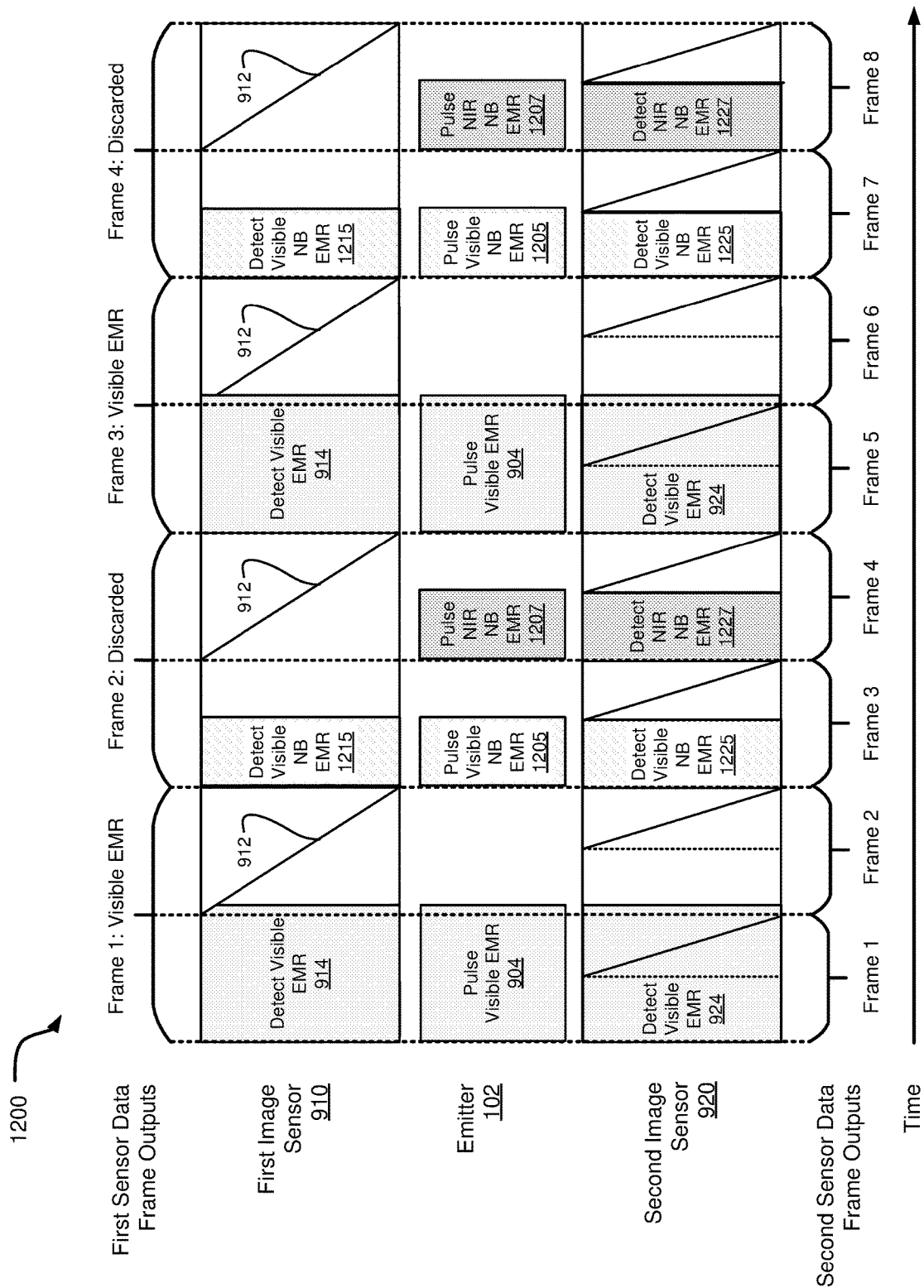
FIG. 12 is a schematic illustration of an example synchronized operational cycle of a stereo camera and an emitter.

FIG. 12 is a schematic illustration of a synchronized operational cycle 1200 including a pulse cycle of the emitter 102 and sensor cycles of the first image sensor 910 and the second image sensor 920. The operational cycle 1200 illustrates a potential timing diagram enabling multispectral visualization using the "dual mode" described herein. The dual mode enables output of a high-resolution color video stream at a first frame rate (e.g., 30 frames per second) and output of lower resolution advanced visualization at second frame rate faster than the first frame rate (e.g., 60 frames per second).

The operational cycle 1200 differs from those illustrated in FIGS. 9-11 because the second image sensor 920 reads out twice as many data frames as the first image sensor 910. The second image sensor 920 may be instructed to bin the pixel array to reduce the total time required to read out the entire pixel array according to a rolling readout scheme.

The emitter 102 pulses visible EMR 904, visible narrowband (NB) EMR 1205, and near infrared narrowband EMR 1207. The first image sensor 910 detects the visible EMR 914 and reads out the pixel array according to a rolling readout 912 scheme to output the first frame. The first image sensor 910 detects the visible narrowband EMR 1215 and reads out the pixel array to output a second frame, which is discarded. The first image sensor 910 repeats this sequence as shown in FIG. 12.

The second image sensor 920 detects the visible EMR 924 and reads out the pixel array while the emitter 102 continues to pulse the visible EMR 904. The second image sensor 920 bins the pixel array to reduce the time required to implement the rolling readout sequence. The second image sensor 920 outputs a color data frame (visible EMR frame) during its first and fifth frame periods illustrated in FIG. 12.

The second image sensor 920 detects the visible narrowband EMR 1225 and reads out the pixel array according to a binning configuration to output a narrowband visible EMR data frame during its third and seventh frame periods as shown in FIG. 12. The second image sensor 920 detects the near infrared narrowband EMR 1227 and reads out the pixel array according to a binning configuration to output a near infrared narrowband data frame during its fourth and eight frame periods as shown in FIG. 12.

The timing of the specific wavelengths of multispectral EMR should be considered so there is no interference with the white light color images collected by the first image sensor. Multispectral illumination in the visible range is detected by the first image sensor 910 and is thus restricted to the blanking periods of the second and fourth frame periods of the first image sensor 910 to avoid interference with the white light frames (the first and third frame periods of the first image sensor 910). Therefore, only the third and seventh frame periods of the second image sensor 920 may be used to collect multispectral EMR that is not blocked from the first image sensor 910. The near infrared EMR (or any EMR blocked from the first image sensor 910) can be used in the fourth and eight frame periods of the second image sensor 920 without interfering with the first image sensor 910. These blocked wavebands can also be used in the third and seventh frame periods of the second image sensor 920, as necessary.

Figure 13:
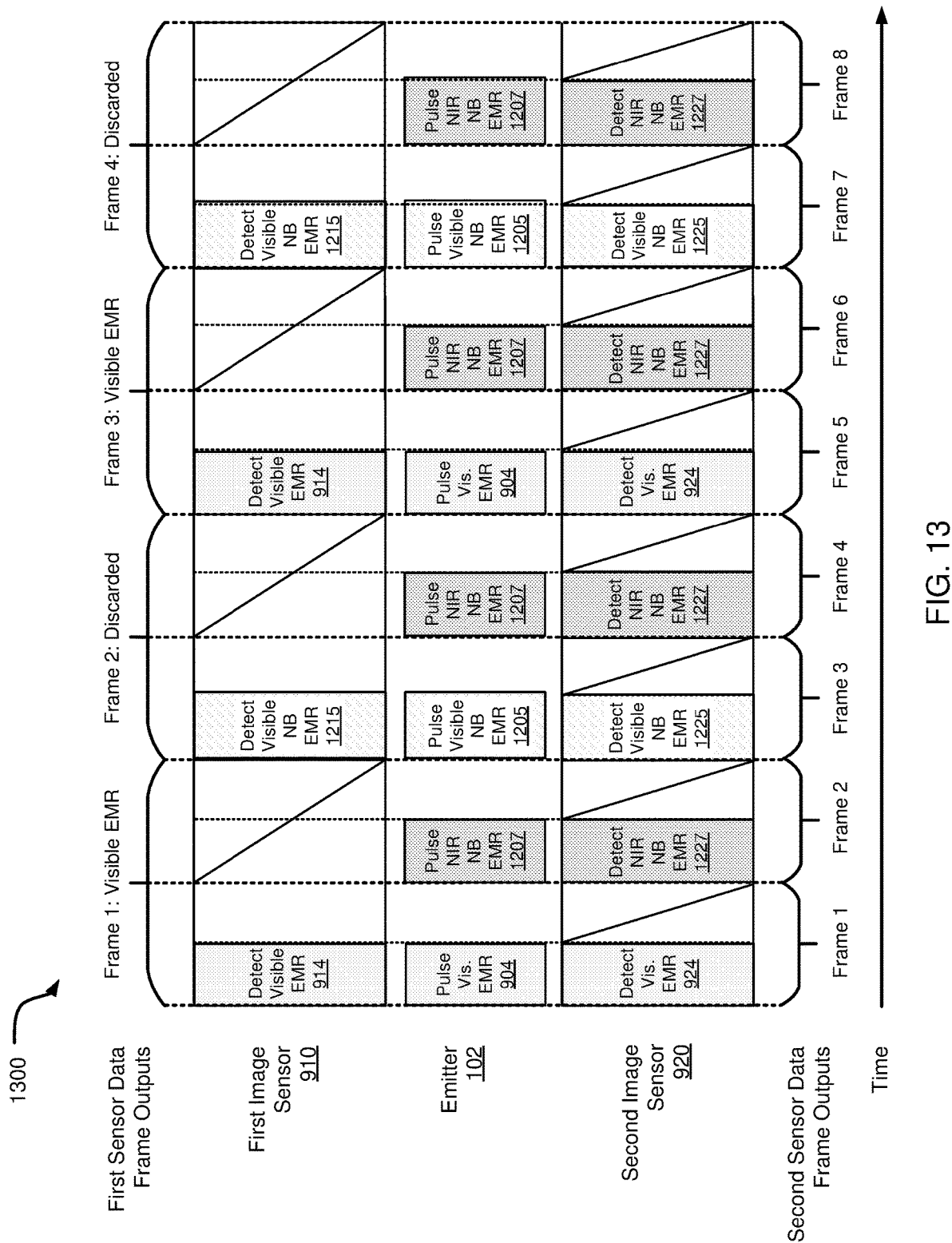
FIG. 13 is a schematic illustration of an example synchronized operational cycle of a stereo camera and an emitter.

FIG. 13 is a schematic illustration of an example synchronized operational cycle 1300 including a pulse cycle of an emitter 102 and sensor cycles of a first image sensor 910 and a second image sensor 920. The operational cycle 1300 illustrates a potential timing diagram for higher performance multispectral visualization enabled by the "dual mode" described herein.

The operational cycle 1300 is similar to the operational cycle 1200 illustrated in FIG. 12, wherein the first image sensor 910 reads out the entire pixel array on a pixel-by-pixel basis to output full resolution data frames, and the second image sensor 920 reads out the pixel array according to a binning configuration to output lower resolution data frames.

The emitter 102 pulses visible EMR 904, near infrared narrowband EMR 1207, and visible narrowband EMR 1205. The first image sensor 910 detects the visible EMR 914 and reads out the entire pixel array on a pixel-by-pixel basis to output full resolution data frames during its first and third frame periods. The first image sensor 910 detects the visible narrowband EMR 1215 and reads out the pixel array on a pixel-by-pixel basis to output full resolution data frames during its second and fourth frame periods. The data frames associated with the second and fourth frame periods are discarded. The first image sensor 910 does not detect the near infrared narrowband EMR 1207 because the first image sensor 910 is fitted with an optical filter that blocks the near infrared narrowband EMR 1207.

The second image sensor 920 detects the visible EMR 924 (may specifically include white light) and reads out the pixel array according to a binning configuration to output a color data frame during its first and fifth frame periods as shown in FIG. 13. The second image sensor 920 detects the near infrared narrowband EMR 1227 and reads out the pixel array according to a binning configuration to output a near infrared data frame during its second, fourth, sixth, and eight frame periods as shown in FIG. 13. The second image sensor 920 detects the visible narrowband EMR 1225 and reads out the pixel array according to a binning configuration to output a narrowband visible data frame during its third and seventh frame periods as shown in FIG. 13.

The timing illustrated in FIG. 13 is possible if the white light illumination power in a short pulse is sufficient for the first image sensor 910 to output a color data frame. With sufficient white light power, the dual mode enables at least 30 frames per second of high-resolution color video with at least 90 frames per second of multispectral visualization. Similar to the operational cycle 1200 illustrated in FIG. 3, only the third and seventh frame periods of the second image sensor 920 can be used to collect multispectral EMR that is not blocked from the first image sensor 910. EMR that is blocked from the first image sensor 910 can be used with any non-white light frame (i.e., the second, third, fourth, sixth, seventh, and eight frame periods of the second image sensor 920).

FIGS. 14A-14B illustrate two implementations for binning a pixel array 125 comprising a color filter array (CFA), and specifically including a version of a Bayer pattern array. FIG. 14A is a schematic illustration of a binned readout 1404 for a traditional Bayer pattern array 1402. FIG. 14B is a schematic illustration of a binned readout 1414 for a quad Bayer pattern array 1412. The binning configurations depicted in FIGS. 14A and 14B might be used by the second image sensor 920 in any of the operational cycles 1100, 1200, 1300 illustrated in FIGS. 11-13.

Pixel binning is a function of image sensors 124 and generally refers to a process wherein the output from multiple physical pixels is combined into a single output value. An image sensor 124 may execute various binning configurations depending on the desired readout duration and the desired resolution. A binning configuration may combine any number of pixels, but is most commonly blocks, or squares, of pixels. An example binning configuration includes a 2×2 binning configuration wherein four physical pixels are combined into a single output value. Another example is a 3×3 binning configuration wherein nine physical pixels are combined into a single output value. Another example is a 4×4 binning configuration wherein 16 physical pixels are combined into a single output value.

Binning on a monochrome sensor typically combines physical blocks of adjacent pixels. Binning on a color sensor combines pixels that share a common filter, and therefore may not be physically adjacent. FIG. 14A is a schematic illustration of a traditional Bayer pattern array 1402, which includes individual pixels that each include a blue color filter, a green color filter, or a red color filter. The example Bayer pattern array 1402 is an 8×8 square that includes 16 pixels with a blue color filter, 16 pixels with a red color filter, and 32 pixels with a green color filter. It should be understood that a traditional pixel array will have many more pixels than the schematic illustration shown in FIGS. 14A-14B, and a traditional high-definition pixel array may include at least 2 Million pixels.

The Bayer pattern array 1402 may be binned with a 2×2 binning configuration, such that four individual pixels having the same color filter are combined to a single readout. When the example 8×8, 64-pixel Bayer pattern array 1402 is binned according to a 2×2 binning configuration as shown in FIG. 14A, the resulting binned readout 1404 includes a 4×4, 16-pixel data output. The information for the 16 binned pixels in the binned readout 1404 is obtained from the corresponding physical pixels in the Bayer pattern array 1402. For example, the B1, B2, B3, B4 pixel within the binned readout 1404 is combining data outputs from each of the individual B1, B2, B3, and B4 physical pixels within the Bayer pattern array 1402. The binned readout 1404 takes only one-fourth of the time that would be required to read out the entire Bayer pattern array 1402, but the binned readout 1404 only has one-fourth the resolution of the entire Bayer pattern array 1402.

The binned readout 1404 combines pixels having the same color filter, even when those pixels are not adjacent to one another. The output values from individual pixels may be combined in two ways, namely, averaging the individual pixel values or summing the individual pixel values. When averaging the individual pixel values, the average outputs from each of the individual pixels (in the case of FIG. 14A, there are four individual pixel values) is averaged and output as a new binned pixel. For example, if R1=96, R2-96, R3=100, and R4=120, then the red binned pixel ((R1, R2, R3, R4) will equal 103. The benefit of averaging binning is a reduction in overall noise in the binned image. In the example, R4 has a significantly higher value than R1, R2, or R3 due to noise in the specific pixel, and this will be noticeable as a bright spot in the resultant image. The red binned value will be closer to the value of the surrounding pixels and thus will not appear as a bright spot.

When summing the individual pixel values, the outputs from each of the individual pixels (in the case of FIG. 14A, there are four individual pixel values) is summed and output as the new binned pixel. For example, if R1=96, R2=96, R3=100, and R4=120, then the red binned pixel (R1, R2, R3, R4) will equal 412. The benefit of summation binning is an increase in effective sensitivity. In the example, the red binned pixel has a higher output (representing more EMR accumulated) than R1, R2, R3, or R4 individually.

Functionally, binning can be implemented in analog or digital. Analog binning in the pixel readout circuitry of an imaging sensor enables a faster readout of a data frame because the image sensor 124 treats the group of individual pixels as a single pixel. Digital binning occurs after the analog-to-digital conversion and thus the readout time of the video frame is not faster. Digital binning may occur in the digital circuitry of an image sensor 124, system hardware, or system software.

Because binning combines multiples pixels into a single pixel, it results in a smaller output data frame having fewer pixels and a loss of resolution. For example, an input data frame size of 1920×1080 pixels (2,073,600 total pixels) that is binned with a 2×2 binning configuration will output a data frame having a size of 960×540 pixels (518,400 total pixels). The smaller data frame size can be beneficial because it contains less pixel data that must be processed.

However, the optical resolution loss can be greater than the number of pixels would indicate. As seen in FIG. 14A, in the standard Bayer pattern array 1402, the colored filters being binned are not physically adjacent to one another. If the image sensor having a Bayer pattern array 1402 has a pixel pitch of 2 μm, then this will limit the size of an object that can be resolved. The 2×2 binning pixel is represented as a 4 μm pitch, but the individual pixels are spread out in a 3×3 grid. This results in the binned pixel having an effective size of a 6 μm pitch when considering the size of an object that can be resolved. In this example, despite the digital vertical resolution being reduced to one-half the original, the optical vertical resolution is reduced to one-third the original (i.e., from 2 μm pitch to 6 μm pitch).

If binning is an intended operating mode, then the optical resolution may be improved by using an image sensor 124 with a modified quad Bayer pattern array 1412 such as the one shown in FIG. 14B. The quad Bayer pattern array 1412 covers a block of four individual adjacent pixels, and these same pixels are combined during a 2×2 binning operation. This results in a binned readout 1414 data frame with equivalent digital and optical resolution. This principle can be applied to larger blocks of pixels as needed, including a 3×3 Bayer, 4×4 Bayer, and so forth. This filter configuration may specifically be chosen when analog summation binning is the intended use because the binned image approximates the performance of an image sensor 124 with a larger (more sensitive) pixel.

Figure 15A:
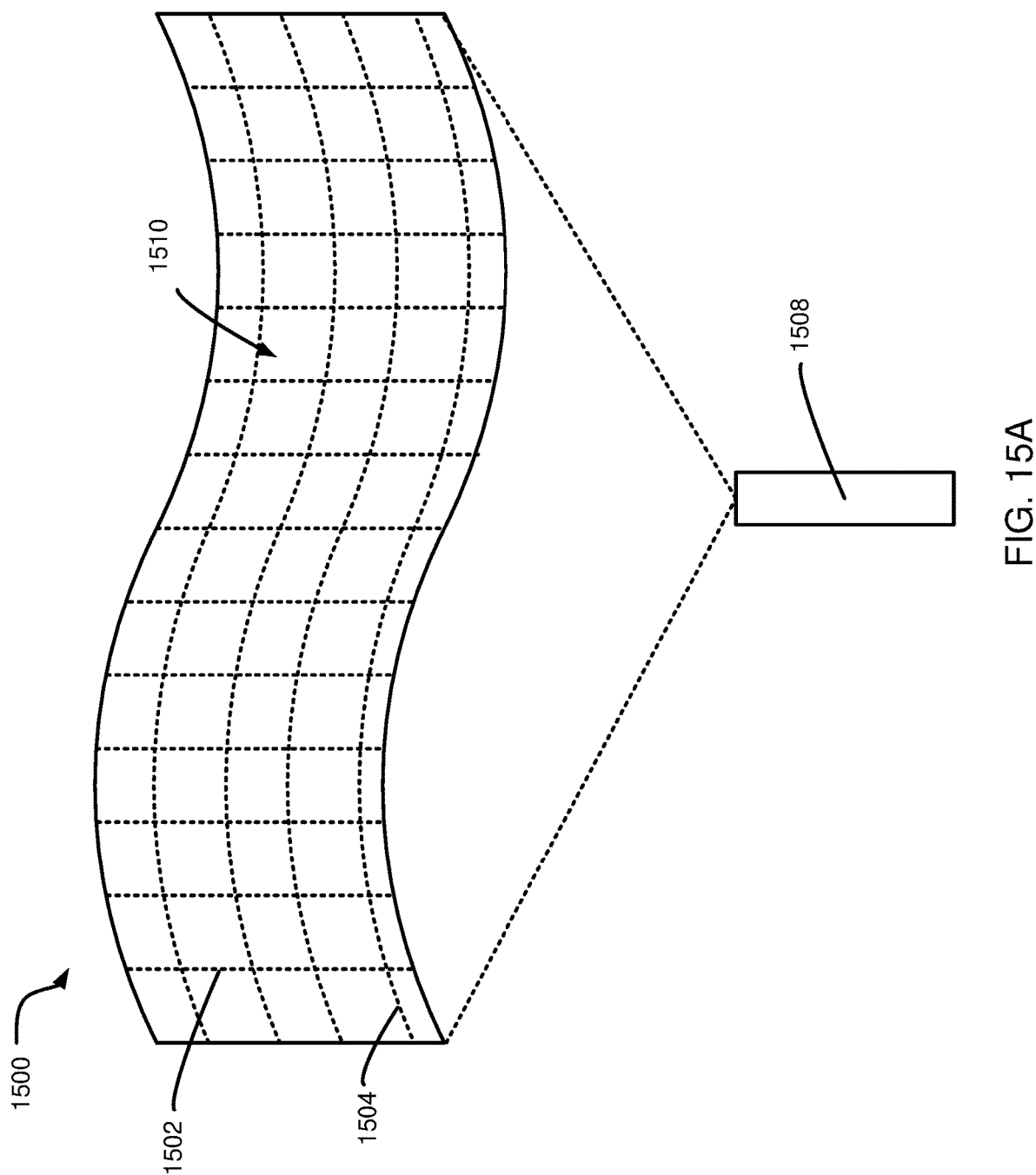
FIG. 15A is a schematic illustration of an example mapping pattern comprising a grid array.

FIGS. 15A and 15B illustrate schematic diagrams of a system 1500 for emitting EMR in a mapping pattern 1510. The emitter 102 may pulse the mapping pattern 1510 using a low mode laser light that is diffracted to generate the applicable mapping pattern 1510. The mapping pattern 1510 reflects off tissue in a way that depends on the wavelength of the EMR and the specific anatomical features of the tissue.

The example mapping pattern 1510 illustrated in FIG. 15A is a grid array comprising vertical hashing 1502 and horizontal hashing 1504. The example mapping pattern 1510 illustrated in FIG. 15B is a dot array. The mapping pattern 1510 may include any suitable array for mapping a surface, including, for example, a raster grid of discrete points, an occupancy grid map, a dot array, vertical hashing, horizontal hashing, and so forth. The mapping pattern 1510 is emitted by an illumination source 1508, which may originate with an EMR source within the emitter 102 and terminate with an endoscope 110 or tool 108.

As discussed in connection with FIGS. 1A-1C, the distal end of an endoscope 110 may include one or more waveguides 130 that emit EMR that originated at the emitter 102. The mapping pattern 1510 may be emitted from these waveguides 130 and projected on to a surface of a tissue. Additionally, one or more tools 108 within a scene may include a waveguide 131 that terminates at a distal end of the tool 108 and/or a side of the tool 108 as shown in FIG. 1A. This waveguide 131 may also emit the mapping pattern 1510 on to a surface of a tissue within a scene. In some cases, the tool 108 and the endoscope 110 emit the mapping pattern 1510 in concert, and the resultant data frames captured by the image sensor 124 comprise data for tracking the location of the tool 108 within the scene relative to the endoscope 110 or other tools 108.

The emitter 102 may pulse the mapping pattern 1510 at any suitable wavelength of EMR, including, for example, ultraviolet light, visible, light, and/or infrared or near infrared light. The surface and/or objects within the environment may be mapped and tracked at very high resolution and with very high accuracy and precision.

The mapping pattern 1510 is selected for the desired anatomical measurement scheme, such as three-dimensional topographical mapping, measuring distances and dimensions within a scene, tracking a relative position of a tool 108 within a scene, and so forth. The image sensor 124 detects reflected EMR and outputs a mapping data frame 211 in response to the emitter 102 pulsing the mapping pattern 1510. The resultant mapping data frame 211 is provided to a topographical processing 350 algorithm that is trained to calculate one or more of a three-dimensional topographical map of a scene, a distance between two or more objects within the scene, a dimension of an object within the scene, a relative distance between a tool and another object within the scene, and so forth.

The emitter 102 may pulse the mapping pattern 1510 at a sufficient speed such that the mapping pattern 1510 is not visible to a user. In various implementations, it may be distracting to a user to see the mapping pattern 1510 during an endoscopic visualization procedure. In some cases, a rendering of the mapping pattern 1510 may be overlaid on a color video stream to provide further context to a user visualizing the scene. The user may further request to view real-time measurements of objects within the scene and real-time proximity alerts when a tool approaches a critical structure such as a blood vessel, nerve fiber, cancer tissue, and so forth. The accuracy of the measurements may be accurate to less than one millimeter.

Figure 16:
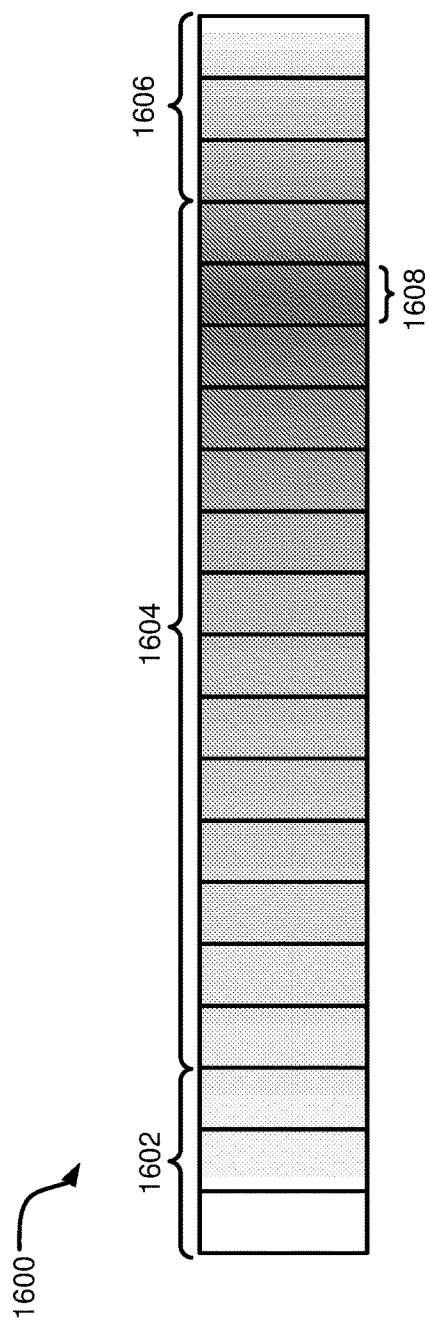
FIG. 16 illustrates a portion of the electromagnetic spectrum divided into a plurality of different wavebands which may be pulsed by sources of electromagnetic radiation of an emitter.

FIG. 16 illustrates a portion of the electromagnetic spectrum 1600 divided into twenty different wavebands 1608. The number of wavebands is illustrative only. In at least one embodiment, the spectrum 1600 may be divided into hundreds of wavebands.

The spectrum 1600 may extend from the infrared spectrum 1602, through the visible spectrum 1604, and into the ultraviolet spectrum 1606. Each waveband 1608 may be defined by an upper wavelength and a lower wavelength.

Multispectral imaging incudes imaging information from across the electromagnetic spectrum 1600. A multispectral pulse of EMR may include a plurality of sub-pulses spanning one or more portions of the electromagnetic spectrum 1600 or the entirety of the electromagnetic spectrum 1600. A multispectral pulse of EMR may include a single partition of wavelengths of EMR. A resulting multispectral data frame includes information sensed by the pixel array subsequent to a multispectral pulse of EMR. Therefore, a multispectral data frame may include data for any suitable partition of the electromagnetic spectrum 1600 and may include multiple data frames for multiple partitions of the electromagnetic spectrum 1600.

The emitter 102 may include any number of multispectral EMR sources as needed depending on the implementation. In one embodiment, each multispectral EMR source covers a spectrum covering 40 nanometers. For example, one multispectral EMR source may emit EMR within a waveband from 500 nm to 540 nm while another multispectral EMR source may emit EMR within a waveband from 540 nm to 580 nm. In another embodiment, multispectral EMR sources may cover other sizes of wavebands, depending on the types of EMR sources available or the imaging needs. Each multispectral EMR source may cover a different slice of the electromagnetic spectrum 1600 ranging from far infrared, mid infrared, near infrared, visible light, near ultraviolet and/or extreme ultraviolet. In some cases, a plurality of multispectral EMR sources of the same type or wavelength may be included to provide sufficient output power for imaging. The number of multispectral EMR sources needed for a specific waveband may depend on the sensitivity of a pixel array 125 to the waveband and/or the power output capability of EMR sources in that waveband.

The waveband widths and coverage provided by the EMR sources may be selected to provide any desired combination of spectrums. For example, contiguous coverage of a spectrum 1600 using very small waveband widths (e.g., 10 nm or less) may allow for highly selective multispectral and/or fluorescence imaging. The waveband widths allow for selectively emitting the excitation wavelength(s) for one or more particular fluorescent reagents. Additionally, the waveband widths may allow for selectively emitting certain partitions of multispectral EMR for identifying specific structures, chemical processes, tissues, biological processes, and so forth. Because the wavelengths come from EMR sources which can be selectively activated, extreme flexibility for fluorescing one or more specific fluorescent reagents during an examination can be achieved. Additionally, extreme flexibility for identifying one or more objects or processes by way of multispectral imaging can be achieved. Thus, much more fluorescence and/or multispectral information may be achieved in less time and within a single examination which would have required multiple examinations, delays because of the administration of dyes or stains, or the like.

Figure 17:
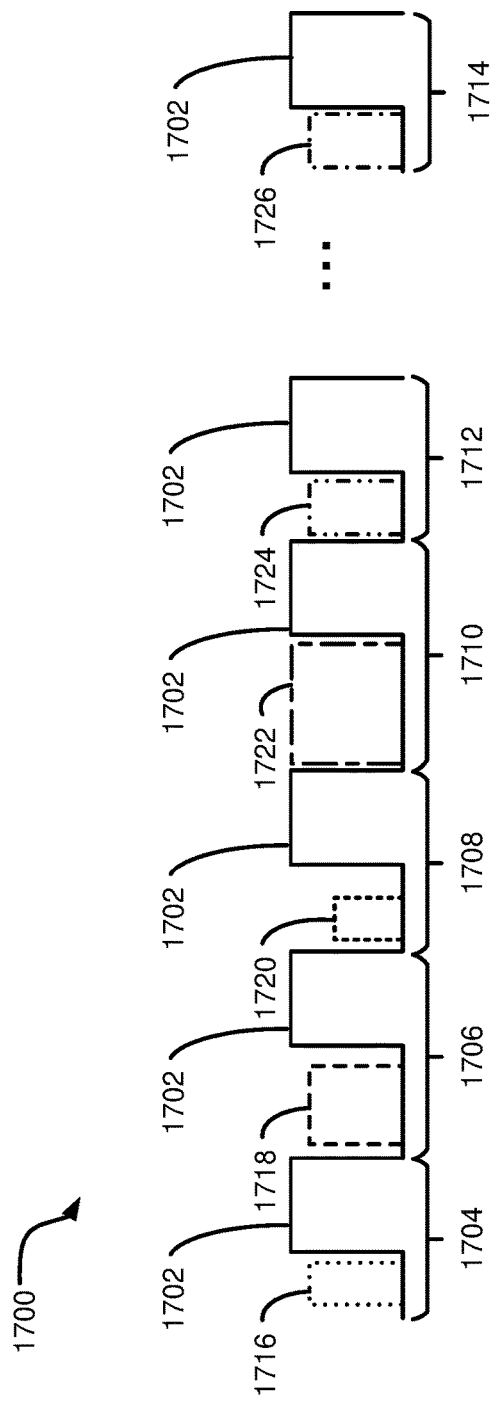
FIG. 17 is a schematic diagram illustrating a timing sequence for emission and readout for generating data frames in response to pulses of electromagnetic radiation.

FIG. 17 is a schematic diagram illustrating a timing diagram 1700 for emission and readout for generating an image. The solid line represents readout (peaks 1702) and blanking periods (valleys) for capturing a series of data frames 1704-1714. The series of data frames 1704-1714 may include a repeating series of data frames which may be used for generating mapping, multispectral, and/or fluorescence data that may be overlaid on an RGB video stream. The series of data frames include a first data frame 1704, a second data frame 1706, a third data frame 1708, a fourth data frame 1710, a fifth data frame 1712, and an Nth data frame 1726.

In one embodiment, each data frame is generated based on at least one pulse of EMR. The pulse of EMR is reflected and detected by the pixel array 125 and then read out in a subsequent readout (1702). Thus, each blanking period and readout results in a data frame for a specific waveband of EMR. For example, the first data frame 1704 may be generated based on a waveband of a first one or more pulses 1716, a second data frame 1706 may be generated based on a waveband of a second one or more pulses 1718, a third data frame 1708 may be generated based on a waveband of a third one or more pulses 1720, a fourth data frame 1710 may be generated based on a waveband of a fourth one or more pulses 1722, a fifth data frame 1712 may be generated based on a waveband of a fifth one or more pulses 1724, and an Nth data frame 1726 may be generated based on a waveband of an Nth one or more pulses 1726.

The pulses 1716-1726 may include energy from a single EMR source or from a combination of two or more EMR sources. For example, the waveband included in a single readout period or within the plurality of data frames 1704-1714 may be selected for a desired examination or detection of a specific tissue or condition. According to one embodiment, one or more pulses may include visible spectrum light for generating an RGB or black and white image while one or more additional pulses are emitted to sense a spectral response to a multispectral wavelength of EMR.

The pulses 1716-1726 are emitted according to a variable pulse cycle determined by the controller 104. For example, pulse 1716 may include a white light, pulse 1718 may include a multispectral waveband, pulse 1720 may include a white light, pulse 1722 may include a fluorescence waveband, pulse 1724 may include white light, and so forth.

The plurality of frames 1704-1714 are shown having varying lengths in readout periods and pulses having different lengths or intensities. The blanking period, pulse length or intensity, or the like may be selected based on the sensitivity of a monochromatic sensor to the specific wavelength, the power output capability of the EMR source(s), and/or the carrying capacity of the waveguide.

In one embodiment, dual image sensors may be used to obtain three-dimensional images or video feeds. A three-dimensional examination may allow for improved understanding of a three-dimensional structure of the examined region as well as a mapping of the different tissue or material types within the region.

In an example implementation, a patient is imaged with an endoscopic imaging system to identify quantitative diagnostic information about the patient's tissue pathology. In the example, the patient is suspected or known to suffer from a disease that can be tracked with multispectral imaging to observe the progression of the disease in the patient's tissue. The endoscopic imaging system pulses white light to generate an RGB video stream of the interior of the patient's body. Additionally, the endoscopic imaging system pulses one or more multispectral wavebands of light that permit the system to "see through" some tissues and generate imaging of the tissue affected by the disease. The endoscopic imaging system senses the reflected multispectral EMR to generate multispectral imaging data of the diseased tissue, and thereby identifies the location of the diseased tissue within the patient's body. The endoscopic imaging system may further emit a mapping pulsing scheme for generating a three-dimensional topographical map of the scene and calculating dimensions of objects within the scene. The location of the diseased tissue (as identified by the multispectral imaging data) may be combined with the topographical map and dimensions information that is calculated with the mapping data. Therefore, the precise location, size, dimensions, and topology of the diseased tissue can be identified. This information may be provided to a medical practitioner to aid in excising, imaging, or studying the diseased tissue. Additionally, this information may be provided to a robotic surgical system to enable the surgical system to excise the diseased tissue.

Figure 18:
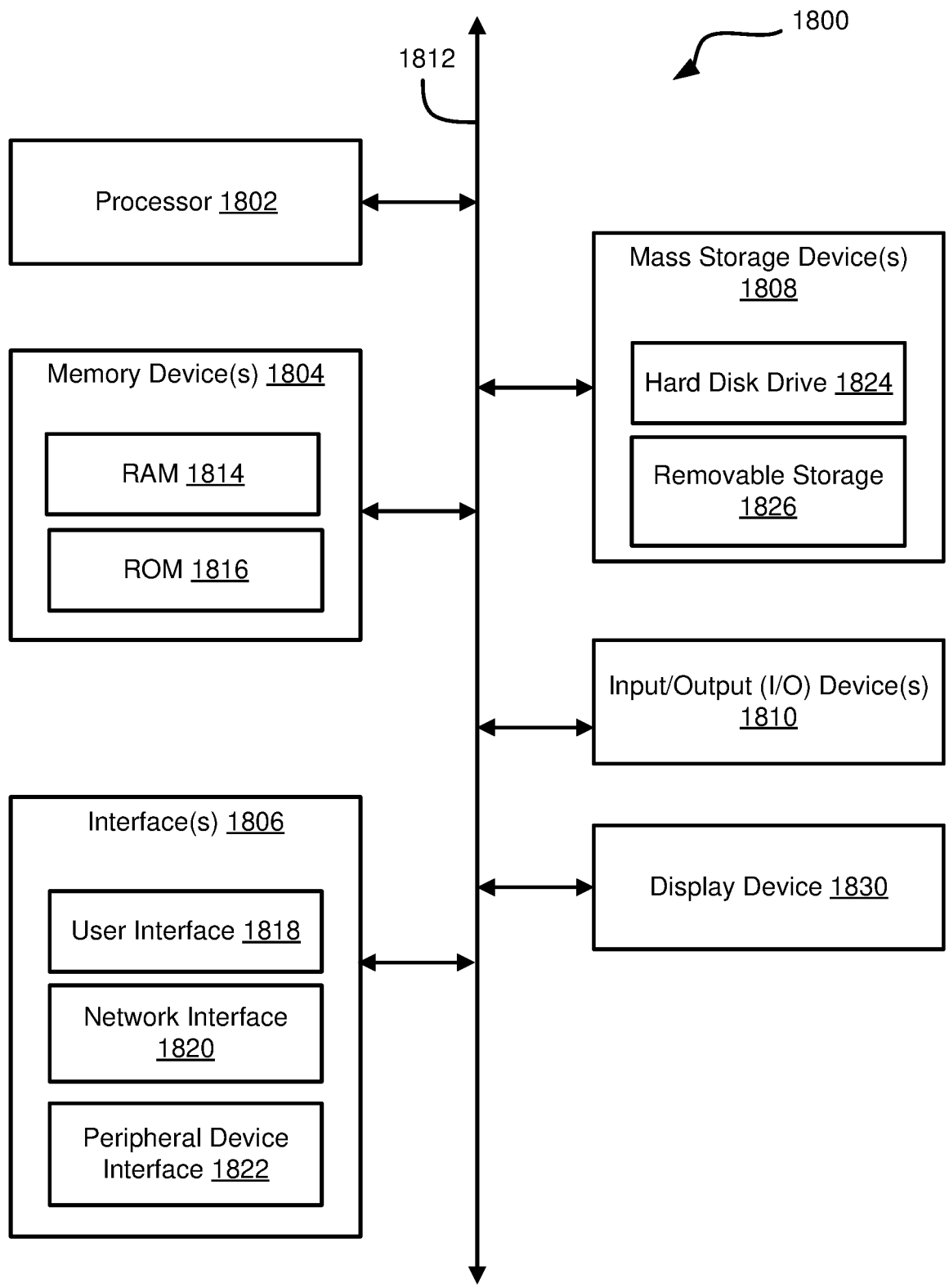
FIG. 18 is a schematic block diagram of an example computing device.

FIG. 18 illustrates a schematic block diagram of an example computing device 1800. The computing device 1800 may be used to perform various procedures, such as those discussed herein. The computing device 1800 can perform various monitoring functions as discussed herein, and can execute one or more application programs, such as the application programs or functionality described herein. The computing device 1800 can be any of a wide variety of computing devices, such as a desktop computer, in-dash computer, vehicle control system, a notebook computer, a server computer, a handheld computer, tablet computer and the like.

The computing device 1800 includes one or more processor(s) 1804, one or more memory device(s) 1804, one or more interface(s) 1806, one or more mass storage device(s) 1808, one or more Input/output (I/O) device(s) 1810, and a display device 1830 all of which are coupled to a bus 1812. Processor(s) 1804 include one or more processors or controllers that execute instructions stored in memory device(s) 1804 and/or mass storage device(s) 1808. Processor(s) 1804 may also include several types of computer-readable media, such as cache memory.

Memory device(s) 1804 include various computer-readable media, such as volatile memory (e.g., random access memory (RAM) 1814) and/or nonvolatile memory (e.g., read-only memory (ROM) 1816). Memory device(s) 1804 may also include rewritable ROM, such as Flash memory.

Mass storage device(s) 1808 include various computer readable media, such as magnetic tapes, magnetic disks, optical disks, solid-state memory (e.g., Flash memory), and so forth. As shown in FIG. 18, a particular mass storage device 1808 is a hard disk drive 1824. Various drives may also be included in mass storage device(s) 1808 to enable reading from and/or writing to the various computer readable media. Mass storage device(s) 1808 include removable media 1826 and/or non-removable media.

I/O device(s) 1810 include various devices that allow data and/or other information to be input to or retrieved from computing device 1800. Example I/O device(s) 1810 include cursor control devices, keyboards, keypads, microphones, monitors or other display devices, speakers, printers, network interface cards, modems, and the like.

Display device 1830 includes any type of device capable of displaying information to one or more users of computing device 1800. Examples of display device 1830 include a monitor, display terminal, video projection device, and the like.

Interface(s) 1806 include various interfaces that allow computing device 1800 to interact with other systems, devices, or computing environments. Example interface(s) 1806 may include any number of different network interfaces 1820, such as interfaces to local area networks (LANs), wide area networks (WANs), wireless networks, and the Internet. Other interface(s) include user interface 1818 and peripheral device interface 1822. The interface(s) 1806 may also include one or more user interface elements 1818. The interface(s) 1806 may also include one or more peripheral interfaces such as interfaces for printers, pointing devices (mice, track pad, or any suitable user interface now known to those of ordinary skill in the field, or later discovered), keyboards, and the like.

Bus 1812 allows processor(s) 1804, memory device(s) 1804, interface(s) 1806, mass storage device(s) 1808, and I/O device(s) 1810 to communicate with one another, as well as other devices or components coupled to bus 1812. Bus 1812 represents one or more of several types of bus structures, such as a system bus, PCI bus, IEEE bus, USB bus, and so forth.

For purposes of illustration, programs and other executable program components are shown herein as discrete blocks, such as block 302 for example, although it is understood that such programs and components may reside at various times in different storage components of computing device 1800 and are executed by processor(s) 1802. Alternatively, the systems and procedures described herein, including programs or other executable program components, can be implemented in hardware, or a combination of hardware, software, and/or firmware. For example, one or more application specific integrated circuits (ASICs) can be programmed to carry out one or more of the systems and procedures described herein.

EXAMPLES

The following examples pertain to preferred features of further embodiments:

Example 1 is a system. The system includes a stereo camera comprising a first image sensor and a second image sensor. The system includes a first optical filter that prevents the first image sensor from accumulating near infrared electromagnetic radiation. The system includes an emitter comprising a plurality of sources of electromagnetic radiation, wherein the plurality of sources comprises: a visible source that emits electromagnetic radiation within a visible waveband of the electromagnetic spectrum; and a near infrared source that emits electromagnetic radiation within a near infrared waveband of the electromagnetic spectrum. The first image sensor detects visible electromagnetic radiation and reads out a visible data frame in response to the emitter cycling on the visible source. The second image sensor detects the near infrared electromagnetic radiation and reads out a near infrared data frame in response to the emitter cycling on the near infrared source.

Example 2 is a system as in Example 1, further comprising a second optical filter; wherein the second optical filter prevents the second image sensor from accumulating electromagnetic radiation within a fluorescence excitation waveband; and wherein the second optical filter permits the second image sensor to accumulate electromagnetic radiation within a fluorescence relaxation waveband.

Example 3 is a system as in any of Examples 1-2, wherein the fluorescence excitation waveband comprises from about 770 nm to about 815 nm, and wherein the fluorescence relaxation waveband is within the near infrared waveband of the electromagnetic spectrum.

Example 4 is a system as in any of Examples 1-3, further comprising a controller in communication with the first image sensor, the second image sensor, and the emitter, and wherein the controller is configured to: instruct the first image sensor to accumulate electromagnetic radiation and read out a first pixel array according to a first image sensor cycle; instruct the second image sensor to accumulate electromagnetic radiation and read out a second pixel array according to a second image sensor cycle; and instruct the emitter to independently cycle at least a portion of the plurality of sources on and off according to a pulse cycle.

Example 5 is a system as in any of Examples 1-4, wherein the pulse cycle comprises: a pulsed emission by the visible source; and a pulsed emission by the near infrared source; wherein the controller synchronizes operations of the emitter and the stereo camera such that the emitter cycles on the visible source when the first image sensor and the second image sensor are undergoing a blanking period.

Example 6 is a system as in any of Examples 1-5, wherein the controller synchronizes operations of the emitter and the stereo camera such that the emitter cycles off the visible source when one or more of the first image sensor or the second image sensor is undergoing a readout period.

Example 7 is a system as in any of Examples 1-6, wherein the controller optimizes the pulse cycle to compensate for the near infrared source being weak relative to the visible source, and wherein the controller optimizes the pulse cycle by instructing the emitter to cycle on the near infrared source when at least one of the first image sensor or the second image sensor is undergoing a rolling readout sequence.

Example 8 is a system as in any of Examples 1-7, wherein the controller synchronizes operations of the emitter and the stereo camera such that the second image sensor accumulates the electromagnetic radiation within the near infrared waveband of the electromagnetic spectrum while the second image sensor is simultaneously reading out its pixel array.

Example 9 is a system as in any of Examples 1-8, wherein the controller optimizes the first image sensor cycle and the second image sensor cycle for generating color data frames and advanced data frames, and wherein the advanced data frames comprise one or more of: a multispectral data frame detected by at least one of the first image sensor or the second image sensor in response to the emitter pulsing a multispectral waveband of electromagnetic radiation; a fluorescence data frame detected by at least one of the first image sensor or the second image sensor in response to the emitter pulsing a fluorescence excitation waveband of electromagnetic radiation; or a mapping data frame detected by at least one of the first image sensor or the second image sensor in response to the emitter pulsing electromagnetic radiation diffracted into a mapping pattern.

Example 10 is a system as in any of Examples 1-9, wherein the controller optimizes the first image sensor cycle and the second image sensor cycle such that: the first image sensor outputs color data frames that are used to provide color visualization of a scene to a display; the second image sensor outputs color data frames that are used to provide the color visualization of the scene to the display; and the second image sensor further outputs advanced data frames that are provided to an algorithm configured to identify a tissue within the scene.

Example 11 is a system as in any of Examples 1-10, wherein each of the first image sensor and the second image sensor outputs the mapping data frame.

Example 12 is a system as in any of Examples 1-11, wherein the first image sensor does not output either of the multispectral data frame or the fluorescence data frame.

Example 13 is a system as in any of Examples 1-12, wherein the first image sensor reads out the first pixel array and outputs a filler data frame in response to the emitter pulsing either of the multispectral waveband of electromagnetic radiation or the fluorescence excitation waveband of electromagnetic radiation, and wherein the controller discards the filler data frame such that the filler data frame is not provided to the display or the algorithm.

Example 14 is a system as in any of Examples 1-13, wherein the controller optimizes the first image sensor cycle and the second image sensor cycle such that the first image sensor only reads out the first pixel array on a pixel-by-pixel basis according to a rolling readout scheme and without binning.

Example 15 is a system as in any of Examples 1-14, wherein the second image sensor reads out the second pixel array according to a binning configuration when reading out the multispectral data frame or the fluorescence data frame.

Example 16 is a system as in any of Examples 1-15, wherein the second image sensor reads out the second pixel array on the pixel-by-pixel basis according to the rolling readout scheme and without binning when reading out the color data frames.

Example 17 is a system as in any of Examples 1-16, wherein the second image sensor only reads out the second pixel array according to the binning configuration.

Example 18 is a system as in any of Examples 1-17, wherein the visible source comprises a white light source, and wherein the plurality of sources of the emitter further comprises a narrowband visible source that emits electromagnetic radiation selected for spectral visualization.

Example 19 is a system as in any of Examples 1-18, wherein the narrowband visible source comprises one or more of: a first narrowband visible source tuned to emit electromagnetic radiation within a waveband from about 513 nm to about 545 nm; or a second narrowband visible source tuned to emit electromagnetic radiation within a waveband from about 565 nm to about 585 nm.

Example 20 is a system as in any of Examples 1-19, wherein the plurality of sources of the emitter further comprises a spectral source tuned to emit electromagnetic radiation within a waveband from about 900 nm to about 1000 nm.

Example 21 is a system as in any of Examples 1-20, wherein the near infrared source is tuned to emit a fluorescence excitation wavelength for fluorescing a reagent or tissue, and wherein the near infrared source comprises one or more of: a first fluorescence source tuned to emit electromagnetic radiation within a waveband from about 770 nm to about 795 nm; or a second fluorescence source tuned to emit electromagnetic radiation within a waveband from about 790 nm to about 815 nm.

Example 22 is a system as in any of Examples 1-21, wherein the emitter further comprises a quantum-dot-array diffraction element configured to diffract electromagnetic radiation into a mapping pattern.

Example 23 is a system as in any of Examples 1-22, wherein the mapping pattern comprises one or more of vertical hashing, horizontal hashing, a dot array, or a grid array.

Example 24 is a system as in any of Examples 1-23, wherein the visible source is a white light source.

Example 25 is a system as in any of Examples 1-24, wherein the near infrared source is a narrowband near infrared source configured to emit electromagnetic radiation within a waveband that is 20 nm-wide or less.

It will be appreciated that various features disclosed herein provide significant advantages and advancements in the art. The following claims are exemplary of some of those features.

In the foregoing Detailed Description of the Disclosure, various features of the disclosure are grouped together in a single embodiment for the purpose of streamlining the disclosure. This method of disclosure is not to be interpreted as reflecting an intention that the claimed disclosure requires more features than are expressly recited in each claim. Rather, inventive aspects lie in less than all features of a single foregoing disclosed embodiment.

It is to be understood that any features of the above-described arrangements, examples, and embodiments may be combined in a single embodiment comprising a combination of features taken from any of the disclosed arrangements, examples, and embodiments.

It is to be understood that the above-described arrangements are only illustrative of the application of the principles of the disclosure. Numerous modifications and alternative arrangements may be devised by those skilled in the art without departing from the spirit and scope of the disclosure and the appended claims are intended to cover such modifications and arrangements.

Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

Further, where appropriate, functions described herein can be performed in one or more of: hardware, software, firmware, digital components, or analog components. For example, one or more application specific integrated circuits (ASICs) or field programmable gate arrays (FPGAs) can be programmed to carry out one or more of the systems and procedures described herein. Certain terms are used throughout the following description and claims to refer to particular system components. As one skilled in the art will appreciate, components may be referred to by different names. This document does not intend to distinguish between components that differ in name, but not function.

The foregoing description has been presented for the purposes of illustration and description. It is not intended to be exhaustive or to limit the disclosure to the precise form disclosed. Many modifications and variations are possible in light of the above teaching. Further, it should be noted that any or all the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A system comprising:
   a stereo camera comprising a first image sensor and a second image sensor;
   a first optical filter that prevents the first image sensor from accumulating near infrared electromagnetic radiation; and
   an emitter comprising a plurality of sources of electromagnetic radiation, wherein the plurality of sources comprises:
      a visible source that emits electromagnetic radiation within a visible waveband of the electromagnetic spectrum; and
      a near infrared source that emits electromagnetic radiation within a near infrared waveband of the electromagnetic spectrum; and
   a controller in communication with the first image sensor, the second image sensor, and the emitter;
   wherein the first image sensor detects visible electromagnetic radiation and reads out a visible data frame in response to the emitter cycling on the visible source;
   wherein the second image sensor detects near infrared electromagnetic radiation and reads out a near infrared data frame in response to the emitter cycling on the near infrared source;
   wherein the controller is configured to instruct the emitter to independently cycle at least a portion of the plurality of sources on and off according to a pulse cycle; and
   wherein the controller instructs the emitter to cycle on at least one of the plurality of sources of electromagnetic radiation when at least one of the first image sensor or the second image sensor is undergoing a readout sequence.

2. The system of claim 1, further comprising a second optical filter;
   wherein the second optical filter prevents the second image sensor from accumulating electromagnetic radiation within a fluorescence excitation waveband; and
   wherein the second optical filter permits the second image sensor to accumulate electromagnetic radiation within a fluorescence relaxation waveband.

3. The system of claim 2, wherein the fluorescence excitation waveband comprises from about 770 nm to about 815 nm, and wherein the fluorescence relaxation waveband is within the near infrared waveband of the electromagnetic spectrum.

4. The system of claim 2, wherein each of the first optical filter and the second optical filter permits electromagnetic radiation within the visible waveband of the electromagnetic spectrum to pass through and be detected by the first image sensor or the second image sensor.

5. The system of claim 1, wherein the controller is configured to:
   instruct the first image sensor to accumulate electromagnetic radiation and read out a first pixel array according to a first image sensor cycle; and
   instruct the second image sensor to accumulate electromagnetic radiation and read out a second pixel array according to a second image sensor cycle.

6. The system of claim 5, wherein the pulse cycle comprises:
   a pulsed emission by the visible source; and
   a pulsed emission by the near infrared source;
   wherein the controller synchronizes operations of the emitter and the stereo camera such that the emitter cycles on the visible source when the first image sensor and the second image sensor are undergoing a blanking period.

7. The system of claim 6, wherein the controller optimizes the pulse cycle to compensate for the near infrared source being weak relative to the visible source, and wherein the controller optimizes the pulse cycle by instructing the emitter to cycle on the near infrared source when at least one of the first image sensor or the second image sensor is undergoing a rolling readout sequence.

8. The system of claim 7, wherein the controller synchronizes operations of the emitter and the stereo camera such that the second image sensor accumulates the electromagnetic radiation within the near infrared waveband of the electromagnetic spectrum while the second image sensor is simultaneously reading out its pixel array.

9. The system of claim 5, wherein the controller optimizes the first image sensor cycle and the second image sensor cycle for generating color data frames and advanced data frames, and wherein the advanced data frames comprise one or more of:
- a multispectral data frame detected by at least one of the first image sensor or the second image sensor in response to the emitter pulsing a multispectral waveband of electromagnetic radiation selected to elicit a spectral response from a tissue;
- a fluorescence data frame detected by at least one of the first image sensor or the second image sensor in response to the emitter pulsing a fluorescence excitation waveband of electromagnetic radiation selected to fluoresce a reagent or tissue; or
- a mapping data frame detected by at least one of the first image sensor or the second image sensor in response to the emitter pulsing electromagnetic radiation diffracted into a mapping pattern.

10. The system of claim 9, wherein the controller optimizes the first image sensor cycle and the second image sensor cycle such that:
- the first image sensor outputs color data frames that are used to provide color visualization of a scene; and
- the second image sensor outputs advanced data frames that are provided to an algorithm configured to identify a tissue within the scene.

11. The system of claim 10, wherein each of the first image sensor and the second image sensor outputs the mapping data frame.

12. The system of claim 10, wherein the first image sensor does not output either of the multispectral data frame or the fluorescence data frame.

13. The system of claim 10, wherein the first image sensor reads out the first pixel array and outputs a filler data frame in response to the emitter pulsing either of the multispectral waveband of electromagnetic radiation or the fluorescence excitation waveband of electromagnetic radiation, and wherein the controller discards the filler data frame such that the filler data frame is not provided to a display or the algorithm.

14. The system of claim 10, wherein the controller optimizes the first image sensor cycle and the second image sensor cycle such that the first image sensor only reads out the first pixel array on a pixel-by-pixel basis according to a rolling readout scheme and without binning.

15. The system of claim 14, wherein the second image sensor reads out the second pixel array according to a binning configuration when reading out the multispectral data frame or the fluorescence data frame.

16. The system of claim 15, wherein the second image sensor reads out the second pixel array on the pixel-by-pixel basis according to the rolling readout scheme and without binning when reading out the color data frames.

17. The system of claim 15, wherein the second image sensor only reads out the second pixel array according to the binning configuration.

18. The system of claim 10, wherein:
- the first image sensor outputs the color data frames at full resolution by reading each pixel within the first pixel array on a pixel-by-pixel basis without binning;
- the second image sensor outputs the advanced data frames at a lower resolution by reading the second pixel array according to a binning configuration; and
the second image sensor outputs data frames at a faster frame rate than the first image sensor.

19. The system of claim 1, wherein the visible source comprises a white light source, and wherein the plurality of sources of the emitter further comprises a narrowband spectral source that emits electromagnetic radiation selected for spectral visualization, and wherein the narrowband visible source comprises one or more of:
- a first narrowband spectral source tuned to emit electromagnetic radiation within a first visible waveband;
- a second narrowband spectral source tuned to emit electromagnetic radiation within a second visible waveband; or
- a third narrowband spectral source tuned to emit electromagnetic radiation within the near infrared waveband of the electromagnetic spectrum.

20. The system of claim 1, wherein the near infrared source is tuned to emit a fluorescence excitation wavelength for fluorescing a reagent or tissue, and wherein the near infrared source comprises one or more of:
- a first fluorescence source tuned to emit electromagnetic radiation within a waveband from about 770 nm to about 795 nm; or
- a second fluorescence source tuned to emit electromagnetic radiation within a waveband from about 790 nm to about 815 nm.

* * * * *